(12) United States Patent
Narimatsu et al.

(10) Patent No.: US 7,494,800 B2
(45) Date of Patent: Feb. 24, 2009

(54) N-ACETYLGALACTOSAMINE TRANSFERASES AND NUCLEIC ACIDS ENCODING THE SAME

(75) Inventors: Hisashi Narimatsu, Ibaraki (JP); Masanori Gotoh, Ibaraki (JP); Takashi Sato, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 143 days.

(21) Appl. No.: 10/524,505

(22) PCT Filed: Aug. 13, 2003

(86) PCT No.: PCT/JP03/10309

§ 371 (c)(1),
(2), (4) Date: Feb. 14, 2005

(87) PCT Pub. No.: WO2004/016790

PCT Pub. Date: Feb. 26, 2004

(65) Prior Publication Data

US 2006/0234232 A1  Oct. 19, 2006

(30) Foreign Application Priority Data

Aug. 14, 2002 (JP) .............................. 2002-236292

(51) Int. Cl.
*C12N 15/54* (2006.01)
*C12N 15/63* (2006.01)
*C12N 1/21* (2006.01)
*C12N 9/10* (2006.01)

(52) U.S. Cl. .................... 435/252.3; 435/325; 435/193; 435/320.1; 536/23.2

(58) Field of Classification Search .................. None
See application file for complete search history.

(56) References Cited

U.S. PATENT DOCUMENTS 6,943,241 B2 * 9/2005 Isogai et al. ............... 536/23.1
7,193,069 B2 * 3/2007 Isogai et al. ............... 536/23.1

FOREIGN PATENT DOCUMENTS

| EP | 1308459 | * | 5/2003 |
| JP | 2001-165933 | | 6/2001 |
| WO | WO 01/53524 A2 | | 7/2001 |
| WO | 01/72832 | * | 10/2001 |
| WO | WO 01/90369 | | 11/2001 |

OTHER PUBLICATIONS

GenBank Accesion No. AK097681 (Jul. 2002).*
Database EMBL [Online], Jun. 27, 2002 "Mus musculus beta-1, 4-N-acetyl-galactosaminyl transferase 4, mRNA (cDNA clone Image:5036555)", XP002432308, retrieved from EBI accession No. EMBL:BC031982, Database accession No. BC031982.
Database EMBL [Online] Oct. 31, 2001 "Homo sapiens cDNA FLJ25045 fis, clone CBL03591" XP002432309, retrieved from EBI accession No. EMBL AK057774, Database accession No. AK057774.
Gastinel et al, "Crystal structures of the bovine β4galactosyltransferase catalytic domain and its complex with uridine diphosphogalactose", The EMBO Journal, 1999, vol. 18, No. 13, pp. 3546-3557.
Supplementary European Search Report dated May 7, 2007, issued in connection with EP 03 78 8102.
Kawar et al, The Journal of Biological Chemistry, 2002, vol. 277, No. 38, pp. 34924-34932.
Sato et al, The Journal of Biological Chemistry, 2003, vol. 278, No. 48, pp. 47534-47544.
Gotoh et al, FEBS Letters, 2004, vol. 562, pp. 134-140.
Sugita et al, The Journal of Biological Chemistry, 1989, vol. 264, No. 25, pp. 15028-15033.
Helling et al, Eur. J. Biochem. 1991, vol. 200, pp. 409-421.
Weisshaar et al, Eur. J. Biochem. 1991, vol. 195, pp. 257-268.
White et al, The Journal of Biological Chemistry, 1995, vol. 270, No. 41, pp. 24156-24165.
Bennett et al, The Journal of Biological Chemistry, 1996, vol. 271, No. 29, pp. 17006-17012.
Bennett et al, The Journal of Biological Chemistry, 1998, vol. 273, No. 46, pp. 30472-30481.
Bennett et al, The Journal of Biological Chemistry, 1999, vol. 274, No. 36, pp. 25362-25370.
Bennett et al, FEBS Letters, 1999, vol. 460, pp. 226-230.
White et al, Gene, 2000, vol. 246, pp. 347-356.
Toba et al, Biochimica et Biophysica Acta, 2000, vol. 1493, pp. 264-268.
Nagata et al, The Journal of Biological Chemistry, 1992, vol. 267, No. 17, pp. 12082-12089.
Yamamoto et al, The Journal of Biological Chemistry, 1990, vol. 265, No. 2, pp. 1146-1151.
Xu et al, The Journal of Biological Chemistry, 1999, vol. 274, No. 41, pp. 29390-29398.
Guo et al, FEBS Letters, 2002, vol. 524, pp. 211-218.
Ishizuka et al, J. Carbohydrate Chemistry, 1999, vol. 18, No. 5, pp. 523-533.

(Continued)

*Primary Examiner*—Rebecca Prouty
(74) *Attorney, Agent, or Firm*—Nixon & Vanderhye P.C.

(57) ABSTRACT

An enzyme which transfers N-acetylgalactosamine to N-acetylglucosamine via a β1-4 linkage was isolated and the structure of its gene was explained. This led to the production of said enzyme or the like by genetic engineering techniques, the production of oligosaccharides using said enzyme, and the diagnosis of diseases on the basis of said gene or the like. The present invention uses a protein having the amino acid sequence shown in SEQ ID NO: 1, 3, 26 or 27 in the Sequence Listing or a variant of said amino acid sequence wherein one or more acids are substituted or deleted, or one or more acids are inserted or added and having the activity of transferring N-acetylgalactosamine (GalNAc) to N-acetylglucosamine serving as a substrate via a β1-4 linkage and nucleic acids encoding said protein.

4 Claims, 6 Drawing Sheets

OTHER PUBLICATIONS

Neeleman A.P. et al, "alpha-Lactalbumin affects the acceptor specificity of Lymaeastagnalis albumen gland UDP-GalNac:GlcNAcbeta-R beta1-4-N-acetylgalactosaminyltransferase: Synthesis of GalNacbeta1-4Glc, "Proc.Natl. Acad. Sci. USA, 1996, vol. 93, p. 10111-10116.

Gotoh M. et al, "Enzymatic Synthesis of Chondroitin with a Novel Chondroitin Sulfate N-Acetylgalacetosaminyltransferase That Transfers N-Acetylgalactosamine to Glucuronic Acid in Initiation and Elongation of Chondroitin Sulfate Synthesis", J. Biol. Chem., Oct. 11, 2002 (Epub Aug. 5, 2002), vol. 277, No. 41, pp. 38189-38196.

* cited by examiner

SEQUENCE LISTING

<160> NUMBER OF SEQ ID NOS: 34

<210> SEQ ID NO 1
<211> LENGTH: 1039
<212> TYPE: PRT
<213> ORGANISM: Homo sapiens

<400> SEQUENCE: 1

Met Pro Arg Leu Pro Val Lys Lys Ile Arg Lys Gln Met Lys Leu Leu
 1               5                  10                  15

```
Leu Leu Leu Leu Leu Leu Ser Cys Ala Ala Trp Leu Thr Tyr Val His
            20                  25                  30

Leu Gly Leu Val Arg Gln Gly Arg Ala Leu Arg Gln Arg Leu Gly Tyr
        35                  40                  45

Gly Arg Asp Gly Glu Lys Leu Thr Ser Glu Thr Asp Gly Arg Gly Val
        50                  55                  60

His Ala Ala Pro Ser Thr Gln Arg Ala Glu Asp Ser Ser Glu Ser Arg
 65                  70                  75                  80

Glu Glu Glu Gln Ala Pro Glu Gly Arg Asp Leu Asp Met Leu Phe Pro
                85                  90                  95

Gly Gly Ala Gly Arg Leu Pro Leu Asn Phe Thr His Gln Thr Pro Pro
                100                 105                 110

Trp Arg Glu Glu Tyr Lys Gly Gln Val Asn Leu His Val Phe Glu Asp
            115                 120                 125

Trp Cys Gly Gly Ala Val Gly His Leu Arg Arg Asn Leu His Phe Pro
        130                 135                 140

Leu Phe Pro His Thr Arg Thr Thr Val Lys Lys Leu Ala Val Ser Pro
145                 150                 155                 160

Lys Trp Lys Asn Tyr Gly Leu Arg Ile Phe Gly Phe Ile His Pro Ala
                165                 170                 175

Arg Asp Gly Asp Val Gln Phe Ser Val Ala Ser Asp Asp Asn Ser Glu
            180                 185                 190

Phe Trp Leu Ser Leu Asp Glu Ser Pro Ala Ala Ala Gln Leu Val Ala
        195                 200                 205

Phe Val Gly Lys Thr Gly Ser Glu Trp Thr Ala Pro Gly Glu Phe Thr
    210                 215                 220

Lys Phe Ser Ser Gln Val Ser Lys Pro Arg Arg Leu Met Ala Ser Arg
225                 230                 235                 240

Arg Tyr Tyr Phe Glu Leu Leu His Lys Gln Asp Asp Arg Gly Ser Asp
                245                 250                 255

His Val Glu Val Gly Trp Arg Ala Phe Leu Pro Gly Leu Lys Phe Glu
            260                 265                 270

Val Ile Ser Ser Ala His Ile Ser Leu Tyr Thr Asp Glu Ser Ala Leu
        275                 280                 285

Lys Met Asp His Val Ala His Val Pro Gln Ser Pro Ala Ser His Val
    290                 295                 300

Gly Gly Arg Pro Pro Gln Glu Glu Thr Ser Ala Asp Met Leu Arg Pro
305                 310                 315                 320

Asp Pro Arg Asp Thr Phe Phe Leu Thr Pro Arg Met Glu Ser Ser Ser
                325                 330                 335

Leu Glu Asn Val Leu Glu Pro Cys Ala Tyr Ala Pro Thr Tyr Val Val
            340                 345                 350

Lys Asp Phe Pro Ile Ala Arg Tyr Gln Gly Leu Gln Phe Val Tyr Leu
        355                 360                 365

Ser Phe Val Tyr Pro Asn Asp Tyr Thr Arg Leu Thr His Met Glu Thr
    370                 375                 380

Asp Asn Lys Cys Phe Tyr Arg Glu Ser Pro Leu Tyr Leu Glu Arg Phe
385                 390                 395                 400

Gly Phe Tyr Lys Tyr Met Lys Met Asp Lys Glu Glu Gly Asp Glu Asp
                405                 410                 415

Glu Glu Asp Glu Val Gln Arg Arg Ala Phe Leu Phe Leu Asn Pro Asp
            420                 425                 430
```

-continued

```
Asp Phe Leu Asp Asp Glu Asp Gly Glu Leu Leu Asp Ser Leu Glu
            435                 440                 445

Pro Thr Glu Ala Ala Pro Pro Arg Ser Gly Pro Gln Ser Pro Ala Pro
450                 455                 460

Ala Ala Pro Ala Gln Pro Gly Ala Thr Leu Ala Pro Thr Pro Pro
465                 470                 475                 480

Arg Pro Arg Asp Gly Gly Thr Pro Arg His Ser Arg Ala Leu Ser Trp
                    485                 490                 495

Ala Ala Arg Ala Ala Arg Pro Leu Pro Leu Phe Leu Gly Arg Ala Pro
                500                 505                 510

Pro Pro Arg Pro Ala Val Glu Gln Pro Pro Lys Val Tyr Val Thr
            515                 520                 525

Arg Val Arg Pro Gly Gln Arg Ala Ser Pro Arg Ala Pro Ala Pro Arg
            530                 535                 540

Ala Pro Trp Pro Pro Phe Pro Gly Val Phe Leu His Pro Arg Pro Leu
545                 550                 555                 560

Pro Arg Val Gln Leu Arg Ala Pro Pro Arg Pro Arg Pro His Gly
                565                 570                 575

Arg Arg Thr Gly Gly Pro Gln Ala Thr Gln Pro Arg Pro Ala Arg
            580                 585                 590

Ala Gln Ala Thr Gln Gly Gly Arg Glu Gly Gln Ala Arg Thr Leu Gly
            595                 600                 605

Pro Ala Ala Pro Thr Val Asp Ser Asn Leu Ser Ser Glu Ala Arg Pro
            610                 615                 620

Val Thr Ser Phe Leu Ser Leu Ser Gln Val Ser Gly Pro Gln Leu Pro
625                 630                 635                 640

Gly Glu Gly Glu Glu Glu Glu Gly Glu Asp Asp Gly Ala Pro Gly
                    645                 650                 655

Asp Glu Ala Ala Ser Glu Asp Ser Glu Glu Ala Ala Gly Pro Ala Leu
                660                 665                 670

Gly Arg Trp Arg Glu Asp Ala Ile Asp Trp Gln Arg Thr Phe Ser Val
            675                 680                 685

Gly Ala Val Asp Phe Glu Leu Leu Arg Ser Asp Trp Asn Asp Leu Arg
            690                 695                 700

Cys Asn Val Ser Gly Asn Leu Gln Leu Pro Glu Ala Glu Ala Val Asp
705                 710                 715                 720

Val Thr Ala Gln Tyr Met Glu Arg Leu Asn Ala Arg His Gly Gly Arg
                    725                 730                 735

Phe Ala Leu Leu Arg Ile Val Asn Val Glu Lys Arg Arg Asp Ser Ala
                740                 745                 750

Arg Gly Ser Arg Phe Leu Leu Glu Leu Glu Leu Gln Glu Arg Gly Gly
            755                 760                 765

Gly Arg Leu Arg Leu Ser Glu Tyr Val Phe Leu Arg Leu Pro Gly Ala
770                 775                 780

Arg Val Gly Asp Ala Asp Gly Glu Ser Pro Glu Pro Ala Pro Ala Ala
785                 790                 795                 800

Ser Val Arg Pro Asp Gly Arg Pro Glu Leu Cys Arg Pro Leu Arg Leu
                805                 810                 815

Ala Trp Arg Gln Asp Val Met Val His Phe Ile Val Pro Val Lys Asn
            820                 825                 830

Gln Ala Arg Trp Val Ala Gln Phe Leu Ala Asp Met Ala Ala Leu His
            835                 840                 845

Ala Arg Thr Gly Asp Ser Arg Phe Ser Val Val Leu Val Asp Phe Glu
```

```
                    850                 855                 860
Ser Glu Asp Met Asp Val Glu Arg Ala Leu Arg Ala Ala Arg Leu Pro
865                 870                 875                 880

Arg Tyr Gln Tyr Leu Arg Arg Thr Gly Asn Phe Glu Arg Ser Ala Gly
                885                 890                 895

Leu Gln Ala Gly Val Asp Ala Val Glu Asp Ala Ser Ser Ile Val Phe
                900                 905                 910

Leu Cys Asp Leu His Ile His Phe Pro Pro Asn Ile Leu Asp Gly Ile
            915                 920                 925

Arg Lys His Cys Val Glu Gly Arg Leu Ala Phe Ala Pro Val Val Met
        930                 935                 940

Arg Leu Ser Cys Gly Ser Ser Pro Arg Asp Pro His Gly Tyr Trp Glu
945                 950                 955                 960

Val Asn Gly Phe Gly Leu Phe Gly Ile Tyr Lys Ser Asp Phe Asp Arg
                965                 970                 975

Val Gly Gly Met Asn Thr Glu Glu Phe Arg Asp Gln Trp Gly Gly Glu
                980                 985                 990

Asp Trp Glu Leu Leu Asp Arg Val Leu Gln Ala Gly Leu Glu Val Glu
            995                 1000                1005

Arg Leu Arg Leu Arg Asn Phe Tyr His His Tyr His Ser Lys Arg Gly
       1010                1015                1020

Met Trp Ser Val Arg Ser Arg Lys Gly Ser Arg Thr Gly Ala Ser
1025                1030                1035                1039

<210> SEQ ID NO 2
<211> LENGTH: 3120
<212> TYPE: DNA
<213> ORGANISM: Homo sapiens

<400> SEQUENCE: 2 atg ccg cgg ctc ccg gtg aag aag atc cgt aag cag atg aag ctg ctg      48
Met Pro Arg Leu Pro Val Lys Lys Ile Arg Lys Gln Met Lys Leu Leu
1               5                   10                  15 ctg ctg ctg ctg ctg ctg agc tgc gcc gcg tgg ctc acc tac gtg cac      96
Leu Leu Leu Leu Leu Leu Ser Cys Ala Ala Trp Leu Thr Tyr Val His
                20                  25                  30 ctg ggc ctg gtg cgc cag gga cgc gcg ctg cgc cag cgc ctg ggc tac     144
Leu Gly Leu Val Arg Gln Gly Arg Ala Leu Arg Gln Arg Leu Gly Tyr
            35                  40                  45 ggg cga gat ggt gag aag ctg acc agt gag acc gac ggc cgg ggg gtc     192
Gly Arg Asp Gly Glu Lys Leu Thr Ser Glu Thr Asp Gly Arg Gly Val
        50                  55                  60 cac gct gcg cca tcc aca cag agg gct gag gac tcc agt gag agc cgt     240
His Ala Ala Pro Ser Thr Gln Arg Ala Glu Asp Ser Ser Glu Ser Arg
65                  70                  75                  80 gaa gag gag caa gcg ccc gaa ggt cgg gac cta gac atg ctg ttt cct     288
Glu Glu Glu Gln Ala Pro Glu Gly Arg Asp Leu Asp Met Leu Phe Pro
                85                  90                  95 ggg ggg gct ggg agg ctg cca ctg aac ttc acc cat cag aca ccc cca     336
Gly Gly Ala Gly Arg Leu Pro Leu Asn Phe Thr His Gln Thr Pro Pro
                100                 105                 110 tgg cgg gag gag tac aag ggg cag gtg aac ctg cac gtg ttt gag gac     384
Trp Arg Glu Glu Tyr Lys Gly Gln Val Asn Leu His Val Phe Glu Asp
            115                 120                 125 tgg tgt ggg ggc gcc gtg ggc cac ctg agg agg aac ctg cac ttc ccg     432
Trp Cys Gly Gly Ala Val Gly His Leu Arg Arg Asn Leu His Phe Pro
        130                 135                 140
```

```
ctg ttc cct cat acg cgc acc acc gtg aag aag ttg gcc gtg tcc ccc      480
Leu Phe Pro His Thr Arg Thr Thr Val Lys Lys Leu Ala Val Ser Pro
145                 150                 155                 160 aag tgg aag aac tat gga ctc cgt att ttt ggt ttc atc cac ccg gcg      528
Lys Trp Lys Asn Tyr Gly Leu Arg Ile Phe Gly Phe Ile His Pro Ala
                165                 170                 175 agg gac gga gac gtc cag ttt tct gtg gcc tca gac gac aac tcg gag      576
Arg Asp Gly Asp Val Gln Phe Ser Val Ala Ser Asp Asp Asn Ser Glu
        180                 185                 190 ttc tgg ctg agt ctg gac gag agc cct gct gct gcc cag ctt gtg gcc      624
Phe Trp Leu Ser Leu Asp Glu Ser Pro Ala Ala Ala Gln Leu Val Ala
    195                 200                 205 ttt gtg ggc aag act ggc tcc gag tgg aca gcg cct gga gaa ttc acc      672
Phe Val Gly Lys Thr Gly Ser Glu Trp Thr Ala Pro Gly Glu Phe Thr
210                 215                 220 aag ttc agc tcc cag gtg tcc aag ccc agg cgg ctc atg gcc tcc cgg      720
Lys Phe Ser Ser Gln Val Ser Lys Pro Arg Arg Leu Met Ala Ser Arg
225                 230                 235                 240 agg tac tac ttt gag ttg ctg cac aag cag gac gac cgc ggc tcg gac      768
Arg Tyr Tyr Phe Glu Leu Leu His Lys Gln Asp Asp Arg Gly Ser Asp
                245                 250                 255 cac gtg gaa gtg ggc tgg cga gct ttc ctg ccc ggc ctg aag ttc gag      816
His Val Glu Val Gly Trp Arg Ala Phe Leu Pro Gly Leu Lys Phe Glu
        260                 265                 270 gtc atc agc tct gct cac atc tcc ctg tac aca gat gag tca gcc ttg      864
Val Ile Ser Ser Ala His Ile Ser Leu Tyr Thr Asp Glu Ser Ala Leu
    275                 280                 285 aag atg gac cac gtg gcg cac gtc ccc cag tct cca gcc agc cac gtg      912
Lys Met Asp His Val Ala His Val Pro Gln Ser Pro Ala Ser His Val
290                 295                 300 ggg ggg cgt ccg ccg cag gag gag acc agc gca gac atg ctg cgg cca      960
Gly Gly Arg Pro Pro Gln Glu Glu Thr Ser Ala Asp Met Leu Arg Pro
305                 310                 315                 320 gat ccc agg gat acc ttt ttc ctc act cca cgc atg gaa tct tcg agc     1008
Asp Pro Arg Asp Thr Phe Phe Leu Thr Pro Arg Met Glu Ser Ser Ser
                325                 330                 335 ctg gag aac gtg ctg gag ccc tgc gcc tac gcc ccc acc tac gtg gtc     1056
Leu Glu Asn Val Leu Glu Pro Cys Ala Tyr Ala Pro Thr Tyr Val Val
        340                 345                 350 aag gac ttc ccg atc gcc aga tac cag ggc ctg caa ttt gtg tac ctg     1104
Lys Asp Phe Pro Ile Ala Arg Tyr Gln Gly Leu Gln Phe Val Tyr Leu
    355                 360                 365 tcc ttc gtt tat ccc aac gac tac act cgc ctc acc cac atg gag acg     1152
Ser Phe Val Tyr Pro Asn Asp Tyr Thr Arg Leu Thr His Met Glu Thr
370                 375                 380 gac aac aag tgc ttc tac cgc gag tct ccg ctg tat ctg gag agg ttt     1200
Asp Asn Lys Cys Phe Tyr Arg Glu Ser Pro Leu Tyr Leu Glu Arg Phe
385                 390                 395                 400 ggg ttc tat aaa tac atg aag atg gac aag gag gag ggg gat gag gat     1248
Gly Phe Tyr Lys Tyr Met Lys Met Asp Lys Glu Glu Gly Asp Glu Asp
                405                 410                 415 gaa gaa gac gag gtg cag cgc cga gcc ttc ctc ttc ctc aac ccg gac     1296
Glu Glu Asp Glu Val Gln Arg Arg Ala Phe Leu Phe Leu Asn Pro Asp
        420                 425                 430 gac ttc ctg gac gac gag gac gag ggg gag ctg ctc gac agc ctg gag     1344
Asp Phe Leu Asp Asp Glu Asp Glu Gly Glu Leu Leu Asp Ser Leu Glu
    435                 440                 445 ccc acc gag gcg gcc ccg ccc agg agc ggc ccc cag tcc ccc gcc cca     1392
Pro Thr Glu Ala Ala Pro Pro Arg Ser Gly Pro Gln Ser Pro Ala Pro
450                 455                 460
```

-continued

| | | |
|---|---|---|
| gca gcc ccc gcc cag ccc gga gcc acc ctc gcc ccg acc cct ccc<br>Ala Ala Pro Ala Gln Pro Gly Ala Thr Leu Ala Pro Pro Thr Pro Pro<br>465                                 470                            475                            480 | | 1440 |
| cgc ccc cgg gac ggg ggg acc ccc agg cac tcc cgg gcc ctg agc tgg<br>Arg Pro Arg Asp Gly Gly Thr Pro Arg His Ser Arg Ala Leu Ser Trp<br>                         485                         490                          495 | | 1488 |
| gcc gcc agg gcc gcc cgc cct ttg ccg ctc ttc ttg ggc cga gct ccg<br>Ala Ala Arg Ala Ala Arg Pro Leu Pro Leu Phe Leu Gly Arg Ala Pro<br>        500                         505                       510 | | 1536 |
| ccc ccg cgc cct gca gtg gag cag ccg ccc cca aag gtg tac gtg acc<br>Pro Pro Arg Pro Ala Val Glu Gln Pro Pro Pro Lys Val Tyr Val Thr<br>515                            520                         525 | | 1584 |
| agg gtg cgg ccg gga cag cgg gca tcc ccc cgg gcc ccg gcg ccg cgt<br>Arg Val Arg Pro Gly Gln Arg Ala Ser Pro Arg Ala Pro Ala Pro Arg<br>             530                        535                       540 | | 1632 |
| gcg ccc tgg ccg ccc ttc cct ggc gtc ttc ctg cac ccc agg cct ctg<br>Ala Pro Trp Pro Pro Phe Pro Gly Val Phe Leu His Pro Arg Pro Leu<br>545                               550                           555                         560 | | 1680 |
| ccc aga gtg cag ctg cgg gcg ccc cca cgc cca ccc cgg ccc cac ggc<br>Pro Arg Val Gln Leu Arg Ala Pro Pro Arg Pro Pro Arg Pro His Gly<br>                   565                        570                       575 | | 1728 |
| cgc agg acc ggc ggc ccc cag gcc aca cag ccg agg ccc cca gcc cgg<br>Arg Arg Thr Gly Gly Pro Gln Ala Thr Gln Pro Arg Pro Pro Ala Arg<br>            580                         585                       590 | | 1776 |
| gcg cag gcc acc caa ggg ggc cgg gag ggc cag gcg cgc acg ctg gga<br>Ala Gln Ala Thr Gln Gly Gly Arg Glu Gly Gln Ala Arg Thr Leu Gly<br>                  595                        600                       605 | | 1824 |
| cct gcg gcg ccc aca gtg gac tca aac ttg tcc tcc gaa gcg cgg ccc<br>Pro Ala Ala Pro Thr Val Asp Ser Asn Leu Ser Ser Glu Ala Arg Pro<br>610                                 615                            620 | | 1872 |
| gtg acc tcc ttc ctg agc ttg tcc cag gtg tcc ggg ccg cag ctg ccc<br>Val Thr Ser Phe Leu Ser Leu Ser Gln Val Ser Gly Pro Gln Leu Pro<br>625                                 630                          635                       640 | | 1920 |
| ggg gag ggc gaa gag gag gag gaa ggg gag gac gat ggg gcc ccg ggc<br>Gly Glu Gly Glu Glu Glu Glu Gly Glu Asp Asp Gly Ala Pro Gly<br>                         645                         650                       655 | | 1968 |
| gac gag gcc gcg tcg gag gac agc gag gag gcc gcg ggc ccg gcg ctc<br>Asp Glu Ala Ala Ser Glu Asp Ser Glu Glu Ala Ala Gly Pro Ala Leu<br>        660                         665                       670 | | 2016 |
| gga cgc tgg cgt gag gac gcc atc gac tgg cag cgc acg ttc agc gtg<br>Gly Arg Trp Arg Glu Asp Ala Ile Asp Trp Gln Arg Thr Phe Ser Val<br>             675                        680                       685 | | 2064 |
| ggc gcc gtg gac ttc gag ctg ctg cgc tcg gac tgg aac gac ctg cga<br>Gly Ala Val Asp Phe Glu Leu Leu Arg Ser Asp Trp Asn Asp Leu Arg<br>690                                 695                            700 | | 2112 |
| tgc aac gtt tcg ggg aac ctg cag ctg ccg gag gcg gag gcc gtg gac<br>Cys Asn Val Ser Gly Asn Leu Gln Leu Pro Glu Ala Glu Ala Val Asp<br>705                                 710                          715                       720 | | 2160 |
| gtg acc gct cag tac atg gag cgg ctg aac gcg cgc cac ggc ggg cgc<br>Val Thr Ala Gln Tyr Met Glu Arg Leu Asn Ala Arg His Gly Gly Arg<br>                         725                         730                       735 | | 2208 |
| ttc gcg ctt ctg cgc atc gtg aac gtg gag aag cgc cgg gac tcg gcg<br>Phe Ala Leu Leu Arg Ile Val Asn Val Glu Lys Arg Arg Asp Ser Ala<br>            740                        745                       750 | | 2256 |
| cga ggg agt cgc ttc ctg ctg gag ctg gag ctg cag gag cgc ggg ggc<br>Arg Gly Ser Arg Phe Leu Leu Glu Leu Glu Leu Gln Glu Arg Gly Gly<br>                 755                        760                       765 | | 2304 |
| ggc cgc ctg cga ctg tcc gag tac gtc ttc ctg cgg ctg ccg gga gcc<br>Gly Arg Leu Arg Leu Ser Glu Tyr Val Phe Leu Arg Leu Pro Gly Ala | | 2352 |

-continued

```
                  770                 775                 780
cgc gta ggg gat gca gac gga gaa agt ccc gaa ccc gct ccc gcc gcc      2400
Arg Val Gly Asp Ala Asp Gly Glu Ser Pro Glu Pro Ala Pro Ala Ala
785                 790                 795                 800 tcc gtg cgc ccc gac ggc cgc ccc gag ctc tgc cgg cca ctg cgc ctg      2448
Ser Val Arg Pro Asp Gly Arg Pro Glu Leu Cys Arg Pro Leu Arg Leu
                805                 810                 815 gcc tgg cgc cag gac gtg atg gtt cac ttc atc gtg cca gtg aaa aac      2496
Ala Trp Arg Gln Asp Val Met Val His Phe Ile Val Pro Val Lys Asn
            820                 825                 830 cag gca cgg tgg gtg gca cag ttc ctg gcg gac atg gct gcg ctg cac      2544
Gln Ala Arg Trp Val Ala Gln Phe Leu Ala Asp Met Ala Ala Leu His
        835                 840                 845 gcg cgc acc ggg gac tcg cgt ttc agc gtc gtc ctg gtg gat ttc gag      2592
Ala Arg Thr Gly Asp Ser Arg Phe Ser Val Val Leu Val Asp Phe Glu
    850                 855                 860 agc gag gat atg gac gtg gag cgg gcc ctg cgc gcc gcg cgc ctg ccc      2640
Ser Glu Asp Met Asp Val Glu Arg Ala Leu Arg Ala Ala Arg Leu Pro
865                 870                 875                 880 cgg tac cag tac ctg aga cga acc ggg aac ttc gag cgc tcc gcc ggg      2688
Arg Tyr Gln Tyr Leu Arg Arg Thr Gly Asn Phe Glu Arg Ser Ala Gly
                885                 890                 895 ctg cag gcg gga gtg gac gcg gta gag gac gcc agc agc atc gtg ttc      2736
Leu Gln Ala Gly Val Asp Ala Val Glu Asp Ala Ser Ser Ile Val Phe
            900                 905                 910 ctc tgc gac ctg cac atc cac ttc cca ccc aac atc ctg gac ggc atc      2784
Leu Cys Asp Leu His Ile His Phe Pro Pro Asn Ile Leu Asp Gly Ile
        915                 920                 925 cgc aag cac tgc gtg gag ggc agg ctg gcc ttc gcg ccc gtg gtc atg      2832
Arg Lys His Cys Val Glu Gly Arg Leu Ala Phe Ala Pro Val Val Met
    930                 935                 940 cgc ctg agc tgc ggg agc tcg ccc cgg gac ccc cac ggt tac tgg gag      2880
Arg Leu Ser Cys Gly Ser Ser Pro Arg Asp Pro His Gly Tyr Trp Glu
945                 950                 955                 960 gtg aac ggc ttt ggc ctt ttt ggg atc tac aag tcg gac ttt gac cgg      2928
Val Asn Gly Phe Gly Leu Phe Gly Ile Tyr Lys Ser Asp Phe Asp Arg
                965                 970                 975 gtt gga gga atg aac acg gag gag ttc cga gac cag tgg ggg ggt gaa      2976
Val Gly Gly Met Asn Thr Glu Glu Phe Arg Asp Gln Trp Gly Gly Glu
            980                 985                 990 gac tgg gag ctc ctg gac agg gtc ctg cag gca ggg ctg gag gtg gag      3024
Asp Trp Glu Leu Leu Asp Arg Val Leu Gln Ala Gly Leu Glu Val Glu
        995                 1000                1005 cgg ctc cga ctg cgg aat ttc tat cac cac tac cac tcc aag agg ggc      3072
Arg Leu Arg Leu Arg Asn Phe Tyr His His Tyr His Ser Lys Arg Gly
    1010                1015                1020 atg tgg agc gtc cgc agc agg aag ggc tct cgc acg ggg gcg tct tga      3120
Met Trp Ser Val Arg Ser Arg Lys Gly Ser Arg Thr Gly Ala Ser
1025                1030                1035            1039

<210> SEQ ID NO 3
<211> LENGTH: 998
<212> TYPE: PRT
<213> ORGANISM: Homo sapiens

<400> SEQUENCE: 3

Met Gly Ser Pro Arg Ala Ala Arg Pro Pro Leu Leu Leu Arg Pro Val
1               5                   10                  15

Lys Leu Leu Arg Arg Arg Phe Arg Leu Leu Leu Ala Leu Ala Val Val
            20                  25                  30
```

```
Ser Val Gly Leu Trp Thr Leu Tyr Leu Glu Leu Val Ala Ser Ala Gln
         35                  40                  45

Val Gly Gly Asn Pro Leu Asn Arg Arg Tyr Gly Ser Trp Arg Glu Leu
         50                  55                  60

Ala Lys Ala Leu Ala Ser Arg Asn Ile Pro Ala Val Asp Pro His Leu
 65                  70                  75                  80

Gln Phe Tyr His Pro Gln Arg Leu Ser Leu Glu Asp His Asp Ile Asp
                 85                  90                  95

Gln Gly Val Ser Ser Asn Ser Ser Tyr Leu Lys Trp Asn Lys Pro Val
            100                 105                 110

Pro Trp Leu Ser Glu Phe Arg Gly Arg Ala Asn Leu His Val Phe Glu
            115                 120                 125

Asp Trp Cys Gly Ser Ser Ile Gln Gln Leu Arg Arg Asn Leu His Phe
            130                 135                 140

Pro Leu Tyr Pro His Ile Arg Thr Thr Leu Arg Lys Leu Ala Val Ser
145                 150                 155                 160

Pro Lys Trp Thr Asn Tyr Gly Leu Arg Ile Phe Gly Tyr Leu His Pro
                165                 170                 175

Phe Thr Asp Gly Lys Ile Gln Phe Ala Ile Ala Asp Asp Asn Ala
                180                 185                 190

Glu Phe Trp Leu Ser Leu Asp Asp Gln Val Ser Gly Leu Gln Leu Leu
            195                 200                 205

Ala Ser Val Gly Lys Thr Gly Lys Glu Trp Thr Ala Pro Gly Glu Phe
210                 215                 220

Gly Lys Phe Arg Ser Gln Ile Ser Lys Pro Val Ser Leu Ser Ala Ser
225                 230                 235                 240

His Arg Tyr Tyr Phe Glu Val Leu His Lys Gln Asn Glu Glu Gly Thr
                245                 250                 255

Asp His Val Glu Val Ala Trp Arg Arg Asn Asp Pro Gly Ala Lys Phe
            260                 265                 270

Thr Ile Ile Asp Ser Leu Ser Leu Ser Leu Phe Thr Asn Glu Thr Phe
            275                 280                 285

Leu Gln Met Asp Glu Val Gly His Ile Pro Gln Thr Ala Ala Ser His
            290                 295                 300

Val Asp Ser Ser Asn Ala Leu Pro Arg Asp Gln Pro Pro Ala Asp
305                 310                 315                 320

Met Leu Arg Pro Asp Pro Arg Asp Thr Leu Tyr Arg Val Pro Leu Ile
                325                 330                 335

Pro Lys Ser His Leu Arg His Val Leu Pro Asp Cys Pro Tyr Lys Pro
            340                 345                 350

Ser Tyr Leu Val Asp Gly Leu Pro Leu Gln Arg Tyr Gln Gly Leu Arg
            355                 360                 365

Phe Val His Leu Ser Phe Val Tyr Pro Asn Asp Tyr Thr Arg Leu Ser
            370                 375                 380

His Met Glu Thr His Asn Lys Cys Phe Tyr Gln Glu Asn Ala Tyr Tyr
385                 390                 395                 400

Gln Asp Arg Phe Ser Phe Gln Glu Tyr Ile Arg Ile Asp Gln Pro Glu
                405                 410                 415

Lys Gln Gly Leu Glu Gln Pro Gly Phe Glu Glu Asn Leu Leu Glu Glu
            420                 425                 430

Ser Gln Tyr Gly Glu Val Ala Glu Glu Thr Pro Ala Ser Asn Asn Gln
            435                 440                 445
```

```
Asn Ala Arg Met Leu Glu Gly Arg Gln Thr Pro Ala Ser Thr Leu Glu
    450                 455                 460

Gln Asp Ala Thr Asp Tyr Arg Leu Arg Ser Leu Arg Lys Leu Leu Ala
465                 470                 475                 480

Gln Pro Arg Glu Gly Leu Leu Ala Pro Phe Ser Lys Arg Asn Ser Thr
                485                 490                 495

Ala Ser Phe Pro Gly Arg Thr Ser His Ile Pro Val Gln Gln Pro Glu
            500                 505                 510

Lys Arg Lys Gln Lys Pro Ser Pro Glu Pro Ser Gln Asp Ser Pro His
        515                 520                 525

Ser Asp Lys Trp Pro Pro Gly His Pro Val Lys Asn Leu Pro Gln Met
    530                 535                 540

Arg Gly Pro Arg Pro Arg Pro Ala Gly Asp Ser Pro Arg Lys Thr Gln
545                 550                 555                 560

Trp Leu Asn Gln Val Glu Ser Tyr Ile Ala Glu Gln Arg Arg Gly Asp
                565                 570                 575

Arg Met Arg Pro Gln Ala Pro Gly Arg Gly Trp His Gly Glu Glu Glu
            580                 585                 590

Val Val Ala Ala Ala Gly Gln Glu Gly Gln Val Glu Gly Glu Glu Glu
        595                 600                 605

Gly Glu Glu Glu Glu Glu Glu Asp Met Ser Glu Val Phe Glu Tyr
    610                 615                 620

Val Pro Val Phe Asp Pro Val Val Asn Trp Asp Gln Thr Phe Ser Ala
625                 630                 635                 640

Arg Asn Leu Asp Phe Gln Ala Leu Arg Thr Asp Trp Ile Asp Leu Ser
                645                 650                 655

Cys Asn Thr Ser Gly Asn Leu Leu Pro Glu Gln Glu Ala Leu Glu
            660                 665                 670

Val Thr Arg Val Phe Leu Lys Lys Leu Asn Gln Arg Ser Arg Gly Arg
        675                 680                 685

Tyr Gln Leu Gln Arg Ile Val Asn Val Glu Lys Arg Gln Asp Gln Leu
    690                 695                 700

Arg Gly Gly Arg Tyr Leu Leu Glu Leu Glu Leu Glu Gln Gly Gln
705                 710                 715                 720

Arg Val Val Arg Leu Ser Glu Tyr Val Ser Ala Arg Gly Trp Gln Gly
                725                 730                 735

Ile Asp Pro Ala Gly Gly Glu Val Glu Ala Arg Asn Leu Gln Gly
            740                 745                 750

Leu Val Trp Asp Pro His Asn Arg Arg Gln Val Leu Asn Thr Arg
        755                 760                 765

Ala Gln Glu Pro Lys Leu Cys Trp Pro Gln Gly Phe Ser Trp Ser His
    770                 775                 780

Arg Ala Val Val His Phe Val Pro Val Lys Asn Gln Ala Arg Trp
785                 790                 795                 800

Val Gln Gln Phe Ile Lys Asp Met Glu Asn Leu Phe Gln Val Thr Gly
                805                 810                 815

Asp Pro His Phe Asn Ile Val Ile Thr Asp Tyr Ser Glu Asp Met
            820                 825                 830

Asp Val Glu Met Ala Leu Lys Arg Ser Lys Leu Arg Ser Tyr Gln Tyr
        835                 840                 845

Val Lys Leu Ser Gly Asn Phe Glu Arg Ser Ala Gly Leu Gln Ala Gly
    850                 855                 860

Ile Asp Leu Val Lys Asp Pro His Ser Ile Ile Phe Leu Cys Asp Leu
```

```
                865                 870                 875                 880
            His Ile His Phe Pro Ala Gly Val Ile Asp Ala Ile Arg Lys His Cys
                            885                 890                 895

Val Glu Gly Lys Met Ala Phe Ala Pro Met Val Met Arg Leu His Cys
                            900                 905                 910

Gly Ala Thr Pro Gln Trp Pro Glu Gly Tyr Trp Glu Val Asn Gly Phe
                            915                 920                 925

Gly Leu Leu Gly Ile Tyr Lys Ser Asp Leu Asp Arg Ile Gly Gly Met
                            930                 935                 940

Asn Thr Lys Glu Phe Arg Asp Arg Trp Gly Glu Asp Trp Glu Leu
            945                 950                 955                 960

Leu Asp Arg Ile Leu Gln Ala Gly Leu Asp Val Glu Arg Leu Ser Leu
                            965                 970                 975

Arg Asn Phe Phe His His Phe His Ser Lys Arg Gly Met Trp Ser Arg
                            980                 985                 990

Arg Gln Met Lys Thr Leu
                            995         998

<210> SEQ ID NO 4
<211> LENGTH: 2997
<212> TYPE: DNA
<213> ORGANISM: Homo sapiens

<400> SEQUENCE: 4 atg ggg agc ccc cgg gcc gcg cgg ccc ccg ctg ctc ctg cgc ccg gtg        48
Met Gly Ser Pro Arg Ala Ala Arg Pro Pro Leu Leu Leu Arg Pro Val
 1               5                  10                  15 aag ctg ctg cgg agg cgc ttc cgg ctg ctg ctg gcg ctc gcc gtg gtg        96
Lys Leu Leu Arg Arg Arg Phe Arg Leu Leu Leu Ala Leu Ala Val Val
                20                  25                  30 tct gtg ggg ctc tgg act ctg tat ctg gaa ctg gtg gcg tcg gcc cag       144
Ser Val Gly Leu Trp Thr Leu Tyr Leu Glu Leu Val Ala Ser Ala Gln
            35                  40                  45 gtc ggc ggg aac ccc ctg aac cgg agg tac ggc agc tgg aga gaa cta       192
Val Gly Gly Asn Pro Leu Asn Arg Arg Tyr Gly Ser Trp Arg Glu Leu
        50                  55                  60 gcc aag gct ctg gcc agc agg aac att cca gct gtg gat cca cac ctc       240
Ala Lys Ala Leu Ala Ser Arg Asn Ile Pro Ala Val Asp Pro His Leu
 65                  70                  75                  80 cag ttc tac cat ccc cag agg ctg agc ctc gag gac cac gac att gac       288
Gln Phe Tyr His Pro Gln Arg Leu Ser Leu Glu Asp His Asp Ile Asp
                85                  90                  95 caa ggg gtg agc agt aac agc agc tac ttg aag tgg aac aag cct gtc       336
Gln Gly Val Ser Ser Asn Ser Ser Tyr Leu Lys Trp Asn Lys Pro Val
            100                 105                 110 ccc tgg ctc tca gag ttc cgg ggc cgt gcc aac ctg cat gtg ttt gaa       384
Pro Trp Leu Ser Glu Phe Arg Gly Arg Ala Asn Leu His Val Phe Glu
        115                 120                 125 gac tgg tgt ggc agc tct atc cag cag ctc agg agg aac ctg cat ttc       432
Asp Trp Cys Gly Ser Ser Ile Gln Gln Leu Arg Arg Asn Leu His Phe
    130                 135                 140 cca ctg tac ccc cat att cgc aca acc ctg agg aag ctt gct gtg tcc       480
Pro Leu Tyr Pro His Ile Arg Thr Thr Leu Arg Lys Leu Ala Val Ser
145                 150                 155                 160 ccc aaa tgg acc aac tat ggc ctc cgc atc ttt ggc tac ctg cac ccc       528
Pro Lys Trp Thr Asn Tyr Gly Leu Arg Ile Phe Gly Tyr Leu His Pro
                165                 170                 175 ttt act gat ggg aaa atc cag ttt gcc att gct gca gat gac aac gcg       576
```

```
            Phe Thr Asp Gly Lys Ile Gln Phe Ala Ile Ala Ala Asp Asp Asn Ala
                        180                 185                 190 gag ttc tgg ctg agc ctc gat gac cag gtc tca ggc ctc cag ctg ctg        624
Glu Phe Trp Leu Ser Leu Asp Asp Gln Val Ser Gly Leu Gln Leu Leu
            195                 200                 205 gcc agt gtg ggc aag act gga aag gag tgg acc gcc ccg gga gag ttt        672
Ala Ser Val Gly Lys Thr Gly Lys Glu Trp Thr Ala Pro Gly Glu Phe
        210                 215                 220 ggg aaa ttt cgg agc caa att tcc aag ccg gtg agc ctg tca gcc tcc        720
Gly Lys Phe Arg Ser Gln Ile Ser Lys Pro Val Ser Leu Ser Ala Ser
225                 230                 235                 240 cac agg tac tac ttc gag gtg ctg cac aag cag aat gag gag ggc acc        768
His Arg Tyr Tyr Phe Glu Val Leu His Lys Gln Asn Glu Glu Gly Thr
                245                 250                 255 gac cac gtg gaa gtt gca tgg cga cgg aac gac cct gga gcc aag ttc        816
Asp His Val Glu Val Ala Trp Arg Arg Asn Asp Pro Gly Ala Lys Phe
            260                 265                 270 acc atc att gac tcc ctc tcc ctg tcc ctc ttc aca aat gag acg ttc        864
Thr Ile Ile Asp Ser Leu Ser Leu Ser Leu Phe Thr Asn Glu Thr Phe
        275                 280                 285 cta cag atg gat gag gtg ggc cac atc cca cag aca gca gcc agc cac        912
Leu Gln Met Asp Glu Val Gly His Ile Pro Gln Thr Ala Ala Ser His
    290                 295                 300 gtg gac tcc tcc aac gct ctt ccc agg gat gag cag ccg ccc gct gac        960
Val Asp Ser Ser Asn Ala Leu Pro Arg Asp Glu Gln Pro Pro Ala Asp
305                 310                 315                 320 atg ctt cgg cct gac ccc cgg gac acc ctc tat cga gtg cct ctg atc       1008
Met Leu Arg Pro Asp Pro Arg Asp Thr Leu Tyr Arg Val Pro Leu Ile
                325                 330                 335 ccc aag tcg cat ctc cgc cac gtc ctg cct gac tgt ccc tac aaa ccc       1056
Pro Lys Ser His Leu Arg His Val Leu Pro Asp Cys Pro Tyr Lys Pro
            340                 345                 350 agc tat ctg gtg gat ggg ctt cct ctg cag cgc tac cag gga ctc cgg       1104
Ser Tyr Leu Val Asp Gly Leu Pro Leu Gln Arg Tyr Gln Gly Leu Arg
        355                 360                 365 ttt gtt cat ctg tct ttt gtt tac ccc aat gac tat acc cgc ctg agc       1152
Phe Val His Leu Ser Phe Val Tyr Pro Asn Asp Tyr Thr Arg Leu Ser
    370                 375                 380 cac atg gag acc cac aat aaa tgt ttc tac cag gaa aac gcc tac tac       1200
His Met Glu Thr His Asn Lys Cys Phe Tyr Gln Glu Asn Ala Tyr Tyr
385                 390                 395                 400 caa gac cgg ttc agc ttt cag gag tac atc agg att gac cag cct gag       1248
Gln Asp Arg Phe Ser Phe Gln Glu Tyr Ile Arg Ile Asp Gln Pro Glu
                405                 410                 415 aag cag ggg ctg gag cag cca ggt ttt gag gaa aac ctt cta gaa gag       1296
Lys Gln Gly Leu Glu Gln Pro Gly Phe Glu Glu Asn Leu Leu Glu Glu
            420                 425                 430 tcc cag tat ggg gaa gtg gca gag gag acc cct gcc tcc aac aac cag       1344
Ser Gln Tyr Gly Glu Val Ala Glu Glu Thr Pro Ala Ser Asn Asn Gln
        435                 440                 445 aat gcc agg atg ctt gag gga aga cag aca cct gcc tcc acc ctg gag       1392
Asn Ala Arg Met Leu Glu Gly Arg Gln Thr Pro Ala Ser Thr Leu Glu
    450                 455                 460 caa gat gcc act gac tac cgc ctc cga agc ctg cgg aaa ctc ctg gct       1440
Gln Asp Ala Thr Asp Tyr Arg Leu Arg Ser Leu Arg Lys Leu Leu Ala
465                 470                 475                 480 cag ccc cgg gag ggc ctg ctg gcc ccc ttc tcc aag cgg aac tcc aca       1488
Gln Pro Arg Glu Gly Leu Leu Ala Pro Phe Ser Lys Arg Asn Ser Thr
                485                 490                 495
```

-continued

```
gcg tcc ttc cca ggg agg acc agc cac att cca gtg cag cag cca gag      1536
Ala Ser Phe Pro Gly Arg Thr Ser His Ile Pro Val Gln Gln Pro Glu
            500                 505                 510 aag agg aag caa aaa ccc agc cct gag ccc agc caa gat tca cct cat      1584
Lys Arg Lys Gln Lys Pro Ser Pro Glu Pro Ser Gln Asp Ser Pro His
        515                 520                 525 tcc gac aag tgg cct cct ggg cac cct gtg aag aac ctg cct cag atg      1632
Ser Asp Lys Trp Pro Pro Gly His Pro Val Lys Asn Leu Pro Gln Met
530                 535                 540 agg ggg ccc agg ccc agg ccc gct ggt gac agc ccc agg aag act cag      1680
Arg Gly Pro Arg Pro Arg Pro Ala Gly Asp Ser Pro Arg Lys Thr Gln
545                 550                 555                 560 tgg ctg aac cag gtg gag tcg tac atc gca gag cag aga cgg ggt gac      1728
Trp Leu Asn Gln Val Glu Ser Tyr Ile Ala Glu Gln Arg Arg Gly Asp
            565                 570                 575 agg atg cgg cct cag gcc ccc gga agg ggc tgg cat ggg gag gag gaa      1776
Arg Met Arg Pro Gln Ala Pro Gly Arg Gly Trp His Gly Glu Glu Glu
        580                 585                 590 gtg gtg gcg gcc gca ggc cag gaa gga caa gtg gag gga gag gaa gag      1824
Val Val Ala Ala Ala Gly Gln Glu Gly Gln Val Glu Gly Glu Glu Glu
    595                 600                 605 ggg gaa gaa gag gag gag gaa gag gat atg agt gag gtg ttc gag tac      1872
Gly Glu Glu Glu Glu Glu Glu Asp Met Ser Glu Val Phe Glu Tyr
610                 615                 620 gta cct gtg ttt gac ccg gta gta aac tgg gac cag acc ttc agt gcc      1920
Val Pro Val Phe Asp Pro Val Val Asn Trp Asp Gln Thr Phe Ser Ala
625                 630                 635                 640 cgg aat ctc gac ttc caa gcc ctg agg act gac tgg atc gat ctg agc      1968
Arg Asn Leu Asp Phe Gln Ala Leu Arg Thr Asp Trp Ile Asp Leu Ser
            645                 650                 655 tgt aac aca tct ggc aac ctg ctg ctt cca gag cag gaa gct ctg gag      2016
Cys Asn Thr Ser Gly Asn Leu Leu Leu Pro Glu Gln Glu Ala Leu Glu
        660                 665                 670 gtc acg cga gtc ttc ttg aag aag ctc aac cag agg agc cgg ggg agg      2064
Val Thr Arg Val Phe Leu Lys Lys Leu Asn Gln Arg Ser Arg Gly Arg
    675                 680                 685 tac cag cta cag cgc att gtg aac gtg gaa aag cgt cag gac cag cta      2112
Tyr Gln Leu Gln Arg Ile Val Asn Val Glu Lys Arg Gln Asp Gln Leu
690                 695                 700 cgt ggg ggt cgc tac ctc ctg gag ctt gaa ctg ttg gaa caa ggc cag      2160
Arg Gly Gly Arg Tyr Leu Leu Glu Leu Glu Leu Leu Glu Gln Gly Gln
705                 710                 715                 720 cgc gtg gtg cgg ctc tcg gag tat gtg tct gca cga ggc tgg cag ggc      2208
Arg Val Val Arg Leu Ser Glu Tyr Val Ser Ala Arg Gly Trp Gln Gly
            725                 730                 735 atc gat cca gct ggt ggg gag gag gtc gag gcc cgg aac ctg caa ggc      2256
Ile Asp Pro Ala Gly Gly Glu Glu Val Glu Ala Arg Asn Leu Gln Gly
        740                 745                 750 ctg gtc tgg gac cca cac aac cgt agg aga cag gtc ctg aat acc cgg      2304
Leu Val Trp Asp Pro His Asn Arg Arg Arg Gln Val Leu Asn Thr Arg
    755                 760                 765 gcc caa gag ccc aag ctg tgc tgg cct cag ggt ttc tcc tgg agt cac      2352
Ala Gln Glu Pro Lys Leu Cys Trp Pro Gln Gly Phe Ser Trp Ser His
770                 775                 780 cga gcc gtg gtc cac ttc gtc gtg cct gtg aag aac cag gca cgc tgg      2400
Arg Ala Val Val His Phe Val Val Pro Val Lys Asn Gln Ala Arg Trp
785                 790                 795                 800 gta cag caa ttc atc aaa gac atg gaa aac ctg ttc cag gtc acc ggt      2448
Val Gln Gln Phe Ile Lys Asp Met Glu Asn Leu Phe Gln Val Thr Gly
            805                 810                 815
```

```
gac cca cac ttc aac atc gtc atc act gac tat agc agt gag gac atg    2496
Asp Pro His Phe Asn Ile Val Ile Thr Asp Tyr Ser Ser Glu Asp Met
            820                 825                 830 gat gtt gag atg gca ctg aag agg tcc aag ctg cgg agc tac cag tac    2544
Asp Val Glu Met Ala Leu Lys Arg Ser Lys Leu Arg Ser Tyr Gln Tyr
        835                 840                 845 gtg aag cta agt gga aac ttt gaa cgc tca gct gga ctt cag gct ggc    2592
Val Lys Leu Ser Gly Asn Phe Glu Arg Ser Ala Gly Leu Gln Ala Gly
    850                 855                 860 ata gac ctc gtg aag gac ccg cac agc atc atc ttc ctc tgt gac ctc    2640
Ile Asp Leu Val Lys Asp Pro His Ser Ile Ile Phe Leu Cys Asp Leu
865                 870                 875                 880 cac atc cac ttc cca gct gga gtc atc gat gcc att cgg aag cac tgt    2688
His Ile His Phe Pro Ala Gly Val Ile Asp Ala Ile Arg Lys His Cys
                885                 890                 895 gtg gag gga aag atg gcc ttt gcc ccc atg gtg atg agg ctg cat tgt    2736
Val Glu Gly Lys Met Ala Phe Ala Pro Met Val Met Arg Leu His Cys
            900                 905                 910 ggg gcc acc ccc cag tgg cct gag ggc tac tgg gag gtg aat ggg ttc    2784
Gly Ala Thr Pro Gln Trp Pro Glu Gly Tyr Trp Glu Val Asn Gly Phe
        915                 920                 925 ggg ctg ctt ggc atc tac aag tct gac ctg gac agg att ggg ggc atg    2832
Gly Leu Leu Gly Ile Tyr Lys Ser Asp Leu Asp Arg Ile Gly Gly Met
    930                 935                 940 aac acc aag gag ttc cga gac cgc tgg ggc ggg gaa gac tgg gag ctg    2880
Asn Thr Lys Glu Phe Arg Asp Arg Trp Gly Gly Glu Asp Trp Glu Leu
945                 950                 955                 960 ctg gac agg ata ctc caa gcg ggc ctg gac gtg gag cgt ctc tcc ctc    2928
Leu Asp Arg Ile Leu Gln Ala Gly Leu Asp Val Glu Arg Leu Ser Leu
                965                 970                 975 agg aat ttc ttc cat cat ttc cat tcc aag cga ggc atg tgg agc cgt    2976
Arg Asn Phe Phe His His Phe His Ser Lys Arg Gly Met Trp Ser Arg
            980                 985                 990 cgc cag atg aag acg ctg tag                                        2997
Arg Gln Met Lys Thr Leu
        995         998

<210> SEQ ID NO 5
<211> LENGTH: 21
<212> TYPE: DNA
<213> ORGANISM: Artificial Sequence
<220> FEATURE:
<223> OTHER INFORMATION: Oligonucleotide primer used in PCR for cloning
      GalNAc-T1 cDNA

<400> SEQUENCE: 5
gctcctgcag ctccagctcc a                                            21

<210> SEQ ID NO 6
<211> LENGTH: 22
<212> TYPE: DNA
<213> ORGANISM: Artificial Sequence
<220> FEATURE:
<223> OTHER INFORMATION: Oligonucleotide primer used in PCR for cloning
      GalNAc-T1 cDNA

<400> SEQUENCE: 6
aagcgactcc ctcgcgccga gt                                           22

<210> SEQ ID NO 7
<211> LENGTH: 24
<212> TYPE: DNA
```

```
<213> ORGANISM: Artificial Sequence
<220> FEATURE:
<223> OTHER INFORMATION: Oligonucleotide primer used in PCR for cloning
      GalNAc-T1 cDNA

<400> SEQUENCE: 7
atgccgcggc tcccggtgaa gaag                                              24

<210> SEQ ID NO 8
<211> LENGTH: 24
<212> TYPE: DNA
<213> ORGANISM: Artificial Sequence
<220> FEATURE:
<223> OTHER INFORMATION: Oligonucleotide primer used in PCR for cloning
      GalNAc-T2 cDNA

<400> SEQUENCE: 8
ccacagttca agctccagga ggta                                              24

<210> SEQ ID NO 9
<211> LENGTH: 24
<212> TYPE: DNA
<213> ORGANISM: Artificial Sequence
<220> FEATURE:
<223> OTHER INFORMATION: Oligonucleotide primer used in PCR for cloning
      GalNAc-T2 cDNA

<400> SEQUENCE: 9
ctgacgcttt tccacgttca caat                                              24

<210> SEQ ID NO 10
<211> LENGTH: 22
<212> TYPE: DNA
<213> ORGANISM: Artificial Sequence
<220> FEATURE:
<223> OTHER INFORMATION: Oligonucleotide primer used in PCR for cloning
      GalNAc-T2 cDNA

<400> SEQUENCE: 10
caccccgtct ctgctctgcg at                                                22

<210> SEQ ID NO 11
<211> LENGTH: 21
<212> TYPE: DNA
<213> ORGANISM: Artificial Sequence
<220> FEATURE:
<223> OTHER INFORMATION: Oligonucleotide primer used in PCR for cloning
      GalNAc-T2 cDNA

<400> SEQUENCE: 11
gtcttcctgg ggctgtcacc a                                                 21

<210> SEQ ID NO 12
<211> LENGTH: 24
<212> TYPE: DNA
<213> ORGANISM: Artificial Sequence
<220> FEATURE:
<223> OTHER INFORMATION: Oligonucleotide primer used in PCR for cloning
      GalNAc-T2 cDNA

<400> SEQUENCE: 12
cacctcatcc atctgtagga acgt                                              24

<210> SEQ ID NO 13
<211> LENGTH: 22
<212> TYPE: DNA
<213> ORGANISM: Artificial Sequence
```

```
<220> FEATURE:
<223> OTHER INFORMATION: Oligonucleotide primer used in PCR for cloning
      GalNAc-T2 cDNA

<400> SEQUENCE: 13
ctgtcgcctg caacttccac gt                                              22

<210> SEQ ID NO 14
<211> LENGTH: 23
<212> TYPE: DNA
<213> ORGANISM: Artificial Sequence
<220> FEATURE:
<223> OTHER INFORMATION: Oligonucleotide primer used in PCR for cloning
      GalNAc-T2 cDNA

<400> SEQUENCE: 14
aatgtcgtgg tcctcgaggc tca                                             23

<210> SEQ ID NO 15
<211> LENGTH: 24
<212> TYPE: DNA
<213> ORGANISM: Artificial Sequence
<220> FEATURE:
<223> OTHER INFORMATION: Oligonucleotide primer used in PCR for cloning
      GalNAc-T2 cDNA

<400> SEQUENCE: 15
gatggtagaa ctggaggtgt ggat                                            24

<210> SEQ ID NO 16
<211> LENGTH: 31
<212> TYPE: DNA
<213> ORGANISM: Artificial Sequence
<220> FEATURE:
<223> OTHER INFORMATION: Oligonucleotide primer used in PCR for cloning
      GalNAc-T1 cDNA

<400> SEQUENCE: 16
cccaagcttc gggggtcca cgctgcgcca t                                     31

<210> SEQ ID NO 17
<211> LENGTH: 30
<212> TYPE: DNA
<213> ORGANISM: Artificial Sequence
<220> FEATURE:
<223> OTHER INFORMATION: Oligonucleotide primer used in PCR for cloning
      GalNAc-T1 cDNA

<400> SEQUENCE: 17
gctctagact caagacgccc ccgtgcgaga                                      30

<210> SEQ ID NO 18
<211> LENGTH: 29
<212> TYPE: DNA
<213> ORGANISM: Artificial Sequence
<220> FEATURE:
<223> OTHER INFORMATION: Oligonucleotide primer used in PCR for cloning
      GalNAc-T2 cDNA

<400> SEQUENCE: 18
ggaattcgag gtacggcagc tggagagaa                                       29

<210> SEQ ID NO 19
<211> LENGTH: 32
<212> TYPE: DNA
<213> ORGANISM: Artificial Sequence
<220> FEATURE:
```

-continued

```
<223> OTHER INFORMATION: Oligonucleotide primer used in PCR for cloning
      GalNAc-T2 cDNA

<400> SEQUENCE: 19
acgcgtcgac ctacagcgtc ttcatctggc ga                                    32

<210> SEQ ID NO 20
<211> LENGTH: 20
<212> TYPE: DNA
<213> ORGANISM: Artificial Sequence
<220> FEATURE:
<223> OTHER INFORMATION: Oligonucleotide primer used in PCR for
      amplifying GalNAc-T1 cDNA

<400> SEQUENCE: 20
ctggtggatt tcgagagcga                                                  20

<210> SEQ ID NO 21
<211> LENGTH: 18
<212> TYPE: DNA
<213> ORGANISM: Artificial Sequence
<220> FEATURE:
<223> OTHER INFORMATION: Oligonucleotide primer used in PCR for
      amplifying GalNAc-T1 cDNA

<400> SEQUENCE: 21
tgccgtccag gatgttgg                                                    18

<210> SEQ ID NO 22
<211> LENGTH: 15
<212> TYPE: DNA
<213> ORGANISM: Artificial Sequence
<220> FEATURE:
<223> OTHER INFORMATION: Oligonucleotide probe used in PCR for detecting
      GalNAc-T1 cDNA

<400> SEQUENCE: 22
gcggtagagg acgcc                                                       15

<210> SEQ ID NO 23
<211> LENGTH: 26
<212> TYPE: DNA
<213> ORGANISM: Artificial Sequence
<220> FEATURE:
<223> OTHER INFORMATION: Oligonucleotide primer used in PCR for
      amplifying GalNAc-T2 cDNA

<400> SEQUENCE: 23
atcgtcatca ctgactatag cagtga                                           26

<210> SEQ ID NO 24
<211> LENGTH: 21
<212> TYPE: DNA
<213> ORGANISM: Artificial Sequence
<220> FEATURE:
<223> OTHER INFORMATION: Oligonucleotide primer used in PCR for
      amplifying GalNAc-T2 cDNA

<400> SEQUENCE: 24
gaatggcatc gatgactcca g                                                21

<210> SEQ ID NO 25
<211> LENGTH: 17
<212> TYPE: DNA
<213> ORGANISM: Artificial Sequence
<220> FEATURE:
<223> OTHER INFORMATION: Oligonucleotide probe used in PCR for detecting
```

GalNAc-T2 cDNA

<400> SEQUENCE: 25
ctcgtgaagg acccgca                17

<210> SEQ ID NO 26
<211> LENGTH: 1034
<212> TYPE: PRT
<213> ORGANISM: Mouse

<400> SEQUENCE: 26

```
Met Pro Trp Phe Pro Val Lys Lys Val Arg Lys Gln Met Lys Leu Leu
 1               5                  10                  15

Leu Leu Leu Leu Leu Leu Thr Cys Ala Ala Trp Leu Thr Tyr Val His
                20                  25                  30

Arg Ser Leu Val Arg Pro Gly Arg Ala Leu Arg Gln Arg Leu Gly Tyr
            35                  40                  45

Gly Arg Asp Gly Glu Lys Leu Thr Gly Val Thr Asp Ser Arg Gly Val
        50                  55                  60

Arg Val Pro Ser Ser Thr Gln Arg Ser Glu Asp Ser Ser Glu Ser His
    65                  70                  75                  80

Glu Glu Glu Gln Ala Pro Gly Arg Gly Pro Asn Met Leu Phe Pro
                85                  90                  95

Gly Gly Pro Arg Lys Pro Pro Leu Asn Leu Thr His Gln Thr Pro
            100                 105                 110

Pro Trp Arg Glu Glu Phe Lys Gly Gln Val Asn Leu His Val Phe Glu
        115                 120                 125

Asp Trp Cys Gly Gly Ala Val Gly His Leu Arg Arg Asn Leu His Phe
    130                 135                 140

Pro Leu Phe Pro His Thr Arg Thr Thr Val Thr Lys Leu Ala Val Ser
145                 150                 155                 160

Pro Lys Trp Lys Asn Tyr Gly Leu Arg Ile Phe Gly Phe Ile His Pro
                165                 170                 175

Ala Arg Asp Gly Asp Ile Gln Phe Ser Val Ala Ser Asp Asn Ser
            180                 185                 190

Glu Phe Trp Leu Ser Leu Asp Glu Ser Pro Ala Ala Gln Leu Val
        195                 200                 205

Ala Phe Val Gly Lys Thr Gly Ser Glu Trp Thr Ala Pro Gly Glu Phe
    210                 215                 220

Thr Lys Phe Ser Ser Gln Val Ser Lys Pro Arg Arg Leu Met Ala Ser
225                 230                 235                 240

Arg Arg Tyr Tyr Phe Glu Leu Leu His Lys Gln Asp Asp Lys Gly Ser
                245                 250                 255

Asp His Val Glu Val Gly Trp Arg Ala Phe Leu Pro Gly Leu Lys Phe
            260                 265                 270

Glu Ile Ile Asp Ser Ala His Ile Ser Leu Tyr Thr Asp Glu Ser Ser
        275                 280                 285

Leu Lys Met Asp His Val Ala His Val Pro Gln Ser Pro Ala Ser His
    290                 295                 300

Ile Gly Gly Phe Pro Pro Gln Gly Glu Pro Ser Ala Asp Met Leu His
305                 310                 315                 320

Pro Asp Pro Arg Asp Thr Phe Phe Leu Thr Pro Arg Met Glu Pro Leu
                325                 330                 335

Ser Leu Glu Asn Val Leu Glu Pro Cys Ala Tyr Ala Pro Thr Tyr Ile
            340                 345                 350
```

-continued

```
Leu Lys Asp Phe Pro Ile Ala Arg Tyr Gln Gly Leu Gln Phe Val Tyr
        355                 360                 365
Leu Ser Phe Ile Tyr Pro Asn Asp His Thr Arg Leu Thr His Met Glu
    370                 375                 380
Thr Asp Asn Lys Cys Phe Tyr Arg Glu Ser Pro Leu Tyr Leu Glu Arg
385                 390                 395                 400
Phe Gly Phe Tyr Lys Tyr Met Lys Met Asp Lys Glu Glu Gly Glu Glu
                405                 410                 415
Asp Glu Glu Glu Glu Val Gln Arg Arg Ala Phe Leu Phe Leu Asn Pro
            420                 425                 430
Asp Asp Phe Leu Asp Glu Glu Asp Glu Gln Asp Leu Leu Asp Ser Leu
        435                 440                 445
Glu Pro Thr Asp Ala Ser Val Gln Gln Ser His Arg Thr Pro Thr Pro
    450                 455                 460
Ala Ala Ser Thr Gly Thr Thr Ala Ser Pro Thr Pro Thr Thr Ser
465                 470                 475                 480
Pro Leu Asp Glu Gln Thr Leu Arg His Ser Arg Ala Leu Asn Trp Ala
                485                 490                 495
Pro Arg Pro Leu Pro Leu Phe Leu Gly Arg Ala Pro Pro Arg Thr
            500                 505                 510
Val Glu Lys Ser Pro Ser Lys Val Tyr Val Thr Arg Val Arg Pro Gly
        515                 520                 525
Gln Arg Ala Ser Pro Arg Ala Leu Arg Asp Ser Pro Trp Pro Pro Phe
    530                 535                 540
Pro Gly Val Phe Leu Arg Pro Lys Pro Leu Pro Arg Val Gln Leu Arg
545                 550                 555                 560
Val Pro Pro His Pro Arg Thr Gln Gly Tyr Arg Thr Ser Gly Pro
                565                 570                 575
Lys Val Thr Glu Leu Lys Pro Pro Val Arg Ala Gln Thr Ser Gln Gly
            580                 585                 590
Gly Arg Glu Gly Gln Leu His Gly Gln Gly Leu Met Val Pro Thr Val
        595                 600                 605
Asp Leu Asn Ser Ser Val Glu Thr Gln Pro Val Thr Ser Phe Leu Ser
    610                 615                 620
Leu Ser Gln Val Ser Arg Pro Gln Leu Pro Gly Glu Gly Glu Glu Gly
625                 630                 635                 640
Glu Glu Asp Gly Ala Pro Gly Asp Glu Ala Thr Ser Glu Asp Ser Glu
                645                 650                 655
Glu Glu Glu Glu Pro Ala Ala Gly Arg Pro Leu Gly Arg Trp Arg Glu
            660                 665                 670
Asp Ala Ile Asn Trp Gln Arg Thr Phe Ser Val Gly Ala Met Asp Phe
        675                 680                 685
Glu Leu Leu Arg Ser Asp Trp Asn Asp Leu Arg Cys Asn Val Ser Gly
    690                 695                 700
Asn Leu Gln Leu Pro Glu Ala Glu Ala Val Asp Val Val Ala Gln Tyr
705                 710                 715                 720
Met Glu Arg Leu Asn Ala Lys His Gly Gly Arg Phe Ser Leu Leu Arg
                725                 730                 735
Ile Val Asn Val Glu Lys Arg Arg Asp Ser Ala Arg Gly Ser Arg Phe
            740                 745                 750
Leu Leu Glu Leu Glu Leu Gln Glu Arg Gly Gly Ser Arg Gln Arg Leu
        755                 760                 765
```

```
Ser Glu Tyr Val Phe Leu Arg Leu Pro Gly Ala Arg Val Gly Asp Glu
    770                 775                 780

Asp Gly Glu Ser Pro Glu Pro Pro Ala Ala Ser Ile His Pro Asp
785                 790                 795                 800

Ser Arg Pro Glu Leu Cys Arg Pro Leu His Leu Ala Trp Arg Gln Asp
            805                 810                 815

Val Met Val His Phe Ile Val Pro Val Lys Asn Gln Ala Arg Trp Val
        820                 825                 830

Val Gln Phe Leu Ala Asp Met Thr Ala Leu His Val His Thr Gly Asp
            835                 840                 845

Ser Tyr Phe Asn Ile Ile Leu Val Asp Phe Glu Ser Glu Asp Met Asp
    850                 855                 860

Val Glu Arg Ala Leu Arg Ala Ala Gln Leu Pro Arg Tyr Gln Tyr Leu
865                 870                 875                 880

Lys Arg Thr Gly Asn Phe Glu Arg Ser Ala Gly Leu Gln Thr Gly Val
                885                 890                 895

Asp Ala Val Glu Asp Pro Ser Ser Ile Val Phe Leu Cys Asp Leu His
            900                 905                 910

Ile His Phe Pro Pro Asn Ile Leu Asp Ser Ile Arg Lys His Cys Val
        915                 920                 925

Glu Gly Lys Leu Ala Phe Ala Pro Val Val Met Arg Leu Gly Cys Gly
    930                 935                 940

Ser Ser Pro Trp Asp Pro His Gly Tyr Trp Glu Val Asn Gly Phe Gly
945                 950                 955                 960

Leu Phe Gly Ile Tyr Lys Ser Asp Phe Asp Arg Val Gly Gly Met Asn
                965                 970                 975

Thr Glu Glu Phe Arg Asp Gln Trp Gly Gly Glu Asp Trp Glu Leu Leu
            980                 985                 990

Asp Arg Val Leu Gln Ala Gly Leu Glu Val Glu Arg Leu Arg Leu Arg
        995                 1000                1005

His Phe Tyr His His Tyr His Ser Lys Arg Gly Met Trp Ala Thr Arg
    1010                1015                1020

Ser Arg Lys Gly Ala Arg Ala Gln Arg Ser
1025                1030

<210> SEQ ID NO 27
<211> LENGTH: 3105
<212> TYPE: DNA
<213> ORGANISM: Mouse

<400> SEQUENCE: 27 atg ccg tgg ttc ccg gtg aag aag gtc cgc aag cag atg aag ctg ctg        48
Met Pro Trp Phe Pro Val Lys Lys Val Arg Lys Gln Met Lys Leu Leu
1               5                   10                  15 ctg ctg ttg ctg ctg ctc acc tgc gcc gcg tgg ctc acg tat gtg cac        96
Leu Leu Leu Leu Leu Leu Thr Cys Ala Ala Trp Leu Thr Tyr Val His
            20                  25                  30 cgg agc ctg gtg cgc ccg ggc cgc gcg cta cgc cag cgg ctg ggc tac       144
Arg Ser Leu Val Arg Pro Gly Arg Ala Leu Arg Gln Arg Leu Gly Tyr
        35                  40                  45 ggg cga gat ggg gag aag ctg acc ggt gtg acc gat agc cgc gga gtc       192
Gly Arg Asp Gly Glu Lys Leu Thr Gly Val Thr Asp Ser Arg Gly Val
    50                  55                  60 cga gtg cca tcg tcc aca cag agg tcg gag gac tcg agt gaa agt cat       240
Arg Val Pro Ser Ser Thr Gln Arg Ser Glu Asp Ser Ser Glu Ser His
65                  70                  75                  80
```

```
gaa gag gag cag gcg ccc gag ggg cgg ggc cca aac atg ctg ttt cct       288
Glu Glu Glu Gln Ala Pro Glu Gly Arg Gly Pro Asn Met Leu Phe Pro
                 85                  90                  95 gga gga cct agg aag cca ccc cca ctg aac ctc acc cac cag aca ccc       336
Gly Gly Pro Arg Lys Pro Pro Pro Leu Asn Leu Thr His Gln Thr Pro
                100                 105                 110 cca tgg cgg gaa gag ttc aaa gga cag gtg aac ctg cac gtg ttt gag       384
Pro Trp Arg Glu Glu Phe Lys Gly Gln Val Asn Leu His Val Phe Glu
            115                 120                 125 gac tgg tgt gga ggt gct gtg ggc cac ctg aga cgg aat ctg cac ttc       432
Asp Trp Cys Gly Gly Ala Val Gly His Leu Arg Arg Asn Leu His Phe
        130                 135                 140 cca ctc ttt cct cac act cgt act acg gtg aca aag tta gct gtg tcc       480
Pro Leu Phe Pro His Thr Arg Thr Thr Val Thr Lys Leu Ala Val Ser
145                 150                 155                 160 cct aag tgg aag aac tat gga ctc cgg att ttt ggc ttc atc cac cca       528
Pro Lys Trp Lys Asn Tyr Gly Leu Arg Ile Phe Gly Phe Ile His Pro
                165                 170                 175 gcc aga gat gga gac atc cag ttc tct gtg gct tcg gat gac aac tct       576
Ala Arg Asp Gly Asp Ile Gln Phe Ser Val Ala Ser Asp Asp Asn Ser
            180                 185                 190 gag ttc tgg ctg agt ttg gat gag agc cca gca gcc gcc cag ctt gta       624
Glu Phe Trp Leu Ser Leu Asp Glu Ser Pro Ala Ala Ala Gln Leu Val
        195                 200                 205 gcc ttt gtg ggc aag act ggc tcc gag tgg acc gca cct gga gaa ttc       672
Ala Phe Val Gly Lys Thr Gly Ser Glu Trp Thr Ala Pro Gly Glu Phe
    210                 215                 220 acc aag ttc agc tcc cag gtg tct aag cca cgt cgg ctc atg gcc tcc       720
Thr Lys Phe Ser Ser Gln Val Ser Lys Pro Arg Arg Leu Met Ala Ser
225                 230                 235                 240 cgg aga tac tac ttt gaa ctg ctc cac aag caa gat gac aag ggt tca       768
Arg Arg Tyr Tyr Phe Glu Leu Leu His Lys Gln Asp Asp Lys Gly Ser
                245                 250                 255 gac cat gtg gaa gtg ggt tgg cga gct ttc ctg cct ggt ctg aag ttc       816
Asp His Val Glu Val Gly Trp Arg Ala Phe Leu Pro Gly Leu Lys Phe
            260                 265                 270 gag atc att gat tct gct cac att tcc ctg tac aca gat gag tca tct       864
Glu Ile Ile Asp Ser Ala His Ile Ser Leu Tyr Thr Asp Glu Ser Ser
        275                 280                 285 ctg aag atg gac cat gtg gcc cat gtg cct cag tct cca gcc agc cac       912
Leu Lys Met Asp His Val Ala His Val Pro Gln Ser Pro Ala Ser His
    290                 295                 300 ata gga gga ttc ccg ccg cag ggg gaa ccc agc gcc gac atg ctg cac       960
Ile Gly Gly Phe Pro Pro Gln Gly Glu Pro Ser Ala Asp Met Leu His
305                 310                 315                 320 cca gac ccc agg gat acc ttc ttc ctc act cct cgg atg gaa cct ttg      1008
Pro Asp Pro Arg Asp Thr Phe Phe Leu Thr Pro Arg Met Glu Pro Leu
                325                 330                 335 agc ctg gag aat gtt ctg gag ccc tgt gcc tat gcc ccc acc tat atc      1056
Ser Leu Glu Asn Val Leu Glu Pro Cys Ala Tyr Ala Pro Thr Tyr Ile
            340                 345                 350 ctc aag gat ttc ccc ata gcc aga tac caa gga cta cag ttt gtg tac      1104
Leu Lys Asp Phe Pro Ile Ala Arg Tyr Gln Gly Leu Gln Phe Val Tyr
        355                 360                 365 ctg tcc ttc atc tac ccc aat gac cat acc cgt ctc act cac atg gag      1152
Leu Ser Phe Ile Tyr Pro Asn Asp His Thr Arg Leu Thr His Met Glu
    370                 375                 380 aca gac aac aag tgc ttc tac cgt gag tcc cca cta tac ctg gaa agg      1200
Thr Asp Asn Lys Cys Phe Tyr Arg Glu Ser Pro Leu Tyr Leu Glu Arg
385                 390                 395                 400
```

```
ttt ggg ttc tat aaa tac atg aaa atg gac aag gag gag gga gag gaa    1248
Phe Gly Phe Tyr Lys Tyr Met Lys Met Asp Lys Glu Glu Gly Glu Glu
                405                 410                 415 gat gag gag gaa gaa gtt cag cgt aga gcc ttc ctc ttc ctc aac cca    1296
Asp Glu Glu Glu Glu Val Gln Arg Arg Ala Phe Leu Phe Leu Asn Pro
            420                 425                 430 gat gac ttc ctg gat gag gag gat gag cag gat ctg tta gac agc ctg    1344
Asp Asp Phe Leu Asp Glu Glu Asp Glu Gln Asp Leu Leu Asp Ser Leu
        435                 440                 445 gag ccc acc gat gca tct gta cag cag agc cac agg acc ccc acc cca    1392
Glu Pro Thr Asp Ala Ser Val Gln Gln Ser His Arg Thr Pro Thr Pro
    450                 455                 460 gca gcc tcc act gga acg aca gcc agc ccg acc cca cct aca act agt    1440
Ala Ala Ser Thr Gly Thr Thr Ala Ser Pro Thr Pro Pro Thr Thr Ser
465                 470                 475                 480 cct ctg gac gag cag acc ctc aga cac tcc cgg gca ctg aat tgg gcc    1488
Pro Leu Asp Glu Gln Thr Leu Arg His Ser Arg Ala Leu Asn Trp Ala
                485                 490                 495 cca cgc ccc ctg ccc ctc ttc ttg ggg cga gct cca cct ccc cga act    1536
Pro Arg Pro Leu Pro Leu Phe Leu Gly Arg Ala Pro Pro Pro Arg Thr
            500                 505                 510 gtg gag aag tcg cct tca aag gtg tac gtg acc agg gtc cga cct gga    1584
Val Glu Lys Ser Pro Ser Lys Val Tyr Val Thr Arg Val Arg Pro Gly
        515                 520                 525 cag cgg gct tcc ccg agg gca ttg cga gac tca ccc tgg cca ccc ttc    1632
Gln Arg Ala Ser Pro Arg Ala Leu Arg Asp Ser Pro Trp Pro Pro Phe
    530                 535                 540 cct ggc gtc ttc ctg cgc ccc aag cct ctg ccc aga gta cag ctg cgg    1680
Pro Gly Val Phe Leu Arg Pro Lys Pro Leu Pro Arg Val Gln Leu Arg
545                 550                 555                 560 gta ccc cca cat cca cct cgg acc cag ggc tat agg acc agt ggc ccc    1728
Val Pro Pro His Pro Pro Arg Thr Gln Gly Tyr Arg Thr Ser Gly Pro
                565                 570                 575 aag gtc aca gaa cta aag ccc cca gtc agg gcc cag acc agc cag gga    1776
Lys Val Thr Glu Leu Lys Pro Pro Val Arg Ala Gln Thr Ser Gln Gly
            580                 585                 590 ggc cgg gag ggc cag tta cat gga cag gga ctc atg gtg ccc aca gtg    1824
Gly Arg Glu Gly Gln Leu His Gly Gln Gly Leu Met Val Pro Thr Val
        595                 600                 605 gac ttg aac tcc tca gtg gaa aca cag cct gtg act tcc ttc ctg agc    1872
Asp Leu Asn Ser Ser Val Glu Thr Gln Pro Val Thr Ser Phe Leu Ser
    610                 615                 620 ttg tct cag gta tcc agg cca cag ctg cca gga gag ggt gaa gaa ggg    1920
Leu Ser Gln Val Ser Arg Pro Gln Leu Pro Gly Glu Gly Glu Glu Gly
625                 630                 635                 640 gag gag gat ggg gcc cca ggt gat gag gcc aca tca gaa gac agt gag    1968
Glu Glu Asp Gly Ala Pro Gly Asp Glu Ala Thr Ser Glu Asp Ser Glu
                645                 650                 655 gaa gag gag gag ccg gcc gct ggg cgg ccc ctg ggt cgc tgg cgg gag    2016
Glu Glu Glu Glu Pro Ala Ala Gly Arg Pro Leu Gly Arg Trp Arg Glu
            660                 665                 670 gat gcc atc aac tgg cag cgc acg ttc agc gtg ggc gcc atg gac ttc    2064
Asp Ala Ile Asn Trp Gln Arg Thr Phe Ser Val Gly Ala Met Asp Phe
        675                 680                 685 gag ctc ctg cgc tct gac tgg aac gac ctg cgc tgt aac gta tcc ggg    2112
Glu Leu Leu Arg Ser Asp Trp Asn Asp Leu Arg Cys Asn Val Ser Gly
    690                 695                 700 aac ctg caa ctt cct gag gcc gaa gcg gtg gat gta gtg gct cag tac    2160
Asn Leu Gln Leu Pro Glu Ala Glu Ala Val Asp Val Val Ala Gln Tyr
```

```
                                                                -continued 705                 710                 715                 720 atg gag cgg cta aat gca aag cat ggc ggg cgc ttc tcg ctt cta cgc     2208
Met Glu Arg Leu Asn Ala Lys His Gly Gly Arg Phe Ser Leu Leu Arg
                725                 730                 735 atc gtg aac gtg gag aag cgc cgc gac tct gca cgc ggg agc cgc ttc     2256
Ile Val Asn Val Glu Lys Arg Arg Asp Ser Ala Arg Gly Ser Arg Phe
            740                 745                 750 ctc ctg gaa ctg gaa ttg caa gag cgc gga ggg agc cgc cag cgc cta     2304
Leu Leu Glu Leu Glu Leu Gln Glu Arg Gly Gly Ser Arg Gln Arg Leu
        755                 760                 765 tcc gaa tac gtc ttc ctg cgg ttg ccc gga gcc cgc gtt ggg gac gaa     2352
Ser Glu Tyr Val Phe Leu Arg Leu Pro Gly Ala Arg Val Gly Asp Glu
    770                 775                 780 gat gga gaa agt ccc gag ccg cct cca gcc gcc tcg atc cac cca gac     2400
Asp Gly Glu Ser Pro Glu Pro Pro Pro Ala Ala Ser Ile His Pro Asp
785                 790                 795                 800 agt cgc cca gag ctc tgc cgg cct ttg cat ctg gcc tgg cgt cag gat     2448
Ser Arg Pro Glu Leu Cys Arg Pro Leu His Leu Ala Trp Arg Gln Asp
                805                 810                 815 gtc atg gtt cat ttc att gta cca gtg aag aat cag gcg cgc tgg gta     2496
Val Met Val His Phe Ile Val Pro Val Lys Asn Gln Ala Arg Trp Val
            820                 825                 830 gtg cag ttc ctg gca gat atg acc gcg ctg cat gtg cat acg ggg gac     2544
Val Gln Phe Leu Ala Asp Met Thr Ala Leu His Val His Thr Gly Asp
        835                 840                 845 tcg tac ttc aac atc atc ttg gtg gac ttt gag agc gag gac atg gat     2592
Ser Tyr Phe Asn Ile Ile Leu Val Asp Phe Glu Ser Glu Asp Met Asp
    850                 855                 860 gtg gag cgg gcc ctg cgt gcg gct cag cta cct cgg tac cag tac ttg     2640
Val Glu Arg Ala Leu Arg Ala Ala Gln Leu Pro Arg Tyr Gln Tyr Leu
865                 870                 875                 880 aaa cga act gga aac ttc gag cgc tct gca ggc ctg caa act gga gtg     2688
Lys Arg Thr Gly Asn Phe Glu Arg Ser Ala Gly Leu Gln Thr Gly Val
                885                 890                 895 gat gcc gtg gag gac ccc agc agc atc gtt ttc ctc tgt gac ctg cac     2736
Asp Ala Val Glu Asp Pro Ser Ser Ile Val Phe Leu Cys Asp Leu His
            900                 905                 910 atc cac ttc cca cct aat atc ctg gac agc atc cgc aag cat tgc gtg     2784
Ile His Phe Pro Pro Asn Ile Leu Asp Ser Ile Arg Lys His Cys Val
        915                 920                 925 gag ggc aag ctg gcc ttc gcc cct gtg gtc atg cgt ctg ggc tgt gga     2832
Glu Gly Lys Leu Ala Phe Ala Pro Val Val Met Arg Leu Gly Cys Gly
    930                 935                 940 agc tca ccg tgg gac cca cat ggt tac tgg gaa gtg aat gga ttt ggc     2880
Ser Ser Pro Trp Asp Pro His Gly Tyr Trp Glu Val Asn Gly Phe Gly
945                 950                 955                 960 ctc ttt ggg atc tac aaa tca gac ttt gac aga gta gga ggc atg aac     2928
Leu Phe Gly Ile Tyr Lys Ser Asp Phe Asp Arg Val Gly Gly Met Asn
                965                 970                 975 act gag gag ttc cgt gac cag tgg gga ggc gag gac tgg gaa ctt ctt     2976
Thr Glu Glu Phe Arg Asp Gln Trp Gly Gly Glu Asp Trp Glu Leu Leu
            980                 985                 990 gac agg gtc ctg cag gca ggg ctg gag gtg gag agg ctt cga ctg cga     3024
Asp Arg Val Leu Gln Ala Gly Leu Glu Val Glu Arg Leu Arg Leu Arg
        995                 1000                1005 cac ttc tac cac cac tat cac tcg aag cga ggc atg tgg gcc aca cgc     3072
His Phe Tyr His His Tyr His Ser Lys Arg Gly Met Trp Ala Thr Arg
    1010                1015                1020 agc cgc aaa ggt gcc cgc gca cag cga tcc tga                         3105
```

-continued

```
Ser Arg Lys Gly Ala Arg Ala Gln Arg Ser
1025                1030

<210> SEQ ID NO 28
<211> LENGTH: 986
<212> TYPE: PRT
<213> ORGANISM: Mouse

<400> SEQUENCE: 28

Met Gly Ser Pro Arg Ala Ala Leu Leu Met Leu Leu Leu Arg Pro Ile
 1               5                  10                  15

Lys Leu Leu Arg Arg Arg Phe Arg Leu Leu Leu Leu Ala Val Val
            20                  25                  30

Ser Val Gly Leu Trp Thr Leu Tyr Leu Glu Leu Val Ala Ser Ala Gln
        35                  40                  45

Ala Gly Gly Asn Pro Leu Asn His Arg Tyr Gly Ser Trp Arg Glu Leu
    50                  55                  60

Ala Lys Ala Leu Ala Ser Arg Asn Ile Pro Ala Val Asp Pro Asn Leu
 65                  70                  75                  80

Gln Phe Tyr Arg Pro Gln Arg Leu Ser Leu Lys Asp Gln Glu Ile Ala
                85                  90                  95

Arg Ser Arg Ser Arg Asn Ser Ser Tyr Leu Lys Trp Asn Lys Pro Val
            100                 105                 110

Pro Trp Leu Ser Glu Phe Arg Gly His Ala Asn Leu His Val Phe Glu
        115                 120                 125

Asp Trp Cys Gly Ser Ser Ile Gln Gln Leu Arg Asn Asn Leu His Phe
    130                 135                 140

Pro Leu Tyr Pro His Ile Arg Thr Thr Leu Arg Lys Leu Ala Val Ser
145                 150                 155                 160

Pro Lys Trp Thr Asn Tyr Gly Leu Arg Ile Phe Gly Tyr Leu His Pro
                165                 170                 175

Phe Thr Asp Gly Lys Ile Gln Phe Ala Ile Ala Ala Asp Asn Ala
            180                 185                 190

Glu Phe Trp Leu Ser Arg Asp Asp Gln Val Ser Gly Leu Gln Leu Leu
    195                 200                 205

Ala Ser Val Gly Lys Thr Gly Lys Glu Trp Thr Ala Pro Gly Glu Phe
210                 215                 220

Gly Lys Phe Gln Ser Gln Ile Ser Lys Pro Val Ser Leu Ser Ala Ser
225                 230                 235                 240

Leu Arg Tyr Tyr Phe Glu Val Leu His Lys Gln Asn Asp Glu Gly Thr
                245                 250                 255

Asp His Val Glu Val Ala Trp Arg Arg Asn Asp Pro Gly Ala Lys Phe
            260                 265                 270

Thr Ile Ile Asp Ser Pro Phe Leu Ser Leu Phe Thr Asn Glu Thr Ile
    275                 280                 285

Leu Arg Met Asp Glu Val Gly His Ile Pro Gln Thr Ala Ala Ser His
290                 295                 300

Val Gly Ser Ser Asn Thr Pro Arg Asp Glu Gln Pro Pro Ala Asp
305                 310                 315                 320

Met Leu Arg Pro Asp Pro Arg Asp Thr Leu Phe Arg Val Pro Leu Ile
                325                 330                 335

Ala Lys Ser His Leu Arg His Val Leu Pro Asp Cys Pro Tyr Lys Pro
            340                 345                 350

Ser Tyr Leu Val Asp Gly Leu Pro Leu Gln Arg Tyr Gln Gly Leu Arg
    355                 360                 365
```

```
Phe Val His Leu Ser Phe Val Tyr Pro Asn Asp Tyr Thr Arg Leu Ser
        370                 375                 380

His Met Glu Thr His Asn Lys Cys Phe Tyr Gln Glu Ser Ala Tyr Asp
385                 390                 395                 400

Gln Asp Arg Ser Ser Phe Gln Glu Tyr Ile Lys Met Asp Lys Pro Glu
                    405                 410                 415

Lys His Gly Pro Glu Gln Pro Ala Gly Leu Glu Asp Gly Leu Leu Glu
                420                 425                 430

Glu Ser Gln Tyr Glu Asp Val Pro Glu Glu Ile Pro Thr Ser Gln Asp
            435                 440                 445

Gln Asn Thr Gly Ile Gln Gly Arg Lys Gln Lys Thr Ile Ser Thr Pro
        450                 455                 460

Gly Leu Gly Val Thr Asp Tyr His Leu Arg Lys Leu Leu Ala Arg Ser
465                 470                 475                 480

Gln Ser Gly Pro Val Ala Pro Leu Ser Lys Gln Asn Ser Thr Thr Ala
                    485                 490                 495

Phe Pro Thr Arg Thr Ser Asn Ile Pro Val Gln Arg Pro Glu Lys Ser
                500                 505                 510

Pro Val Pro Ser Arg Asp Leu Ser His Ser Asp Gln Gly Ala Arg Arg
            515                 520                 525

Asn Leu Pro Leu Ile Gln Arg Ala Arg Pro Thr Gly Asp Arg Pro Gly
        530                 535                 540

Lys Thr Leu Glu Gln Ser Gln Trp Leu Asn Gln Val Glu Ser Phe Ile
545                 550                 555                 560

Ala Glu Gln Arg Arg Gly Asp Arg Ile Glu Pro Pro Thr Pro Ser Arg
                    565                 570                 575

Gly Trp Arg Pro Glu Glu Asp Val Val Ile Ala Ala Asp Gln Glu Gly
                580                 585                 590

Glu Val Glu Glu Glu Glu Gly Glu Asp Glu Glu Asp Met Ser
            595                 600                 605

Glu Val Phe Glu Tyr Val Pro Met Phe Asp Pro Val Val Asn Trp Gly
        610                 615                 620

Gln Thr Phe Ser Ala Gln Asn Leu Asp Phe Gln Ala Leu Arg Thr Asp
625                 630                 635                 640

Trp Ile Asp Leu Asn Cys Asn Thr Ser Gly Asn Leu Leu Leu Pro Glu
                    645                 650                 655

Gln Glu Ala Leu Glu Val Thr Arg Val Phe Leu Arg Lys Leu Ser Gln
                660                 665                 670

Arg Thr Arg Gly Arg Tyr Gln Leu Gln Arg Ile Val Asn Val Glu Lys
            675                 680                 685

Arg Gln Asp Arg Leu Arg Gly Arg Tyr Phe Leu Glu Leu Glu Leu
        690                 695                 700

Leu Asp Gly Gln Arg Leu Val Arg Leu Ser Glu Tyr Val Ser Thr Arg
705                 710                 715                 720

Gly Trp Arg Gly Gly Asp His Pro Gly Arg Glu Asp Thr Glu Ala Arg
                    725                 730                 735

Asn Leu Gln Gly Leu Val Trp Ser Pro Arg Asn Arg His Arg His Val
                740                 745                 750

Leu Asn Ala Gln Asp Pro Glu Pro Lys Leu Cys Trp Pro Gln Gly Phe
            755                 760                 765

Ser Trp Asn His Arg Ala Val Val His Phe Ile Val Pro Val Lys Asn
        770                 775                 780
```

```
Gln Ala Arg Trp Val Gln Gln Phe Ile Arg Asp Met Glu Ser Leu Ser
785                 790                 795                 800

Gln Val Thr Gly Asp Ala His Phe Ser Ile Ile Thr Asp Tyr Ser
        805                 810                 815

Ser Glu Asp Met Asp Val Glu Met Ala Leu Lys Arg Ser Arg Leu Arg
        820                 825                 830

Ser Tyr Gln Tyr Leu Lys Leu Ser Gly Asn Phe Glu Arg Ser Ala Gly
        835                 840                 845

Leu Gln Ala Gly Ile Asp Leu Val Lys Asp Pro His Ser Ile Ile Phe
850                 855                 860

Leu Cys Asp Leu His Ile His Phe Pro Ala Gly Ile Ile Asp Thr Ile
865                 870                 875                 880

Arg Lys His Cys Val Glu Gly Lys Met Ala Phe Ala Pro Met Val Met
                885                 890                 895

Arg Leu His Cys Gly Ala Thr Pro Gln Trp Pro Glu Gly Tyr Trp Glu
            900                 905                 910

Val Asn Gly Phe Gly Leu Leu Gly Ile Tyr Lys Ser Asp Leu Asp Lys
            915                 920                 925

Ile Gly Gly Met Asn Thr Lys Glu Phe Arg Asp Arg Trp Gly Gly Glu
930                 935                 940

Asp Trp Glu Leu Leu Asp Arg Ile Leu Gln Ala Gly Leu Glu Val Glu
945                 950                 955                 960

Arg Leu Ser Leu Arg Asn Phe His His Phe His Ser Lys Arg Gly
                965                 970                 975

Met Trp Asn Arg Arg Gln Met Lys Met Pro
            980                 985

<210> SEQ ID NO 29
<211> LENGTH: 2961
<212> TYPE: DNA
<213> ORGANISM: Mouse

<400> SEQUENCE: 29 atg ggg agc ccc cgc gcc gcg ttg ctg atg ctg ctc ctg cgc ccg atc    48
Met Gly Ser Pro Arg Ala Ala Leu Leu Met Leu Leu Leu Arg Pro Ile
1               5                   10                  15 aag ctg ctg agg agg cgc ttc cgg ctg ctg ctg ctc gcc gta gta        96
Lys Leu Leu Arg Arg Arg Phe Arg Leu Leu Leu Leu Ala Val Val
            20                  25                  30 tcg gtg gga ctc tgg act ctg tat ctg gag ctg gtg gcg tcg gcc cag   144
Ser Val Gly Leu Trp Thr Leu Tyr Leu Glu Leu Val Ala Ser Ala Gln
        35                  40                  45 gcc ggc ggg aac ccc ctg aac cac agg tat ggc agc tgg cga gaa ctg   192
Ala Gly Gly Asn Pro Leu Asn His Arg Tyr Gly Ser Trp Arg Glu Leu
    50                  55                  60 gcc aag gcc cta gcc agc agg aac atc cca gcc gtt gat ccg aat ctc   240
Ala Lys Ala Leu Ala Ser Arg Asn Ile Pro Ala Val Asp Pro Asn Leu
65                  70                  75                  80 caa ttc tac cgt ccc cag cgg ctg agc ctc aag gac caa gaa att gcc   288
Gln Phe Tyr Arg Pro Gln Arg Leu Ser Leu Lys Asp Gln Glu Ile Ala
                85                  90                  95 cga agt agg agt agg aac agc agc tac ctg aag tgg aac aag cct gtc   336
Arg Ser Arg Ser Arg Asn Ser Ser Tyr Leu Lys Trp Asn Lys Pro Val
            100                 105                 110 ccc tgg ctc tca gag ttc cgg ggc cac gcc aac cta cat gtg ttt gaa   384
Pro Trp Leu Ser Glu Phe Arg Gly His Ala Asn Leu His Val Phe Glu
        115                 120                 125
```

```
gac tgg tgt ggc agc tcc atc caa cag ctg agg aac aac ctg cac ttc      432
Asp Trp Cys Gly Ser Ser Ile Gln Gln Leu Arg Asn Asn Leu His Phe
    130                 135                 140 cca ctc tac ccc cac atc cgc aca act ctg agg aag ctg gct gtg tcc      480
Pro Leu Tyr Pro His Ile Arg Thr Thr Leu Arg Lys Leu Ala Val Ser
145                 150                 155                 160 ccc aag tgg acc aac tat ggc ctc cgc ata ttt ggc tat ctg cac cct      528
Pro Lys Trp Thr Asn Tyr Gly Leu Arg Ile Phe Gly Tyr Leu His Pro
                165                 170                 175 ttc acc gat ggg aaa atc cag ttt gcc atc gct gct gat gac aat gct      576
Phe Thr Asp Gly Lys Ile Gln Phe Ala Ile Ala Ala Asp Asp Asn Ala
            180                 185                 190 gag ttc tgg ctg agt cgt gat gac cag gtc tca ggc ctt cag ctg ctg      624
Glu Phe Trp Leu Ser Arg Asp Asp Gln Val Ser Gly Leu Gln Leu Leu
        195                 200                 205 gcc agc gtg ggc aag aca gga aag gaa tgg aca gcc cct gga gag ttt      672
Ala Ser Val Gly Lys Thr Gly Lys Glu Trp Thr Ala Pro Gly Glu Phe
    210                 215                 220 ggg aaa ttt cag agt caa att tcc aag cca gtg agt tta tca gcc tcc      720
Gly Lys Phe Gln Ser Gln Ile Ser Lys Pro Val Ser Leu Ser Ala Ser
225                 230                 235                 240 ctc agg tac tac ttt gag gtc ctg cac aag caa aat gat gaa ggc act      768
Leu Arg Tyr Tyr Phe Glu Val Leu His Lys Gln Asn Asp Glu Gly Thr
                245                 250                 255 gac cac gtg gag gtc gcg tgg aga cgg aat gac cct gga gcc aag ttc      816
Asp His Val Glu Val Ala Trp Arg Arg Asn Asp Pro Gly Ala Lys Phe
            260                 265                 270 acc atc att gac tcc ccc ttc tta tct ctc ttt aca aat gag acc atc      864
Thr Ile Ile Asp Ser Pro Phe Leu Ser Leu Phe Thr Asn Glu Thr Ile
        275                 280                 285 cta agg atg gat gag gtg ggc cat atc cca cag aca gcc agc cat          912
Leu Arg Met Asp Glu Val Gly His Ile Pro Gln Thr Ala Ala Ser His
    290                 295                 300 gta ggc tcc tcc aac act cct ccc cgg gat gag cag ccc cca gct gac      960
Val Gly Ser Ser Asn Thr Pro Pro Arg Asp Glu Gln Pro Pro Ala Asp
305                 310                 315                 320 atg ctg cgg cct gac cct cgg gac acc ctc ttt cga gtg cct ctg atc     1008
Met Leu Arg Pro Asp Pro Arg Asp Thr Leu Phe Arg Val Pro Leu Ile
                325                 330                 335 gcc aag tcc cat ctg cgc cac gtc ctg ccc gat tgt ccc tac aaa ccc     1056
Ala Lys Ser His Leu Arg His Val Leu Pro Asp Cys Pro Tyr Lys Pro
            340                 345                 350 agc tac ctg gtg gat gga ctc ccg cta cag cgc tac cag ggc ctc cgt     1104
Ser Tyr Leu Val Asp Gly Leu Pro Leu Gln Arg Tyr Gln Gly Leu Arg
        355                 360                 365 ttt gtt cac ctg tcc ttt gtt tat ccc aat gac tat acc cgt ctg agc     1152
Phe Val His Leu Ser Phe Val Tyr Pro Asn Asp Tyr Thr Arg Leu Ser
    370                 375                 380 cac atg gag acc cat aat aaa tgt ttc tac caa gaa agt gcc tat gac     1200
His Met Glu Thr His Asn Lys Cys Phe Tyr Gln Glu Ser Ala Tyr Asp
385                 390                 395                 400 cag gac agg tcc agc ttc cag gaa tat atc aag atg gac aag cca gag     1248
Gln Asp Arg Ser Ser Phe Gln Glu Tyr Ile Lys Met Asp Lys Pro Glu
                405                 410                 415 aag cat ggc ccg gag cag cca gca ggt ttg gag gat ggc ctt cta gaa     1296
Lys His Gly Pro Glu Gln Pro Ala Gly Leu Glu Asp Gly Leu Leu Glu
            420                 425                 430 gaa tcc cag tat gaa gac gta cca gag gaa atc ccc acc tct caa gac     1344
Glu Ser Gln Tyr Glu Asp Val Pro Glu Glu Ile Pro Thr Ser Gln Asp
        435                 440                 445
```

```
cag aat act ggg ata caa ggg aga aaa cag aag act att tcc acc ccg      1392
Gln Asn Thr Gly Ile Gln Gly Arg Lys Gln Lys Thr Ile Ser Thr Pro
    450                 455                 460 ggg ctg ggt gtc act gac tac cac ctg cgg aag ctc ttg gct cgc tca      1440
Gly Leu Gly Val Thr Asp Tyr His Leu Arg Lys Leu Leu Ala Arg Ser
465                 470                 475                 480 cag agt ggc cct gta gcg cct ctt tcc aaa cag aac tct aca act gcc      1488
Gln Ser Gly Pro Val Ala Pro Leu Ser Lys Gln Asn Ser Thr Thr Ala
                485                 490                 495 ttt cca acc agg aca agc aac atc cca gtc cag cgg cca gag aaa agc      1536
Phe Pro Thr Arg Thr Ser Asn Ile Pro Val Gln Arg Pro Glu Lys Ser
            500                 505                 510 cct gtg ccc agc cga gat ttg tct cat tct gac cag ggg gcc cgg agg      1584
Pro Val Pro Ser Arg Asp Leu Ser His Ser Asp Gln Gly Ala Arg Arg
        515                 520                 525 aac ctg cct ctc atc cag aga gcc agg ccc act ggt gac aga cct ggg      1632
Asn Leu Pro Leu Ile Gln Arg Ala Arg Pro Thr Gly Asp Arg Pro Gly
    530                 535                 540 aag act ctt gag cag tcc cag tgg ctg aat caa gtg gaa tcc ttc att      1680
Lys Thr Leu Glu Gln Ser Gln Trp Leu Asn Gln Val Glu Ser Phe Ile
545                 550                 555                 560 gct gag cag aga agg gga gac agg ata gag cct cca acc ccc agc agg      1728
Ala Glu Gln Arg Arg Gly Asp Arg Ile Glu Pro Pro Thr Pro Ser Arg
                565                 570                 575 ggc tgg cgt cct gag gag gac gtg gtg ata gcg gcg gac cag gaa gga      1776
Gly Trp Arg Pro Glu Glu Asp Val Val Ile Ala Ala Asp Gln Glu Gly
            580                 585                 590 gaa gtg gag gag gag gaa gag ggg gaa gat gag gaa gat atg agt         1824
Glu Val Glu Glu Glu Glu Glu Gly Glu Asp Glu Glu Asp Met Ser
        595                 600                 605 gag gtg ttc gaa tat gtg cct atg ttt gac cca gtg gtg aac tgg ggc      1872
Glu Val Phe Glu Tyr Val Pro Met Phe Asp Pro Val Val Asn Trp Gly
    610                 615                 620 cag acc ttc agc gct cag aac ctc gac ttc caa gcc ctg aga acc gac      1920
Gln Thr Phe Ser Ala Gln Asn Leu Asp Phe Gln Ala Leu Arg Thr Asp
625                 630                 635                 640 tgg atc gac ctg aac tgt aac aca tcg ggc aac ctg ctg ctt ccg gag      1968
Trp Ile Asp Leu Asn Cys Asn Thr Ser Gly Asn Leu Leu Leu Pro Glu
                645                 650                 655 cag gag gcc ctg gag gtc aca cgg gtc ttc ctg aga aag ctc agc cag      2016
Gln Glu Ala Leu Glu Val Thr Arg Val Phe Leu Arg Lys Leu Ser Gln
            660                 665                 670 agg acc cgg ggg aga tac cag ctg cag cgc att gtg aat gtg gag aag      2064
Arg Thr Arg Gly Arg Tyr Gln Leu Gln Arg Ile Val Asn Val Glu Lys
        675                 680                 685 cgc cag gac cgg ctg cgc ggg ggg cgc tac ttc ctg gag ctt gaa ctg      2112
Arg Gln Asp Arg Leu Arg Gly Gly Arg Tyr Phe Leu Glu Leu Glu Leu
    690                 695                 700 ctg gat ggc caa cgc ctg gta cgg ctc tcg gag tac gtg tcc act aga      2160
Leu Asp Gly Gln Arg Leu Val Arg Leu Ser Glu Tyr Val Ser Thr Arg
705                 710                 715                 720 ggc tgg cgg gga ggt gac cac cca ggc agg gag gac aca gaa gct cgg      2208
Gly Trp Arg Gly Gly Asp His Pro Gly Arg Glu Asp Thr Glu Ala Arg
                725                 730                 735 aac ctg cag ggt ctg gtc tgg agc cca cgc aac cgt cac aga cat gtc      2256
Asn Leu Gln Gly Leu Val Trp Ser Pro Arg Asn Arg His Arg His Val
            740                 745                 750 ctg aat gcc cag gat cca gag ccc aag ctc tgc tgg ccc caa ggt ttc      2304
Leu Asn Ala Gln Asp Pro Glu Pro Lys Leu Cys Trp Pro Gln Gly Phe
```

```
                755                 760                 765
tcc tgg aac cat cga gct gtg gtc cac ttt att gtg cct gtg aag aac         2352
Ser Trp Asn His Arg Ala Val Val His Phe Ile Val Pro Val Lys Asn
    770                 775                 780 cag gct cgc tgg gtg cag cag ttc atc aga gat atg gag agc ctg tcc         2400
Gln Ala Arg Trp Val Gln Gln Phe Ile Arg Asp Met Glu Ser Leu Ser
785                 790                 795                 800 caa gtc act gga gat gca cat ttc agc atc att atc aca gac tat agc         2448
Gln Val Thr Gly Asp Ala His Phe Ser Ile Ile Ile Thr Asp Tyr Ser
                805                 810                 815 agt gag gac atg gat gtg gag atg gct ctg aag agg tcc aga ctg cgg         2496
Ser Glu Asp Met Asp Val Glu Met Ala Leu Lys Arg Ser Arg Leu Arg
            820                 825                 830 agc tac cag tac ctg aag ctg agt gga aac ttt gag cgc tct gct gga         2544
Ser Tyr Gln Tyr Leu Lys Leu Ser Gly Asn Phe Glu Arg Ser Ala Gly
        835                 840                 845 ctg cag gct ggc ata gac ctg gtg aag gat cca cac agc atc atc ttc         2592
Leu Gln Ala Gly Ile Asp Leu Val Lys Asp Pro His Ser Ile Ile Phe
    850                 855                 860 ctc tgt gac ctg cac atc cac ttt cca gca gga atc att gat acc atc         2640
Leu Cys Asp Leu His Ile His Phe Pro Ala Gly Ile Ile Asp Thr Ile
865                 870                 875                 880 cgg aag cac tgt gtg gag ggc aag atg gcc ttt gcc ccc atg gtg atg         2688
Arg Lys His Cys Val Glu Gly Lys Met Ala Phe Ala Pro Met Val Met
                885                 890                 895 cgg ctg cac tgt ggg gcc acc cca cag tgg cct gag ggc tac tgg gaa         2736
Arg Leu His Cys Gly Ala Thr Pro Gln Trp Pro Glu Gly Tyr Trp Glu
            900                 905                 910 gta aat gga ttt gga ctg ctc ggg atc tac aag tct gac ctg gac aag         2784
Val Asn Gly Phe Gly Leu Leu Gly Ile Tyr Lys Ser Asp Leu Asp Lys
        915                 920                 925 atc gga ggc atg aac acc aag gag ttc aga gac cgc tgg gga ggg gag         2832
Ile Gly Gly Met Asn Thr Lys Glu Phe Arg Asp Arg Trp Gly Gly Glu
    930                 935                 940 gac tgg gag ctg ctg gac agg att ctc caa gca ggc ctg gaa gtg gag         2880
Asp Trp Glu Leu Leu Asp Arg Ile Leu Gln Ala Gly Leu Glu Val Glu
945                 950                 955                 960 cgg ctc tcc ctc agg aac ttc ttc cat cac ttc cat tcc aag cga ggc         2928
Arg Leu Ser Leu Arg Asn Phe Phe His His Phe His Ser Lys Arg Gly
                965                 970                 975 atg tgg aac cgt cgc caa atg aag atg ccg tga                             2961
Met Trp Asn Arg Arg Gln Met Lys Met Pro
            980                 985
```

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: FLAG
      peptide

<400> SEQUENCE: 30

Asp Tyr Lys Asp Asp Asp Asp Lys
 1               5

<210> SEQ ID NO 31
<211> LENGTH: 30
<212> TYPE: DNA
<213> ORGANISM: Artificial Sequence
<220> FEATURE:
<223> OTHER INFORMATION: Oligonucleotide primer used in PCR for -continued

```
        amplifying mNGalNAc-T1 cDNA

<400> SEQUENCE: 31
cccaagcttc gcctgggcta cgggcgagat                                   30

<210> SEQ ID NO 32
<211> LENGTH: 31
<212> TYPE: DNA
<213> ORGANISM: Artificial Sequence
<220> FEATURE:
<223> OTHER INFORMATION: Oligonucleotide primer used in PCR for
        amplifying mNGalNAc-T1 cDNA

<400> SEQUENCE: 32
gctctagact caggatcgct gtgcgcgggc a                                 31

<210> SEQ ID NO 33
<211> LENGTH: 30
<212> TYPE: DNA
<213> ORGANISM: Artificial Sequence
<220> FEATURE:
<223> OTHER INFORMATION: Oligonucleotide primer used in PCR for
        amplifying mNGalNAc-T2 cDNA

<400> SEQUENCE: 33
cccaagcttc ggcccaggcc ggcgggaacc                                   30

<210> SEQ ID NO 34
<211> LENGTH: 29
<212> TYPE: DNA
<213> ORGANISM: Artificial Sequence
<220> FEATURE:
<223> OTHER INFORMATION: Oligonucleotide primer used in PCR for
        amplifying mNGalNAc-T1 cDNA

<400> SEQUENCE: 34
ggaattctca cggcatcttc atttggcga                                    29
```

N-ACETYLGALACTOSAMINE TRANSFERASES AND NUCLEIC ACIDS ENCODING THE SAME

This application is the US national phase of international application PCT/JP2003/010309 filed 13 Aug. 2003 which designated the U.S. and claims benefit of JP 2002-236292, dated 14 Aug. 2002, the entire content of which is hereby incorporated by reference.

TECHNICAL FIELD

The present invention relates to novel enzymes having the activity of transferring N-acetylgalactosamine to N-acetylglucosamine via a β1-4 linkage and nucleic acids encoding the same, as well as to nucleic acids for assaying said nucleic acids.

BACKGROUND ART

In various kinds of organisms, structures having a linkage of disaccharide of N-acetylgalactosamine-N-acetylglucosamine have been found in oligosaccharides of glycoproteins and glycolipids [see References 1 and 2]. In humans, this disaccharide structure is known as a β1-4 linkage (GalNAcβ1-4GlcNAc), and is found only in N-glycans [see Reference 3]. Methods for obtaining human-type oligosaccharides including said structure are limited to methods using complicated chemical synthesis and methods obtaining the oligosaccharides from natural proteins. Further, the above disaccharide structure includes in vivo a galactose substituted for a N-acetylgalactosamine. Therefore, it is a lengthy, laborious process to obtain oligosaccharides having the target disaccharide structure.

Prior to the present application, the inventors identified ppGalNAc-T10, -T11, -T12, -T13, -T14, -T15, -T16, -T17, CSGalNAc-T1, and -T2 as enzymes having an activity of transferring N-acetylgalactosamine to glucuronic acids and polypeptides, and further, they clarified the structures of these genes. Already known are at least 22 N-acetylgalactosamine transferases that have the activity of transferring N-acetylgalactosamine (Table 1), and each of the transferases have different specificities of acceptor substrates.

TABLE 1

N-acetylgalactosamine transferase and the substrate specificity

| Formal Name | Abbreviation | Origin | Substrate specificity | References |
|---|---|---|---|---|
| UDP-GalNAc:polypeptide N-acetylgalactosaminyl transferase I | ppGalNAc-T1 | human | Ser/Thr | White, T. etc (1995) |
| UDP-GalNAc:polypeptide N-acetylgalactosaminyl transferase II | ppGalNAc-T2 | human | Ser/Thr | White, T. etc (1995) |
| UDP-GalNAc:polypeptide N-acetylgalactosaminyl transferase III | ppGalNAc-T3 | human | Ser/Thr | Bennet, E. P. etc (1996) |
| UDP-GalNAc:polypeptide N-acetylgalactosaminyl transferase IV | ppGalNAc-T4 | human | Ser/Thr | Bennet, E. P. etc (1998) |
| UDP-GalNAc:polypeptide N-acetylgalactosaminyl transferase VI | ppGalNAc-T6 | human | Ser/Thr | Bennet, E. P. etc (1999) (1) |
| UDP-GalNAc:polypeptide N-acetylgalactosaminyl transferase VII | ppGalNAc-T7 | human | Ser/Thr | Bennet, E. P. etc (1999) (2) |
| UDP-GalNAc:polypeptide N-acetylgalactosaminyl transferase VIII | ppGalNAc-T8 | human | Ser/Thr | White, K. E. etc (2000) |
| UDP-GalNAc:polypeptide N-acetylgalactosaminyl transferase IX | ppGalNAc-T9 | human | Ser/Thr | Toba, S. etc (2000) |
| UDP-GalNAc:polypeptide N-acetylgalactosaminyl transferase X | ppGalNAc-T10 | human | Ser/Thr | JP No. 2001-401455 (unpublished) |
| UDP-GalNAc:polypeptide N-acetylgalactosaminyl transferase XI | ppGalNAc-T11 | human | Ser/Thr | JP No. 2001-401507 (unpublished) |
| UDP-GalNAc:polypeptide N-acetylgalactosaminyl transferase XII | ppGalNAc-T12 | human | Ser/Thr | JP No. 2001-401507 (unpublished) |
| UDP-GalNAc:polypeptide N-acetylgalactosaminyl transferase XIII | ppGalNAc-T13 | human | Ser/Thr | JP No. 2001-401507 (unpublished) |
| UDP-GalNAc:polypeptide N-acetylgalactosaminyl transferase XIV | ppGalNAc-T14 | human | Ser/Thr | Guo, J. M. etc (2002) |
| UDP-GalNAc:polypeptide N-acetylgalactosaminyl transferase XV | ppGalNAc-T15 | human | Ser/Thr | JP No. 2001-401507 (unpublished) |
| UDP-GalNAc:polypeptide N-acetylgalactosaminyl transferase XVI | ppGalNAc-T16 | human | Ser/Thr | JP No. 2001-401507 (unpublished) |

TABLE 1-continued

N-acetylgalactosamine transferase and the substrate specificity

| Formal Name | Abbreviation | Origin | Substrate specificity | References |
|---|---|---|---|---|
| UDP-GalNAc:polypeptide K-acetylgalactosaminyl transferase XVII | ppGalNAc-T17 | human | Ser/Thr | JP No. 2001-401507 (unpublished) |
| β1,4-N-acetylgalactosamine transferase | β4GalNAcT | human | GM3, GD3, LacCer | Nagata, Y. etc (1992) |
| UDP-GalNAc:H-α1,3-N-acetylgalactosamine transferase | Hist blood A group transferase | human | Fucα1,2Galβ1-R | Yamamoto, F. etc (1990) |
| UDP-GalNAc:globoside α1,3-N-acetylgalactosamine transferase I | formalin glycolipid synthase | human | GalNAcβ1-3Galα1-4Galβ1-3Glc-Cer | Xu, H. etc (1999) |
| Chondroitin sulfate N-acetylglactosamin transferase I | CSGalNAc-T1 | human | GlcA | JP No. 2002-129156 (unpublished) |
| Chondroitin sulfate N-acetylglactosamin transferase II | CSGalNAc-T2 | human | GlcA | JP No. 2002-24202 (unpublished) |

DISCLOSURE OF INVENTION

Isolation of an enzyme having the activity of transferring N-acetylgalactosamine to N-acetylglucosamine via a β1-4 linkage and an explanation of the structure of its gene enable the production of said enzyme or the like through genetic engineering techniques, and the diagnosis of diseases on the basis of said gene or the like. However, such an enzyme has not been isolated/purified yet and there is no key to isolating such an enzyme and identifying its gene. Therefore, no antibody against such an enzyme has been prepared.

Therefore, the present invention provides a protein having an activity of transferring N-acetylgalactosamine to N-acetylglucosamine via a β1-4 linkage and nucleic acids for encoding the same. The present invention also provides a cell introduced with a recombinant vector expressing said nucleic acids in a host cell and said nucleic acids, and expressing said nucleic acids and said proteins. Further, said protein expressed can be used for producing an antibody. Therefore, the present invention also provides a method for producing said protein. Further, the expressed protein and said antibody to the protein can be applied to immnohistochemical staining, and immunoassay of RIA and EIA and the like. Moreover, the present invention provides an analytical nucleic acid for assaying the above nucleic acid of the present invention.

As described above, the objective enzymes have not yet been identified, and therefore, the partial sequence of the amino acids cannot be informed. In general, it is difficult to isolate and purify proteins which are included in only a very small quantity in cells. Therefore, it is supposed that it is not easy to isolate enzymes which have so far not been isolated from cells. Thereat, the inventors tried to isolate and purify target enzymes, by making a region of which identity is thought to be high into a target, which may have the homologous sequence in nucleic acid sequences of genes between a objective enzyme and various kinds of enzymes having relatively similar activity. Specifically, the inventors first searched nucleic acid sequences of publicly-known β1,4-galactose transferases, and identified homologous regions. Second, primers were designed based on these homologous regions, and a full-length open reading flam was identified from cDNA library by 5' RACE (rapid amplification of cDNA ends) method. Further, the inventors succeeded in cloning a gene of said enzyme by PCR, and completed the present invention by determining nucleic acid sequences thereof and putative amino acid sequences.

The present invention provides a protein having the activity of transferring N-acetylgalactosamine and nucleic acid encoding the same, and thereby assists in satisfying these various requirements in the art.

Namely, the present invention provides a mammal protein having the activity of transferring N-acetylgalactosamine to N-acetylglucosamine via a β1-4 linkage.

The human protein of the present invention has, typically, amino acid sequence of SEQ ID NO: 1 or 3, which is presumed from nucleic acid sequence of SEQ ID NO: 2 or 4.

The mouse protein of the present invention has amino acid sequence of SEQ ID NO: 26 or 28, which is presumed from nucleic acid sequence of SEQ ID NO: 27 or 29.

The present invention includes not only the protein having the amino acid sequence which is selected from a group consisting of SEQ ID NOs: 1, 3, 26 and 28 but also proteins having an identity of 50% or more to said sequence. The present invention includes proteins having said amino acid sequence, wherein one or more amino acids are substituted or deleted, or one or more amino acids are inserted or added.

The proteins of the present invention have amino acid sequences which have an identity of 60% or more, preferably 70% or more, more preferably 80% or more, still more preferably 90%, and most preferably 95% to the amino acid sequence which is selected from a group consisting of SEQ ID NOs: 1, 3, 26 and 28.

The present invention provides nucleic acids encoding the protein of the present invention.

The nucleic acids of the present invention have, typically, the nucleic acid sequence which is selected from a group consisting of SEQ ID NOs: 2, 4, 27 and 29, nucleic acid sequences in which one or more nucleic acids are substituted, deleted, inserted and/or added to the above nucleic acid sequence, or a nucleic acid sequence which hybridizes with said nucleic acid sequence under stringent conditions, and which includes the nucleic acids complementary to the above sequences. In one embodiment, the present invention includes, but is not limited to, nucleic acids having the nucleic acid sequence represented by nucleotides 1-3120 of the nucleic acid sequence shown in SEQ ID NO: 2, nucleotides 1-2997 of the nucleic acid sequence shown in SEQ ID No: 4, nucleotides 1-3105 of the nucleic acid sequence shown in SEQ ID NO: 27, nucleotides 1-2961 of the nucleic acid sequence shown in SEQ ID No: 29.

The present invention provides a recombinant vector containing the nucleic acids of the present invention.

The present invention provides the transformants obtained by introducing the recombinant vector of the present invention into host cells.

The present invention provides an analytical nucleic acid which hybridizes to the nucleic acids encoding the protein of the present invention under stringent conditions. The analytical nucleic acid preferably has the sequence shown in any one of SEQ ID NOs: 20, 21, 23 and 24 in the case of using the analytical nucleic acid of the present invention as a probe for assaying the nucleic acids encoding said protein. Further, the analytical nucleic acid of the present invention can be used as a cancer marker.

The present invention provides an assay kit comprising the analytical nucleic acid which hybridizes to the nucleic acid of the present invention.

The present invention provides the isolated antibody binding to the protein of the present invention or the monoclonal antibody thereof.

Further, the present invention provides a method for determining a canceration of biological sample which comprises a step of quantifying the protein or the nucleic acid of the present invention in the biological sample.

DETAILED DESCRIPTION OF THE INVENTION

Figure 1:
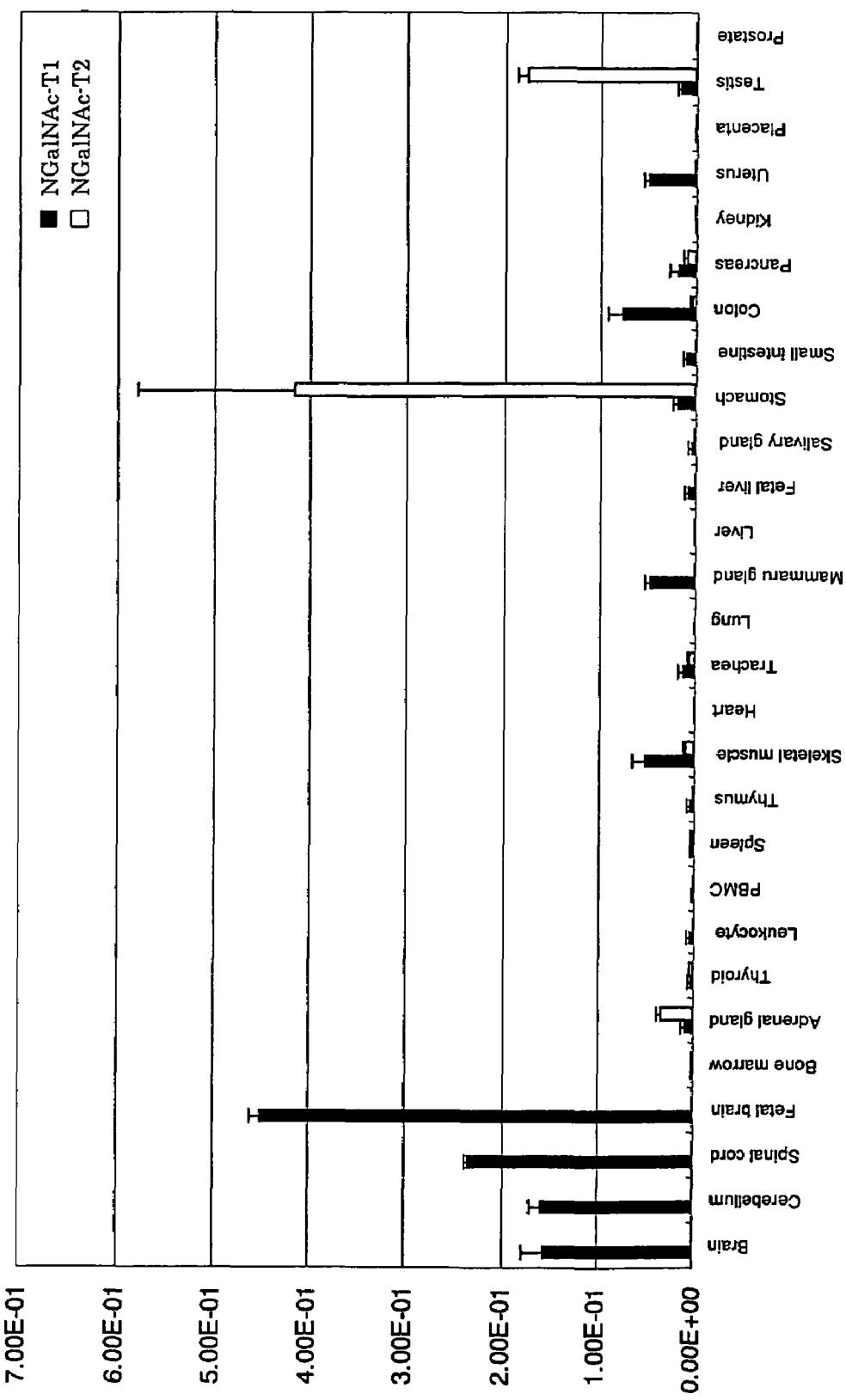
FIG. 1 is a graph showing the quantitative analysis of expression level of NGalNAc-T1 or NGalNAc-T2 gene in various human tissues by the real time PCR. The axis of ordinates represents a relative ratio of expression level of NGalNAc-T1 or NGalNAc-T2 gene to that of a control glyceraldehyde-3-phsopate dehydrogenase (GAPDH) gene. The expressions of NGalNAc-T1 and NGalNAc-T2 gene are represented as a black bar and a white bar, respectively.

In order to explain the present invention, a preferable embodiments for carrying out the invention are described in detail below.

(1) Proteins

The nucleic acid encoding the human protein of the present invention cloned by the method described in detail in the examples below has the nucleotide sequence shown in SEQ ID NO: 2 or 4 in the Sequence Listing under which a deduced amino acid sequence encoded thereby is also shown. In addition, SEQ ID NO: 1 or 3 shows only said amino acid sequence.

The proteins (hereinafter, denominated "NGalNAc-T1" and "NGalNAc-T2") of the present invention obtained in the examples below are enzymes having the properties listed below. In addition, each property of the proteins of the present invention and the method for determining the activity thereof are described in detail in the examples below.

Activity: Transferring N-acetylgalactosamine to N-acetylglucosamine via a β1-4 linkage. The catalytic reaction is represented by the reaction formula:

UDP-N-acetyl-D-galactosamine+N-acetyl-D-glucosamine-R→UDP+N-acetyl-D-galactosaminyl-N-acetyl-D-glucosamine-R (UDP-GalNAc+GlcNAc-R→UDP+GalNAc-GlcNAc-R)

Specific substrate: N-acetyl-glucosamine such as N-acetyl-glucosamine β1-3-R (R is a residue of which hydroxyl group of mannose and p-nitrophenol and the like binds via an ether linkage).

In a preferable embodiment, the proteins of the present invention have at least one of the following properties, preferably these properties:

(A) Specificity of Acceptor Substrates (a) When O-linked oligosaccharides are used as an acceptor substrate, said proteins have the activity of transferring N-acetylgalactosamine to GlcNAcβ1-6(Galβ1-3)GalNAcα-pNp (hereinafter, "core2-pNp"), GlcNAcβ1-3GalNAcα-pNp (hereinafter, "core3-pNp"), GlcNAcβ1-6GalNAcα-pNp (hereinafter, "core6-pNp") via a β1-4 linkage, wherein the abbreviations used are: GlcNAc, N-acetylglucosamine; GalNAc, N-acetylgalactosamine; Gal, galactose; pNp, p-nitrophenyl. Preferably, said proteins have the transferring activity to core6-pNp.

(b) When N-linked oligosaccharides are used as an acceptor substrate, said proteins have the activity of transferring N-acetylgalactosamine to GlcNAc at the non-reducing end of said oligosaccharides via a β1-4 linkage, provided that said activity reduces when said oligosaccharides have the following properties:

(i) having fucose (Fuc) residues in the structure of said oligosaccharides; and (ii) having one or more branched chains wherein GalNAc residues bind to GlcNAc residues at the non-reducing end.

(B) Optimum pH in Enzymatic Activity

The activity tends to be higher in pH 6.5 of MES (2-morpholineethanesulfonic acid) buffer. In HEPES ([4-(2-hydroxyethyl)-1-piperazinyl]ethanesulfonic acid) buffer, the activity tends to be higher in pH 6.75 for NGalNAc-T1 and pH 7.4 for NGalNAc-T2.

(C) Requirement of Divalent Ions

In NGalNAc-T1, the activity tends to be higher in the MES buffer including at least $Mn^{2+}$, or $Cu^{2+}$, preferably $Mn^{2+}$. In NGalNAc-T2, the activity tends to be higher in the MES buffer including $Mg^{2+}$, $Mn^{2+}$, or $Co^{2+}$, preferably $Mg^{2+}$.

The nucleic acid encoding the mouse protein of the present invention also has the nucleotide sequence shown in SEQ ID NO: 27 or 29 in the Sequence Listing under which a deduced amino acid sequence encoded thereby is also shown. In addition, SEQ ID NO: 1 or 3 shows only said amino acid sequence. The proteins (hereinafter, denominated "mNGalNAc-T1" and "mNGalNAc-T2") of the present invention are enzymes having the above properties.

The present invention provides a protein having an activity for transferring N-acetylgalactosamine to N-acetylglucosamine via a β1-4 linkage. So far as the proteins of the present invention have the properties described herein, the origins thereof and the method for producing them and the like are not limited. Namely, the proteins of the present invention include, for example, native proteins, proteins expressed from recombinant DNA using genetic engineering techniques, and chemically synthesized proteins.

The protein of the present invention has typically an amino acid sequence consisting of 1039 amino acids shown in SEQ ID NO: 1, 998 amino acids shown in SEQ ID NO: 3, 1034 amino acids shown in SEQ ID NO: 26, or 986 amino acids shown in SEQ ID NO: 28. However, it is well-known that in native proteins, there are mutant proteins having one or more variants of amino acids, depending on a mutation of gene based on various species of organisms which produce the proteins, and various ecotypes, or a presence of very similar isozymes or the like. In addition, the term "mutant protein(s)" used herein means proteins and the like having a variant of said amino acid sequence, wherein one or more amino acids are substituted or deleted, or one or more amino acids are inserted or added in the amino acid sequence of SEQ ID NO: 1, 3, 26 or 28, and having the activity of transferring N-acetylgalactosamine to N-acetylglucosamine via a β1-4 linkage. The expression "one or more" here preferably means 1-300, more preferably 1-100, and most preferably 1-50. Generally, in the instance that amino acids are substituted by site-specific variation, the number of amino acids that can be substituted to the extent that the activity of the original protein can be retained is preferably 1-10.

Proteins of the present invention have the amino acid sequences of SEQ ID NO: 1 or 3 and SEQ ID NO: 2 or 4 (lower), or amino acid sequences of SEQ ID NO: 26 or 28 and SEQ ID NO: 27 or 29 (lower) based on the premise of nucleotide sequences of the cloned nucleic acids, but are not exclusively limited to the proteins having these sequences, and are intended to include all homologous proteins having the characteristics described herein. The identity is at least 50% or more, preferably 60%, more preferably 70% or more, even more preferably 80% or more, still more preferably 90% or more, and most preferably 95% or more.

As used herein, the percentage identity of amino acid sequences can be determined by comparison with sequence information using, for example, the BLAST program described by Altschul et al. (Nucl. Acids. Res. 25, pp. 3389-3402, 1997) or the FASTA program described by Pearson et al. (Proc. Natl. Acad. Sci. USA, pp. 2444-2448, 1988). These programs are available from the website of National Center for Biotechnology Information (NCBI) or DNA Data Bank of Japan (DDBJ) on the Internet. Various conditions (parameters) for homology searches with each program are described in detail on the site, and searches are normally performed with default values though some settings may be appropriately changed. Other programs used by those skilled in the art of sequence comparison may also be used.

Generally, a modified protein containing a change from one amino acid to another amino acid having similar properties (such as a change from a hydrophobic amino acid to another hydrophobic amino acid, a change from a hydrophilic amino acid to another hydrophilic amino acid, a change from an acidic amino acid to another acidic amino acid or a change from a basic amino acid to another basic amino acid) often has similar properties to those of the original protein. Methods for preparing such a recombinant protein having a desired variation using genetic engineering techniques are well known to those skilled in the art and such modified proteins are also included in the scope of the present invention.

Proteins of the present invention can be obtained in bulk by, for example, introducing and expressing the DNA sequence of SEQ ID NO: 2, 4, 27 or 29 representing a nucleic acid of the present invention in E. coli, yeast, insect or animal cells using an expression vector capable of being amplified in each host, as described in the examples below.

When the identity search of the protein of the present invention is performed using GENETYX (Genetyx Co.), the NGalNAc-T1 has 47.2% identity to NGalNAc-T2, 84.3% identity to mNGalNAc-T1, and 47.4% identity to mNGalNAc-T2. The NGalNAc-T2 has 46.5% identity to mNGalNAc-T1, and 82.6% identity to mNGalNAc-T2. The mNGalNAc-T1 has 46.3% identity to mNGalNAc-T2.

The NGalNAc-T1 has 26.1% identity in 226 amino acids of C terminus to CSGalNAc-T1, while the NGalNAc-T2 has 21.6% identity in 431 amino acids of C terminus to CSGalNAc-T1 and 25.0% identity in 224 amino acids of C terminus to CSGalNAc-T2.

Further, the NGalNAc-T1 has 19.3% identity to human chondroitin synthase 1 (hCSS1) and 18.0% identity to mouse chondroitin synthase 1 (mCSS1), while the NGalNAc-T2 has 18.2% to hCSS1 and 18.1% to mCSS1.

The mNGalNAc-T1 has 18.5% identity to hCSS1 and 18.1% identity to mCSS1, while the mNGalNAc-T2 has 18.1% identity to hCSS1 and 18.8% identity to mCSS1.

Therefore, it is recognized that the protein of the present invention is a novel one.

In addition, the protein of the present invention has the identity of 27 or more % to the amino acid sequence of SEQ ID NO: 1 or 3.

The protein of the present invention has the identity of 19 or more % to the amino acid sequence of SEQ ID NO: 26 or 28.

In addition, GENETYX is a genetic information processing software for nucleic acid analysis and protein analysis, which is capable of performing general homology analysis and multiple alignment analysis, as well as calculating a signal peptide, a site of promoter, and secondary structure. The program for homology analysis used herein adopts the Lipman-Pearson method (Lipman, D. J. & Pearson, W. R., Science, 277, 1435-1441 (1985)) which is frequently used as a high speed, highly sensitive method.

The amino acid sequences of the proteins and the DNA sequences encoding them disclosed herein can be wholly or partially used to readily isolate genes encoding proteins having a similar physiological activity from that of other species using genetic engineering techniques including hybridization and nucleic acid amplification reactions such as PCR. In such cases, novel proteins encoded by these genes can also be included in the scope of the present invention.

Proteins of the present invention may contain an attached sugar chain if they have an amino acid sequence as defined above as well as the enzymatic activity described above.

More specifically, as described in Examples 2 and 5 below, from the search of an acceptor substrate to the protein of the present invention, said protein acts to transfer GalNAc to GlcNAc via a β1-4 linkage.

Furthermore specifically, the proteins of the present invention have at least one of the following properties (A)-(C), preferably all of these properties:

(A) Specificity of Acceptor Substrates (a) When O-linked oligosaccharides are used as an acceptor substrate, said proteins have the activity of transferring N-acetylgalactosamine to GlcNAcβ1-6(Galβ1-3)GalNAcα-pNp (hereinafter, "core2-pNp"), GlcNAcβ1-3GalNAcα-pNp (hereinafter, "core3-pNp"), GlcNAcβ1-6GalNAcα-pNp (hereinafter, "core6-pNp") via a β1l-4 linkage, wherein the abbreviations used are: GlcNAc, N-acetylglucosamine; GalNAc, N-acetylgalactosamine; Gal, galactose; pNp, p-nitrophenyl. Preferably, said proteins have the transferring activity to core6-pNp.

(b) When N-linked oligosaccharides are used as an acceptor substrate, said proteins have the activity of transferring N-acetylgalactosamine to GlcNAc at the non-reducing end of said oligosaccharides via a β1-4 linkage, provided that said activity reduces when said oligosaccharides have the following properties:

(i) having fucose (Fuc) residues in the structure of said oligosaccharides; and (ii) having one or more branched chains wherein GalNAc residues bind to GlcNAc residues at the non-reducing end.

(B) Optimum pH in Enzymatic Activity

The activity tends to be higher in pH 6.5 of MES (2-morpholineethanesulfonic acid) buffer. In HEPES ([4-(2-hydroxyethyl)-1-piperazinyl]ethanesulfonic acid) buffer, the activity tends to be higher in pH 6.75 for NGalNAc-T1 and pH 7.4 for NGalNAc-T2.

(C) Requirement of Divalent Ions

In NGalNAc-T1, the activity tends to be higher in the MES buffer including at least $Mn^{2+}$, or $Co^{2+}$, preferably $Mn^{2+}$. In NGalNAc-T2, the activity tends to be higher in the MES buffer including $Mg^{2+}$, $Mn^{2+}$, or $Co^{2+}$, preferably $Mg^{2+}$.

(2) Nucleic Acids

Nucleic acids of the present invention include DNA in both single-stranded and double-stranded forms, as well as the RNA complements thereof. DNA includes, for example, native DNA, recombinant DNA, chemically synthesized DNA, DNA amplified by PCR and combinations thereof. The nucleic acid of the present invention is preferably a DNA.

The nucleic acids of the present invention are nucleic acids (including the complement thereof) encoding the amino acids shown in SEQ ID NO: 1, 3, 26 or 28. Typically, the nucleic acids of the present invention have the nucleic acid sequence of SEQ ID NO: 2, 4, 27 or 29 (including the complements thereof), which are clones obtained in the working example below which shows simply an example of the present invention. It is well-known for a person skilled in the art that in native nucleic acids, there are minor mutants derived from various kinds of species which produce them and ecotypes and mutants from a presence of isozymes. Therefore, the nucleic acids of the present invention include, but are not limited to, the nucleic acids having the nucleic acid sequence shown in SEQ ID NO: 2, 4, 27 or 29. The nucleic acids of the present invention include all nucleic acids encoding the proteins of the present invention.

Particularly, the amino acid sequences of the proteins and the DNA sequences encoding them disclosed herein can be wholly or partially used to readily isolate nucleic acids encoding proteins having a similar physiological activity from that of other species using genetic engineering techniques including hybridization and nucleic acid amplification reactions such as PCR. In such cases, such nucleic acids can also be included in the scope of the present invention.

As used herein, "stringent conditions" means hybridization under conditions of moderate or high stringency. Specifically, conditions of moderate stringency can be readily determined by those having ordinary skill in the art based on, for example, the length of the DNA. The basic conditions are shown by Sambrook et al., Molecular Cloning: A Laboratory Manual, 3rd edition, Vol. 1, 7.42-7.45 Cold Spring Harbor Laboratory Press, 2001 and include use of a prewashing solution for the nitrocellulose filters of 5×SSC, 0.5% SDS, 1.0 mM EDTA (pH 8.0), hybridization conditions of about 50% formamide, 2×SSC-6×SSC at about 40-50° C. (or other similar hybridization solution such as Stark's solution, in about 50% formamide at about 42° C.), and washing conditions of 0.5×SSC, 0.1% SDS at about 60° C. Conditions of high stringency can also be readily determined by those skilled in the art based on, for example, the length of the DNA. Generally, such conditions include hybridization and/or washing at a higher temperature and/or a lower salt concentration as compared with conditions of moderate stringency and are defined as hybridization conditions as above followed by washing in 0.2×SSC, 0.1% SDS at about 68° C. Those skilled in the art will recognize that the temperature and the salt concentration of the washing solution can be adjusted as necessary according to factors such as the length of the probe.

Nucleic acid amplification reactions include reactions involving temperature cycles such as polymerase chain reaction (PCR) [Saiki R. K. et al., Science, 230, 1350-1354 (1985)], ligase chain reaction (LCR) [Wu D. Y. et al., Genomics, 4, 560-569 (1989); Barringer K. J. et al., Gene, 89, 117-122 (1990); Barany F., Proc. Natl. Acad. Sci. USA, 88, 189-193 (1991)] and transcription-based amplification [Kwoh D. Y. et al., Proc. Natl. Acad. Sci. USA, 86, 1173-1177 (1989)] as well as isothermal reactions such as strand displacement amplification (SDA) [Walker G. T. et al., Proc. Natl. Acad. Sci. USA, 89, 392-396 (1992); Walker G. T. et al., Nuc. Acids Res., 20, 1691-1696 (1992)], self-sustained sequence replication (3SR) [Guatelli J. C., Proc. Natl. Acad. Sci. USA,. 87, 1874-1878 (1990)], and Qβ replicase system [Lizardi et al., BioTechnology, 6, 1197-1202 (1988)]. Other reactions such as nucleic acid sequence-based amplification (NASBA) using competitive amplification of a target nucleic acid and a variant sequence disclosed in European Patent No. 0525882 can also be used. PCR is preferred.

Homologous nucleic acids cloned by hybridization, nucleic acid amplification reactions or the like as described above have an identity of at least 50% or more, preferably 60% or more, more preferably 70% or more, even more preferably 80% or more, still more preferably 90% or more, and most preferably 95% or more to the nucleotide sequence of SEQ ID NO: 2, 4, 27 or 29 in the Sequence Listing.

The percentage identity of nucleic acid sequences may be determined by visual inspection and mathematical calculation. Alternatively, the percentage identity of two nucleic acid sequences can be determined by comparing sequence information using the GAP computer program, version 6.0 described by Devereux et al., Nucl. Acids Res., 12:387 (1984)

which is available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, Nucl. Acids Res., 14:6745 (1986), as described by Schwartz and Dayhoff, eds; Atlas of Protein Sequence and Structure, National Biomedical Research Foundation, pp. 353-358 (1979); (2) a penalty of 3.0 for each gap and an additional 0.10 penalty for each symbol in each gap; and (3) no penalty for end gaps. Other programs used by one skilled in the art of sequence comparison may also be used.

When the identity search of the nucleic acid of the present invention is performed using GENETYX (Genetyx Co.), the NGalNAc-T1 has 59.7% identity to NGalNAc-T2, 81.4% identity to mNGalNAc-T1, and 59.0% identity to mNGalNAc-T2. The NGalNAc-T2 has 59.7% identity to mNGalNAc-T1, and 83.4% identity to mNGalNAc-T2. The mNGalNAc-T1 has 59.6% identity to mNGalNAc-T2.

The NGalNAc-T1 has 44.6% identity to hCSS1 and 46.0% identity to mCSS1, while the NGalNAc-T2 has 47.3% to hCSS1 and 47.9% to mCSS1.

The mNGalNAc-T1 has 46.4% identity to hCSS1 and 46.6% identity to mCSS1, while mNGalNAc-T2 has 48.6% identity to hCSS1 and 48.7% identity to mCSS1.

Therefore, it is recognized that the nucleic acid of the present invention is a novel one.

In addition, the nucleic acid of the present invention has the identity of 48 or more % to the amino acid sequence of SEQ ID NO: 2 or 4.

The nucleic acid of the present invention has the identity of 49 or more % to the amino acid sequence of SEQ ID NO: 27 or 29.

(3) Recombinant Vectors and Transformants

The present invention provides the recombinant vectors containing the nucleic acid of the present invention. Methods for integrating a DNA fragment of a nucleic acid of the present invention into a vector such as a plasmid are described in, for example, Sambrook, J. et al., Molecular Cloning, A Laboratory Manual (3rd edition), Cold Spring Harbor Laboratory, 1.1 (2001). Commercially available ligation kits (e.g., those available from Takara Shuzo Co., Ltd.) can be conveniently used. Thus obtained recombinant vectors (e.g., recombinant plasmids) are introduced into host cells (e.g., *E. coli*, TB1, LE392, or XL-1Blue, etc.).

Suitable methods for introducing a plasmid into a host cell include the use of calcium chloride or calcium chloride/rubidium chloride or calcium phosphate, electroporation, electro injection, chemical treatment with PEG or the like, and the use of a gene gun as described in Sambrook, J. et al., Molecular Cloning, A Laboratory Manual (3rd edition), Cold Spring Harbor Laboratory, 16.1 (2001).

Vectors can be conveniently prepared by linking a desired gene by a standard method to a recombination vector available in the art (e.g., plasmid DNA). Specific examples of suitable vectors include, but are not limited to, *E. coli*-derived plasmids such as pBluescript, pUC18, pUC19 and pBR 322.

In order to produce desired proteins, especially, expression vectors are useful. The types of expression vectors are not specifically limited to those having the ability to express a desired gene in various prokaryotic and/or eukaryotic host cells to produce a desired protein, but preferably include expression vectors for *E. coli* such as pQE-30, pQE-60, pMAL-C2, pMAL-p2, pSE420; expression vectors for yeasts such as pYES2 (genus *Saccharomyces*), pIC3.5K, pPIC9K, pA0815 (all belonging to genus *Pichia*); and expression vectors for insects such as pBacPAK8/9, pBK283, pVL1392, pBlueBac4.5.

A transformant can be produced by introducing a desired expression vector into a host cell. The host cells employed are not specifically limited to those having the ability to be compatible to the expression vector of the present invention and to be able to be transformed, but various kinds of cells such as native cells are usually used in the art or recombinant cells are artificially established. For example, bacteria (genus *Escherichia*, genus *Bacillus*), yeasts (genus *Saccharomyces*, genus *Pichia*, etc.), mammalian cells, insect cells, and plant cells are exemplified.

The host cells are preferably *E. coli*, yeasts and insect cells, which are exemplified as *E. coli* (M15, JM109, BL21, etc.), yeasts (INVSc1 (genus *Saccharomyces*), GS115, KM71 (genus *Pichia*), etc.), and insect cells (BmN4, bombic larva, etc.). Examples of animal cells are mouse, Xenopus, rat, hamster, monkey or human derived cells or culture cell lines established from these cells. More specifically, the host cell is preferably COS cell which is a cell line derived from a kidney of monkey.

When a bacterium, especially *E. coli* is used as a host cell, the expression vector typically consists of at least a promoter/operator region, a start codon, a gene encoding a desired protein, a stop codon, a terminator and a replicable unit.

When a yeast, plant cell, animal cell or insect cell is used as a host cell, the expression vector typically preferably contains at least a promoter, a start codon, a gene encoding a desired protein, a stop codon and a terminator. It may also contain a DNA encoding a signal peptide, an enhancer sequence, untranslated regions at the 5' and 3' ends of a desired gene, a selectable marker region or a replicable unit, etc., if desired.

Preferred start codons in vectors of the present invention include a methionine codon (ATG). Stop codons include commonly used stop codons (e.g., TAG, TGA, TAA).

The replicable unit means DNA capable of replicating the entire DNA sequence in a host cell, such as natural plasmids, artificially modified plasmids (plasmids prepared from natural plasmids), synthetic plasmids, etc. Preferred plasmids include plasmid pQE30, pET or pCAL or their artificial variants (DNA fragments obtained by treating pQE30, pET or pCAL with suitable restriction endonucleases) for *E. coli*; plasmid pYES2 or pPIC9K for yeasts; and plasmid pBacPAK8/9 for insect cells.

Enhancer sequences and terminator sequences may be those commonly used by those skilled in the art such as those derived from SV40.

As for selectable markers, those commonly used can be used by standard methods. Examples are genes resistant to antibiotics such as tetracycline, ampicillin, kanamycin, neomycin, hygromycin or spectinomycin.

Expression vectors can be prepared by linking at least a promoter, a start codon, a gene encoding a desired protein, a stop codon and a terminator region as described above to a suitable replicable unit in series into a circle. While carrying out the linking process, a suitable DNA fragment (such as a linker or another restriction site) can be used by standard methods such as digestion with a restriction endonuclease or ligation with T4 DNA ligase, if desired.

Introduction [transformation (transduction)] of expression vectors of the present invention into host cells can be performed by using known techniques.

For example, bacteria (such as *E. coli*, *Bacillus subtilis*) can be transformed by the method of Cohen et al. [Proc. Natl. Acad. Sci. USA, 69, 2110 (1972)], the protoplast method [Mol. Gen. Genet., 168, 111 (1979)] or the competent method

[J. Mol. Biol., 56, 209 (1971)]; *Saccharomyces cerevisiae* can be transformed by the method of Hinnen et al [Proc. Natl. Acad. Sci. USA, 75, 1927 (1978)] or the lithium method [J.B. Bacteriol., 153, 163 (1983)]; plant cells can be transformed by the leaf disc method [Science, 227, 129 (1985)] or electroporation [Nature, 319, 791 (1986)]; animal cells can be transformed by the method of Graham [Virology, 52, 456 (1973)]; and insect cells can be transformed by the method of Summers et al. [Mol. Cell. Biol., 3, 2156-2165 (1983)].

(4) Isolation/purification of Proteins

Proteins of the present invention can be expressed (produced) by culturing transformed cells containing an expression vector prepared as described above in a nutrient medium. The nutrient medium preferably contains a carbon, inorganic nitrogen or organic nitrogen source necessary for the growth of host cells (transformants). Examples of carbon sources include glucose, dextran, soluble starch, sucrose and methanol. Examples of inorganic or organic nitrogen sources include ammonium salts, nitrates, amino acids, corn steep liquor, peptone, casein, beef extract, soybean meal and potato extract. If desired, other nutrients (e.g., inorganic salts such as sodium chloride, calcium chloride, sodium dihydrogen phosphate and magnesium chloride; vitamins; antibiotics such as tetracycline, neomycin, ampicillin and kanamycin) may be contained. Incubation of cultures takes place by techniques known in the art. Culture conditions such as temperature, the pH of the medium and the incubation period are appropriately selected to produce a protein of the present invention in mass.

Proteins of the present invention can be obtained from the resulting cultures as follows. That is, when proteins of the present invention accumulate in host cells, the host cells are collected by centrifugation or filtration or the like and suspended in a suitable buffer (e.g., a buffer such as a Tris buffer, a phosphate buffer, an HEPES buffer or an MES buffer at a concentration of about 10 M-100 mM desirably at a pH in the range of 5.0-9.0, though the pH depends on the buffer used), then the cells are disrupted by a method suitable for the host cells used and centrifuged to collect the contents of the host cells. When proteins of the present invention are secreted from host cells, the host cells and culture medium are separated by centrifugation or filtration or the like to give a culture filtrate. The disruption solution of the host cells or the culture filtrate can be used to isolate/purify a protein of the present invention directly or after ammonium sulfate precipitation and dialysis. An isolation/purification method is as follows. When the protein of interest is tagged with 6× histidine, GST, maltose-binding protein or the like, conventional methods based on affinity chromatography suitable for each tag can be used. When the protein of the present invention is produced without using these tags, the method described in detail in the examples below based on ion exchange chromatography can be used, for example. These methods may be combined with gel filtration chromatography, hydrophobic chromatography, isoelectric chromatography or the like.

N-acetylgalactosamine is transferred by the action of proteins of the present invention on glycoprotein, oligosaccharide, polysaccharide or the like having N-acetylglucosamine. Thus, proteins of the present invention can be used to modify a sugar chain of a glycoprotein or to synthesize a sugar. Moreover, the proteins can be administered as immunogens to an animal to prepare antibodies against said proteins, and said antibodies can be used to determine said proteins by immunoassays. Thus, proteins of the present invention and the nucleic acids encoding them are useful in the preparation of such immunogens.

Further, proteins of the present invention can comprise peptides added to facilitate purification and identification. Such peptides include, for example, poly-His or the antigenic identification peptides described in U.S. Pat. No. 5,011,912 and in Hopp et al., Bio/Technology, 6:1204, 1988. One such peptide is the FLAG® peptide, Asp-Tyr-Lys-Asp-Asp-Asp-Asp-Lys (SEQ ID NO: 30) which is highly antigenic and provides an epitope reversibly bound by a specific monoclonal antibody, enabling rapid assay and facile purification of expressed recombinant protein. A murine hybridoma designated 4E11 produces a monoclonal antibody that binds the FLAG® peptide in the presence of certain divalent metal cations, as described in U.S. Pat. No. 5,011,912 hereby incorporated by reference. The 4E11 hybridoma cell line has been deposited with the American Type Culture Collection under Accession No. HB 9259. Monoclonal antibodies that bind the FLAG® peptide are available from Eastman Kodak Co., Scientific Imaging Systems Division, New Haven, Conn.

Specifically, the cDNA of the FLAG is inserted into an expression vector expressing a protein of the present invention to express the FLAG-tagged protein, after which the expression of the protein of the present invention can be confirmed by an anti-FLAG antibody.

(5) Analytical Nucleic Acid

According to the present invention, a nucleic acid which hybridizes to the nucleic acids of the present invention (hereinafter referred to as "analytical nucleic acid") is provided. The analytical nucleic acid of the present invention includes, but is not limited to, typically, native or synthesized fragments derived from nucleic acid encoding the protein of the present invention. As used herein, the term "analytical" includes any of detection, amplification, quantitative and semi-quantitative assays.

(a) Primers

When analytical nucleic acids of the present invention are used as primers for nucleic acid amplification reactions, the analytical nucleic acids of the present invention are oligonucleotides prepared by a process comprising:

selecting two regions from the nucleotide sequence of a gene encoding a protein of SEQ ID NO: 1, 3, 26 or 28 to satisfy the conditions that:

1) each region should have a length of 15-50 bases; and 2) the proportion of G+C in each region should be 40-70%;

generating a single-stranded DNA having a nucleotide sequence identical to or complementary to that of said region or generating a mixture of single-stranded DNAs taking into account degeneracy of the genetic code so that the amino acid residue encoded by said single-stranded DNA is retained, and, as necessary, generating the single-stranded DNA containing a modification without affecting the binding specificity to the nucleotide sequence of the gene encoding said protein.

Primers of the present invention preferably have a sequence homologous to that of a partial region of a nucleic acid of the present invention, but one to two bases may be mismatched.

Primers of the present invention contain 15 bases or more, preferably 18 bases or more, more preferably 21 bases or more, and 50 bases or fewer bases.

The primer of the present invention has typically the nucleic acid sequence selected of a group consisting of SEQ ID NO: 20, 21, 23 and 24, and can be used as a single primer or a suitably combined pair of primers. These nucleotide sequences were designed based on amino acid sequence of SEQ ID 1 or 3 as a PCR primer for cloning gene fragments encoding each protein. The sequence is a primer mixed with all nucleic acids capable of encoding said amino acids.

(b) Probes

When analytical nucleic acids of the present invention are used as probes, the analytical nucleic acids of the present invention preferably have a sequence homologous to that of a total or partial region of the nucleotide sequence of SEQ ID NO: 2, 4, 27 or 29, and further, may have a mismatch of one or two bases. The probes of the present invention have a length of 15 bases and more, preferably 20 bases and more, and within a full length of the encoding region, that is, 3120 bases (corresponding to SEQ ID NO: 2), 2997 bases (corresponding to SEQ ID NO: 4), 3105 bases (corresponding to SEQ ID NO: 27), or 2961 bases (corresponding to SEQ ID NO: 29). The probes have typically the nucleic acid sequence shown in SEQ ID NO: 22 or 25. The probes may be obtained from native nucleic acid treated with restriction enzymes, or may be synthesized oligonucleotides.

Probes of the present invention include labeled probes having a label such as a fluorescent, radioactive or biotinylation label to detect or confirm that the probes have hybridized to a target sequence. The presence of a nucleic acid to be tested in an analyte can be determined by immobilizing the nucleic acid to be tested or an amplification product thereof, hybridizing it to a labeled probe, and after washing, measuring the label bound to the solid phase. Alternatively, it can also be determined by immobilizing the analytical nucleic acid, hybridizing to the nucleic acid to be tested and detecting the nucleic acid to be tested coupled to the solid phase with a labeled probe or the like. In the latter case, the immobilized analytical nucleic is also referred to as a probe.

Generally, nucleic acid amplification methods such as PCR can be readily performed because they are per se well known in the art, and reagent kits and apparatus for them are also commercially available. When a nucleic acid amplification method is performed using a pair of analytical nucleic acids of the present invention described above as primers and a nucleic acid to be tested as the template, the presence of the nucleic acid to be tested in a sample can be known by detecting an amplification product because the nucleic acid to be tested is amplified while no amplification occurs when the nucleic acid to be tested is not contained in the sample. The amplification product can be detected by electrophoresing the reaction solution after amplification, staining the bands with ethidium bromide, immobilizing the amplification product after electrophoresis to a solid phase such as a nylon membrane, hybridizing the immobilized product with a labeled probe that specifically hybridizes to the nucleic acid to be tested, and washing the hybridization product and then detecting said label. Further, the amount of the nucleic acid to be tested in a sample can also be determined by the so-called real-time PCR detection using a quencher fluorescent dye and a reporter fluorescent dye. This method can also be readily carried out using a commercially available real-time PCR detection kit. The nucleic acid to be tested can also be semi-quantitatively assayed based on the intensity of electrophoretic bands. The nucleic acid to be tested may be mRNA or cDNA reversely transcribed from mRNA. When mRNA is to be amplified as the nucleic acid to be tested, the NASBA methods (3SR, TMA) can also be adopted using said pair of primers. The NASBA methods can be readily performed because they are per se well known and kits for them are commercially available.

(c) Microarrays

Analytical nucleic acids of the present invention can be used as microarrays. Microarrays are means for enabling rapid large-scale data analysis of genomic functions. Specifically, a labeled nucleic acid is hybridized to a number of different nucleic acid probes immobilized in high density on a solid substrate such as a glass substrate, a signal from each probe is detected and the collected data are analyzed. As used herein, the "microarray" means an array of an analytical nucleic acid of the present invention on a solid substrate such as a membrane, filter, chip or glass surface.

(6) Antibodies

An antibody that is immunoreactive with the protein of the present invention is provided herein. Such an antibody specifically binds to the polypeptide via the antigen-binding site of the antibody (as opposed to non-specific binding). Therefore, as set forth above, proteins of SEQ ID NOs: 1 and 3, fragments, variants, and fusion proteins and the like can be used as "immunogens" in producing antibodies immunoreactive therewith. More specifically, the proteins, fragments, variants, and fusion proteins and the like include the antigenic determinants or epitopes to induce the formation of an antibody. Such antigenic determinants or epitopes may be either linear or conformational (discontinuous). In addition, said antigenic determinants or epitopes may be identified by any methods known in the art.

Therefore, one aspect of the present invention relates to the antigenic epitopes of the protein of the present invention. Such epitopes are useful raising antibodies, in particular monoclonal antibodies, as described in more detailed below. Additionally, epitopes from the protein of the present invention can be used as research reagents, in assays, to purify specific binding antibodies from substances such as polyclonal sera or supernatants from cultured hybridomas. Such epitopes or variants thereof can be produced using techniques known in the art such as solid-phase synthesis, chemical or enzymatic cleavage of a protein, or by using recombinant DNA technology.

As for antibodies which can be induced by the proteins of the present invention, both polyclonal and monoclonal antibodies can be prepared by conventional techniques, whether a whole body or a part of said proteins have been isolated, or the epitopes have been isolated. See, for example, Monoclonal Antibodies, Hybridomas: A New Dimension in Biological Analyses, Plenum Press, NY, 1980.

Hybridoma cell lines that produce monoclonal antibodies specific for the proteins of the present invention are also contemplated herein. Such hybridomas can be produced and identified by conventional techniques. One method for producing such a hybridoma cell line comprises immunizing an animal with a protein of the present invention; harvesting spleen cells from the immunized animal; fusing said spleen cells to a myeloma cell line, thereby generating hybridoma cells; and identifying a hybridoma cell line that produces a monoclonal antibody that binds said protein. The monoclonal antibodies can be recovered by conventional techniques.

The antibodies of the present invention include chimeric antibodies such as humanized versions of murine monoclonal antibodies. Such humanized antibodies can be prepared by known techniques and offer the advantages of reduced immunogenicity when the antibodies are administered to humans. In one embodiment, a humanized monoclonal antibody comprises the variable region of a murine antibody (or just the antigen-binding site thereof) and a constant region derived from a human antibody. Alternatively, a humanized antibody fragment can comprise the antigen-binding site of a murine monoclonal antibody and a variable region fragment (lacking the antigen-biding site) derived from a human antibody.

The present invention includes antigen-binding antibody fragments that can be also generated by conventional techniques. Such fragments include, but are not limited to, Fab and F(ab')$_2$ as an example. Antibody fragments generated by genetic engineering techniques and derivatives thereof are also provided.

In one embodiment, the antibody is specific to the protein of the present invention, and it does not cross-react with other proteins. Screening procedures by which such antibodies can be identified are publicly known, and may involve, for example, immunoaffinity chromatography.

The antibodies of the invention can be used in assays to detect the presence of the protein or fragments of the present invention, either in vitro or in vivo. The antibodies also can be used in purifying proteins or fragments of the present invention by immunoaffinity chromatography.

Further, a binding partner such as an antibody that can block binding of a protein of the present invention to an acceptor substrate can be used to inhibit a biological activity rising from such a binding. Such a blocking antibody may be identified by any suitable assay procedure, such as by testing the antibody for the ability to inhibit binding of said protein to specific cells expressing the acceptor substrate. Alternatively, a blocking antibody can be identified in assays for the ability to inhibit a biological effect that results from a protein of the present invention binding to the binding partner of target cells.

Such an antibody can be used in an in vitro procedure, or administered in vivo to inhibit a biological activity mediated by the entity that generated the antibody. Disorders caused or exacerbated (directly or indirectly) by the interaction of a protein of the present invention with a binding partner thus can be treated. A therapeutic method involves in vivo administration of a blocking antibody to a mammal in an amount effective to inhibit a binding partner-mediated biological activity. Monoclonal antibodies are generally preferred for use in such therapeutic methods. In one embodiment, an antigen-binding antibody fragment is used.

(7) Cancer Markers and Methods for Detection

The protein or nucleic acids of the present invention can be used as a cancer marker, and be applied to diagnosis and treatment of cancers and the like. As used herein, the term "cancer" means typically all malignant tumors, and includes disease conditions with said malignant tumors. "Cancer" includes, but is not limited to, lung cancer, liver cancer, kidney cancer and leukemia.

"Cancer marker" used herein means the protein and nucleic acids of the present invention that express more than those of a non-cancerous biological sample, when a biological sample is cancerous. In addition, "biological sample" includes tissues, organs, and cells. Blood is preferable, pathological tissue is more preferable.

Specifically, when the protein of the present invention is used as a cancer marker, a method for detection of the present invention includes the steps: (a) quantifying said protein in a biological sample; and (b) estimating that the biological sample is cancerous in the case that the quantity value of said protein in the biological sample is more than that in a control biological sample. In said method for detection, the antibody of the present invention can be used to quantify said protein of the biological sample. According to the present invention, generally, the method for qualifying the protein is not limited to the above methods and can use quantity methods know in the art such as ELISA, Western Blotting. A ratio of the quantity value is preferably 1.5 times or more, more preferably 3 times or more, and even more preferably 10 times or more.

On the other hand, when the nucleic acid of the present invention is used as a cancer marker, a method for detection of the present invention includes the steps of: (a) quantifying said nucleic acid in a biological sample; and (b) estimating that the biological sample is cancerous in the case that the quantity value of said nucleic acid in the biological sample is 1.5 times or more than that of a control biological sample. Preferably, the steps comprise (a) hybridizing at least one of said analytical nucleic acids to said nucleic acid in the biological sample; (b) amplifying said nucleic acid; (c) hybridizing said nucleic acids to the amplification product; (d) quantifying a signal rising from said amplification product and said analytical nucleic acid hybridized; and (e) estimating that the biological sample is cancerous in the case that the quantity value of said signal is 1.5 times or more than that of a corresponding signal of a control biological sample.

More specifically, as described in the example below, canceration can be estimated by determination of a ratio of expression level of the nucleic acids in cancerous tissue and normal tissue by quantitative PCR. According to the present invention, the quantification of the nucleic acid is not limited to this, and for example, RT-PCR, northern blotting, dot blotting or DNA microarray may be used. In such quantification, nucleic acids of genes present generally and broadly in same tissue and the like such as nucleic acids encoding glyceraldehyde-3-phosphate dehydrogenase (GAPDH), β-actin are used as a control. A quantity ratio to be estimated as canceration is preferably 1.5 or more, more preferably 3 or more, even more preferably 10 or more.

The following examples further illustrate the present invention without, however, limiting the invention thereto.

EXAMPLES

Example 1

Preparation of the Human Protein of the Present Invention

1. Search Through a Genetic Database and Determination of the Nucleic Acid Sequence of a Novel N-acetylgalactosamine Transferase A search of similar genes through a genetic database was performed by use of the genes for existing β1,4-galactose transferases. The sequences used were SEQ ID NOs: AL161445, AF038660, AF038661, AF022367, AF038663, AF038664 in the genes for β-1,4-galactose transferases. The search was performed using a program such as Blast [Altschul et al., J. Mol. Biol., 215, 403-410 (1990)].

As a result, GenBank Accession No. N48738 was found as an EST sequence, and GenBank Accession No. AC006205 was found as a genome sequence. As a further result, it is considered that both sequences comprise disparate genes (hereinafter, the genes comprising N48738 and AC006205 refer to NGalNAc-T1 and NGalNAc-T2, respectively). Since the translation initiation sites of both genes were unknown, it was impossible to predict the full length of the genes. Marathon-Ready cDNA (Human Brain or Stomach) from CLONTECH was used for obtaining the information of coding regions (5' RACE: Rapid Amplification of cDNA Ends) and cloning.

Obtaining Information of Coding Region of NGalNAc-T1

AP1 primer included in Marathon cDNA (a DNA fragment having adaptors AP1 and AP2 at both ends) and primer K12R6 generated within the identified sequence part (5'-GCT CCT GCA GCT CCA GCT CCA-3') (SEQ ID NO: 5) were used for PCR (30 cycles of 94° C. for 20 seconds, 60° C. for 30 seconds and 72° C. for 2 minutes). Further, AP2 primer included in Marathon cDNA and primer K12R5 generated within the identified sequence part (5'-AAG CGA CTC CCT CGC GCC GAG T-3') (SEQ ID NO: 6) were used for nested PCR (30 cycles of 94° C. for 20 seconds, 60° C. for 30 seconds and 72° C. for 2 minutes). A fragment of about 0.6 kb obtained as a result was purified by a common method, and the nucleic acid sequence was analyzed. However, since a transmembrane sequence special to glycosyl transferases (hydrophobic 20 amino acids) could have appeared, an EST sequence (GenBank Accession No. PF058197) was discovered based on the obtained sequence and the nucleic acid sequence of NGalNAc-T2 described later by search through genome database. Based on the information of nucleic acid sequence, RT-PCR was performed using two primers (K12F101: 5'-ATG CCG CGG CTC CCG GTG AAG AAG-3' (SEQ ID NO: 7) and K12R5) and the amplification was confirmed. Therefore, it was explained that this EST sequence and the sequence obtained by 5' RACE exist on one mRNA. The full length of nucleotide sequence (3120 bp) was shown in SEQ ID NO: 2.

Obtaining Information of Coding Region of NGalNAc-T2

AP1 primer included in Marathon cDNA (a DNA fragment having adaptors AP1 and AP2 at both ends) and primer K13-R3 generated within the identified sequence part (5'-CAA CAG TTC AAG CTC CAG GAG GTA-3' (SEQ ID NO: 8)) were used for PCR (30 cycles of 94° C. for 20 seconds, 60° C. for 30 seconds and 72° C. for 2 minutes). Further, AP2 primer included in Marathon cDNA and primer K13R2 generated within the identified sequence part (5'-CTG ACG CTT TTC CAC GTT CAC AAT-3' (SEQ ID NO: 9)) were used for nested PCR (30 cycles of 94° C. for 20 seconds, 60° C. for 30 seconds and 72° C. for 2 minutes). A fragment of about 1.0 kb obtained as a result was purified by a common method, and the nucleic acid sequence was analyzed. Further, a coding region of a protein was determined. However, since a transmembrane sequence special to glycosyl transferases (hydrophobic 20 amino acids) could have appeared, further 3 times 5' RACE was performed. The primers used here are shown in Table 2.

As a result, the obtained full length of nucleotide sequence (2997 bp) was shown in SEQ ID NO: 4.

TABLE 2

Various primers used in RACE

Second 5' RACE primers

K13 R6   5'-CAC CCC GTC TCT GCT CTG (SEQ ID NO: 10)
         CGA T-3'

K13 R5   5'-GTC TTC CTG GGG CTG TCA (SEQ ID NO: 11)
         CCA-3'

Third 5' RACE primers

K13 R7   5'-CAC CTC ATC CAT CTG TAG (SEQ ID NO: 12)
         GAA CGT-3'

K13 R8   5'-CTG TCG CCA TGC AAC TTC (SEQ ID NO: 13)
         CAC GT-3'

Fourth 5' RACE primers

K13 R12  5'-AAT GTC GTG GTC CTC GAG (SEQ ID NO: 14)
         GCT CA-3'

K13 R11  5'-GAT GGT AGA ACT GGA GGT (SEQ ID NO: 15)
         GTG GAT-3'

2. Integration of GalNAc-T Gene into an Expression Vector

To prepare an expression system of GalNAc-T, a portion of GalNAc-T gene was first integrated into pFLAG-CMV1 (Sigma).

Integration of NGalNAc-T1 into pFLAG-CMV1

A region corresponding to amino acids 62-1039 of SEQ ID NO: 1 or 2 was amplified by LA Taq DNA polymerase (Takara Shuzo) using Marathon cDNA (Human Brain) as a template, forward primer K12-Hin-F2: 5'-CCC AAG CTT CGG GGG GTC CAC GCT GCG CCA T-3' (SEQ ID NO: 16), and reverse primer K12-Xba-R1: 5'-GCT CTA GAC TCA AGA CGC CCC CGT GCG AGA-3' (SEQ ID NO: 17). The fragment was digested at restriction sites (HindIII and XbaI) included in the primers, and inserted into pFLAG-CMV1 digested with Hind III and XbaI by use of Ligation High (Toyobo) to prepare pFLAG-NGalNAc-T1.

Integration of NGalNAc-T2 into pFLAG-CMV1

A region corresponding to amino acids 57-998 of SEQ ID NO: 3 or 4 was amplified by LA Taq DNA polymerase (Takara Shuzo) using Marathon cDNA (Human Stomach) as a template, forward primer K13-Eco-F1: 5'-GGA ATT CGA GGT ACG GCA GCT GGA GAG AA-3' (SEQ ID NO: 18), and reverse primer K13-Sal-R1: 5'-ACG CGT CGA CCT ACA GCG TCT TCA TCT GGC GA-3' (SEQ ID NO: 19). This fragment was digested at restriction sites (EcoRI and SalI) included in the primers, and inserted temporally into pcDNA3.1 digested with EcoRI and SalI. This was digested with EcoRI and PmeI. The fragment including the active site of NGalNAc-T2 was inserted at the EcoRI-EcoRV site of pFLAG-CMV1 using Ligation High (Toyobo Co.) to prepare pFLAG-NGalNAc-T2.

3. Transfection and Expression of Recombinant Enzymes

15 µg of pFLAG-NGalNAc-T1 or pFLAG-NGalNAc-T2 was induced into $2 \times 10^6$ of COS-1 cells which were cultured overnight in DMEM (Dulbecco's modified Eagle's medium) including 10% FCS (fetal calf serum), using Lipofectamine 2000 (Invitrogen Co.) as a protocol provided by the same company. A supernatant of 48-72 hours was collected. The supernatant was mixed with $NaN_3$ (0.05%), NaCl (150 mM), $CaCl_2$ (2 mM) and an anti-M1 resin (Sigma Co.) (50 µl), and the mixture was stirred overnight at 4° C. The solution of reaction mixture was centrifuged (3000 rpm, 5 min, 4° C.) to collect a pellet. The pellet was combined with 900 µl of 2 mM $CaCl_2$/TBS and re-centrifuged (2000 rpm, 5 min, 4° C.), after which the pellet was suspended in 200 µl of 1 mM $CaCl_2$/TBS to give a sample for assaying activity (NGalNAc-T1 or NGalNAc-T2 enzyme solution).

The enzyme was subjected to conventional SDS-PAGE and Western blotting, and the expression of the intended protein was confirmed. Anti FLAG M2-peroxydase (A-8592, SIGMA Co.) was used as an antibody.

Example 2

Assay of Activity Using the Enzyme of the Present Invention

1. Search for Donor Substrates

A search for a donor substrate of the enzyme of the present invention was performed on various mono-saccharide acceptor substrates, using 5 ml of enzyme solution and various acceptor substrates.

The acceptor substrates were prepared so that each of Gal-α-pNp, Gal-β-oNp, GalNAc-α-Bz, GalNAc-β-pNp, GlcNAc-α-pNp, GlcNAc-β-pNp, Glc-α-pNp, Glc-β-pNp, GlcA-β-pNp, Fuc-α-pNp, Man-α-pNp (thereinbefore, CAL-BIOCHEM Co.), Xyl-α-pNp, Xyl-β-pNp (thereinbefore, SIGMA Co.) was included in 2.5 nmol/20 μl. Further, the solutions of various donor substrates (UDP-GalNAc, UDP-GlcNAc, UDP-Gal, GDP-Man, UDP-GlcA, UDP-Xyl and GDP-Fuc, thereinbefore, SIGMA Co.) are shown in Table 3.

TABLE 3

| GalNAc-T | |
|---|---|
| MES or HEPES (pH 5.5 - | 50 mM |
| UDP-GalNAc | 0.5 mM |
| UDP-[14C]GalNAc | 2 nCi/ul |
| MnCl2 | 20 mM |
| Triron X-100 | 0.5% |

| GlcNAc-T | |
|---|---|
| HEPES (pH 7.0 or 7.5) | 14 mM |
| UDP-GlcNAc | 0.5 mM |
| UDP-[14C]GlcNAc | 2 nCi/ul |
| MnCl2 | 10 mM |
| Triron CF-54 | 0.5% |
| ATP | 0.75 mM |

| Gal-T | |
|---|---|
| HEPES (pH 7.0 or 7.5) | 14 mM |
| UDP-Gal | 0.25 mM |
| UDP-[14C]Gal | 2.5 nCi/ul |
| MnCl2 | 10 mM |
| ATP | 0.75 mM |

| GlcA-T | |
|---|---|
| MES (pH 7.0) | 50 mM |
| UDP-GlcA | 0.25 mM |
| UDP-[14C]GlcA | 2 nCi/ul |
| MnCl2 | 10 mM |

| Xyl-T | |
|---|---|
| MES (pH 7.0) | 50 mM |
| UDP-Xyl | 0.25 mM |
| UDP-[14C]Xyl | 1 nCi/ul |
| MnCl2 | 10 mM |

| Fuc-T | |
|---|---|
| cacodylate buffer (pH 7.0) | 50 mM |
| GDP-[14C]Fuc | 1 nCi/ul |
| MnCl2 | 10 mM |
| ATP | 5 mM |

| Man-T | |
|---|---|
| Tris (pH 7.2) | 50 mM |
| GDP-[14C]Man | 2 nCi/ul |
| MnCl2 | 10 mM |
| Triton X-100 | 0.6% |

All of reaction times were 16 hours. After reaction, non-reactive acceptor substrates with radioactivity were removed with SepPack C18 column (Waters CO.), and radioactivity from donor substrates integrated into acceptor substrates was determined with a liquid scintillation counter. Consequently, there appeared little background even in UDP-GlcA using each of NGalNAc-T1 and NGalNAc-T2, however, the highest activity was detected in the case of UDP-GalNAc as a donor substrate.

2. Search for Acceptor Substrates

Further, in order to investigate acceptors, reactions were performed using each acceptor (10 nmol/20 μl) by itself. As a result, significant radioactivity was detected in the case of GlcNAc-β-pNp (NGalNAc-T1: 256.26 dpm, NGalNAc-T2: 1221.22 dpm). Based on the above results, it was explained that both of NGalNAc-T1 and NGalNAc-T2 are glycosyl transferases capable of transferring GalNAc to GlcNAc-T.

3. Study of Optimum pH

As described above, it was explained that NGalNAc-T1 and NGalNAc-T2 are glycosyl transferases which transfer GalNAc to GlcNAc. Thereat, the optimum pH of both enzymes was studied. The buffer solutions used are MES (pH 5.5, 6.0, 6.26, 6.5, 6.75), HEPES (pH 6.75, 7.0, 7.4). As a result, as shown in Table 4, the activity tends to be higher in pH 6.5 of MES buffer for both NGalNAc-T1 and NGalNAc-T2.

TABLE 4

A result of optimum pH in enzymatic activity of NGalNAc-T1 and NGalNAc-T2

| pH | Incorporation of radioactivity (A) | Blank (B) | (A) − (B) |
|---|---|---|---|
| NGalNAc-T1 | | | |
| MES buffer (pH 5.5) | 339.76 | 263.21 | 76.55 |
| MES buffer (pH 6.0) | 321.04 | 263.21 | 57.83 |
| MES buffer (pH 6.26) | 636.34 | 263.21 | 373.13 |
| MES buffer (pH 6.5) | 1767.72 | 263.21 | 1504.51 |
| MES buffer (pH 6.75) | 923.92 | 263.21 | 660.71 |
| HEPES buffer (pH 6.75) | 1685.06 | 263.21 | 1421.85 |
| HEPES buffer (pH 7.0) | 1138.38 | 263.21 | 875.17 |
| HEPES buffer (pH 7.4) | 2587.48 | 263.21 | 2324.27 (dpm) |
| NGalNAc-T2 | | | |
| MES buffer (pH 5.5) | 336.20 | 263.21 | 72.99 |
| MES buffer (pH 6.0) | 341.92 | 263.21 | 78.71 |
| MES buffer (pH 6.26) | 339.50 | 263.21 | 76.29 |
| MES buffer (pH 6.5) | 753.62 | 263.21 | 490.05 |
| MES buffer (pH 6.75) | 529.24 | 263.21 | 266.03 |
| HEPES buffer (pH 6.75) | 915.16 | 263.21 | 651.95 |
| HEPES buffer (pH 7.0) | 786.70 | 263.21 | 523.49 |
| HEPES buffer (pH 7.4) | 586.32 | 263.21 | 323.11 (dpm) |

In addition, the value (263.21 dpm) of MES (pH 6.75) was adopted as a blank value in the case of a non-enzyme. Further, when pH of HEPES buffer was 7.4 for NGalNAc-T1 and 6.75 for NGalNAc-T2, the highest value was shown. However, the activity did not always increase even when pH increase. Hereinafter, MES (pH 6.5) was used in each of experiments.

4. Studying Requirements of Divalent Cations

Generally, glycosyl transferases require frequently divalent cations. The activity of each enzyme was studied by adding various divalent cations. Consequently, the high values were represented when $Mn^{2+}$ in NGalNAc-T1, and $Mg^{2+}$, $Mn^{2+}$ and $Co^{2+}$ in NGalNAc-T2 were added (see Table 5). Regarding this, both enzymes showed the activity due to adding EDTA which is a chelating agent. From the above results, it was explained that both enzymes require divalent cations.

TABLE 5

A result of requirements of divalent cations in the activity of NGalNAc-T1 and NGalNAc-T2

| | Incorporation of radioactivity (A) | Blank (B) | (A) − (B) |
|---|---|---|---|
| | NGalNAc-T1 | | |
| Divalent cations etc. | | | |
| $MnCl_2$ | 519.47 | 263.21 | 256.26 |
| $MgCl_2$ | 256.36 | 263.21 | −6.85 |
| $ZnCl_2$ | 210.29 | 263.21 | −52.92 |
| $CaCl_2$ | 230.78 | 263.21 | −32.43 |

TABLE 5-continued

A result of requirements of divalent cations
in the activity of NGalNAc-T1 and NGalNAc-T2

| | Incorporation of radioactivity (A) | Blank (B) | (A) − (B) |
|---|---|---|---|
| $CuCl_2$ | 278.77 | 263.21 | 15.56 |
| $CoCl_2$ | 240.91 | 263.21 | −22.30 |
| $CdSO_4$ | 203.39 | 263.21 | −59.82 |
| EDTA | 242.38 | 263.21 | −20.83 |
| | | | (dpm) |
| NGalNAc-T2 | | | |
| pH | | | |
| $MnCl_2$ | 1484.43 | 263.21 | 1221.22 |
| $MgCl_2$ | 3124.16 | 263.21 | 2860.95 |
| $ZnCl_2$ | 187.59 | 263.21 | −75.62 |
| $CaCl_2$ | 217.83 | 263.21 | −45.38 |
| $CuCl_2$ | 218.35 | 263.21 | −44.86 |
| $CoCl_2$ | 1130.63 | 263.21 | 867.42 |
| $CdSO_4$ | 217.92 | 263.21 | −45.29 |
| EDTA | 235.28 | 263.21 | −27.93 |
| | | | (dpm) |

Example 3

Expression Analysis in Various Human Tissues

The expression levels of said gene was quantified by quantitative PCR using cDNA of normal human tissues. The cDNA of normal tissues which was reversely transcribed from total RNA (CLONETECH Co.) was used. As for cell lines, total RNA therefrom was extracted, and cDNA was prepared by conventional methods and was used. The quantitative expression analysis of NGalNAc-T1 was performed using primers: K12-F3 (5'-ctg gtg gat ttc gag agc ga-3' (SEQ ID NO: 20)) and K12-R3 (5'-tgc cgt cca gga tgt tgg-3' (SEQ ID NO: 21)), and probe: K12-MGB3 (5'-gcg gta gag gac gcc-3' (SEQ ID NO: 22)). The quantitative expression analysis of NGalNAc-T2 was performed using primers: K13-F3 (5'-atc gtc atc act gac tat agc agt ga-3'(SEQ ID NO: 23)) and K13-R3 (5'-gaa tgg cat cga tga ctc cag-3' (SEQ ID NO: 24)), and probe: K13-MGB3 (5'-ctc gtg aag gac ccg ca-3' (SEQ ID NO: 25)). A prove with a minor groove binder (Applied Biosystems Co.) was used. Universal PCR Master Mix was used as enzyme and reaction solution, and 25 ml of the reaction solution was quantified with ABI PRISM 7700 Sequence Detection System (together, Applied Biosystems Co.). Glyceraldehyde-3-phosphate dehydrogenase (GAPDH) was used as a standard gene for quantification. A calibration curve for quantification was made by using a template DNA at a known concentration, and the expression level of said gene was normalized. Further, pFLAG-NGalNAc-T1 and pFLAG-NGalNAc-T2 were used as standard DNAs of NGalNAc-T1 and NGalNAc-T2. The reaction temperature was 50° C. for 2 min, 95° C. for 10 min, followed by 50 cycles of 95° C. for 15 sec, 60° C. for 1 min. The result is shown in FIG. 1. It was explained that the amounts of expressions of NGalNAc-T1 and NGalNAc-T2 were high in the nervous system, stomach and spermary, respectively.

Example 4

Expression Analysis of Human Cancerous Tissue

Figure 2:
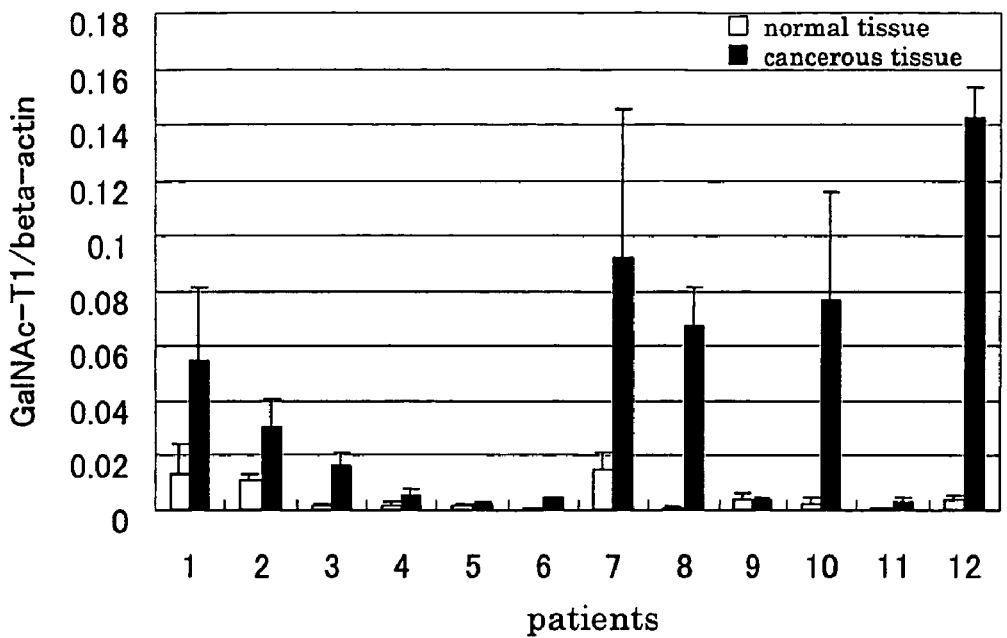
FIG. 2 is a graph showing the quantitative analysis of expression level of NGalNAc-T1 (panel A) or NGalNAc-T2 (panel B) gene in human lung cancerous tissue and normal tissue by the real time PCR. The axis of ordinates represents a relative ratio of expression level of NGalNAc-T1 or NGalNAc-T2 gene to that of a control human β-actin gene. The axis of abscissas represents numbers relating to each patient. The normal tissue and the cancerous tissue are represented as a white bar and a black bar, respectively.
Figure 2:
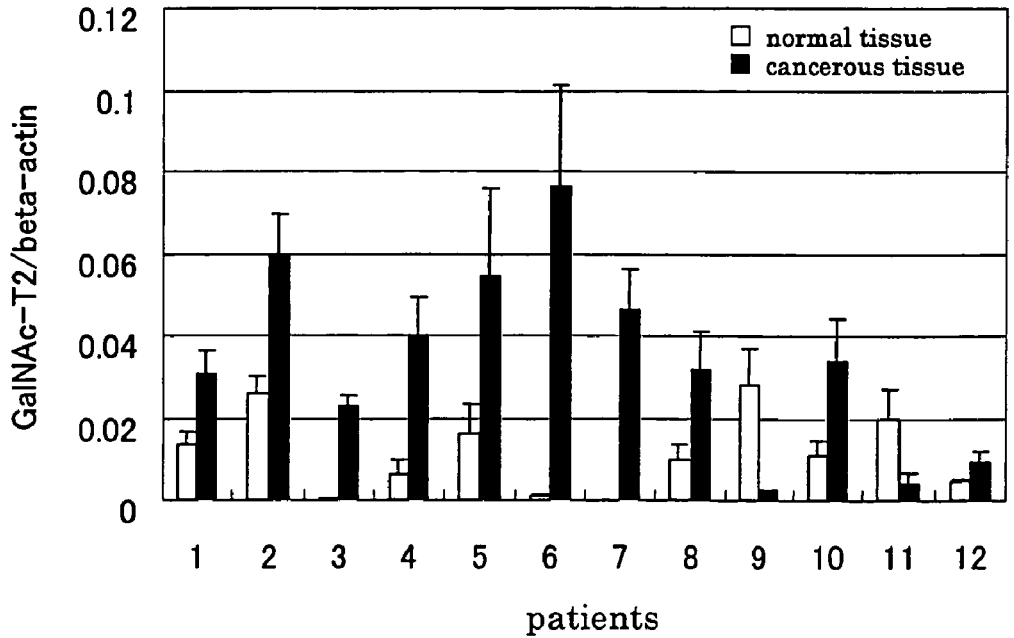

The expression levels of both genes of human lung cancerous tissue and normal lung tissue in the same patient were analyzed. The methods were the same as that of Example 3, provided that b-actin gene was used as a control gene, and Pre-Developed TaqMan Assay Reagents Endogenous Control Human Beta-actin (Applied Biosystems Co.) was used in the quantification (FIG. 2). Consequently, it was explained that both genes can be used at least as a lung cancer marker.

Example 5

Assay for Acceptor Substrates of Glycosyl-transferase Activities

For the reaction of GalNAc-T assay, 50 mM MES buffer (pH 6.5) containing 0.1% triton X-100, 1 mM UDP-GalNAc, 10 mM $MnCl_2$ and 500 μM each acceptor substrate was used. A 10 μl of enzyme solution for 20 μl of each reaction mixture were added and incubated at 37° C. for various periods. After the incubation the mixture was filtrated with Ultrafree-MC column (Millipore, Bedford, Mass.), and 10 μl aliquot was subjected to reversed-phase high performance liquid chromatography (HPLC) on an ODS-80Ts QA column (4.6×250 mm; Tosoh, Tokyo, Japan). A 0.1% $TFA/H_2O$ with 12% acetonitrile was used as a running solution. An ultraviolet spectrophotometer (absorbance at 210 nm), SPD-10A$_{VP}$ (Shimazu, Kyoto, Japan) was used for detection of the peaks. When the pyridyl amino-labeled oligosaccharides were utilized as acceptor substrates, 50 nM substrates were added into the reaction mixtures. For the analyses of the products derived from pyridyl amino labeled oligosaccharides, 100 mM acetic acid/triethylamine (pH4.0) was used as a running solution and the products were eluted with a 30-70% gradient of 1% 1-butanol in running solution at a flow rate of 1.0 ml/min at 55° C.

A 200 μg of the reaction product was dissolved in 150 μl of $D_2O$ using a micro cell and used as a sample for $^1H$ NMR experiments. One-dimensional and two-dimensional $^1H$ NMR spectra were recorded with DMX750 (Bruker, Germany, 750.13 MHz for $^1H$ nucleus) and ECA800 (JEOL, Tokyo, Japan, 800.14 MHz for $^1H$ nucleus) spectrometers at 25° C. Methylene proton of benzyl group in higher field (4.576 ppm) was used as a reference for the $^1H$ NMR chemical shifts tentatively.

To investigate the specificity for acceptor substrates, N- and O-glycans containing GlcNAc on their non-reducing termini were utilized. As shown in Table 6 and 7, all acceptor substrates examined could receive a GalNAc residue.

TABLE 6

Substrate specificity of NGalNAc-Ts

| | | Relative activity (%) | |
|---|---|---|---|
| | Acceptor substrate | NGalNAc-T1 | NGalNAc-T2 |
| 1. | GlcNAcβ-Bz | 100 | 100 |
| 2. | GlcNAcβ1-6(Gaβ1-3)GalNAcα-pNp (core2-pNp) | 15.2 | 11.4 |
| 3. | GlcNAcβ1-3GalNAcα-pNp (core3-pNp) | 20.0 | 32.3 |
| 4. | GlcNAcβ1-6GalNAcα-pNp (core6-pNp) | 190.7 | 220.4 |

TABLE 7

Substrate specificity of NGalNAc-Ts

| | | Relative activity (%) | |
|---|---|---|---|
| | Acceptor substrate | NGalNAc-T1 | NGalNAc-T2 |
| 1. | GlcNAcβ1-2Manα1→6 Manβ1-4GlcNAcβ1-4 GlcNAc-PA<br>GlcNAcβ1-2Manα1→3 | 100 | 100 |
| 2. | Fucα1↓6<br>GlcNAcβ1-2Manα1→6 Manβ1-4GlcNAcβ1-4 GlcNAc-PA<br>GlcNAcβ1-2Manα1→3 | 76.8 | 87.1 |
| 3. | Galβ1-4GlcNAcβ1-2Manα1→6 Manβ1-4GlcNAcβ1-4 GlcNAc-PA<br>GlcNAcβ1-2Manα1→3 | 26.2 | 45.0 |
| 4. | Fucα1↓6<br>Galβ1-4GlcNAcβ1-2Manα1→6 Manβ1-4GlcNAcβ1-4 GlcNAc-PA<br>GlcNAcβ1-2Manα1→3 | 26.7 | 51.7 |
| 5. | GlcNAcβ1-2Manα1→6 Manβ1-4GlcNAcβ1-4 GlcNAc-PA<br>Galβ1-4GlcNAcβ1-2Manα1→3 | 16.2 | 21.6 |
| 6. | Fucα1↓6<br>GlcNAcβ1-2Manα1→6 Manβ1-4GlcNAcβ1-4 GlcNAc-PA<br>Galβ1-4GlcNAcβ1-2Manα1→3 | 3.4 | 5.0 |

Figure 5:
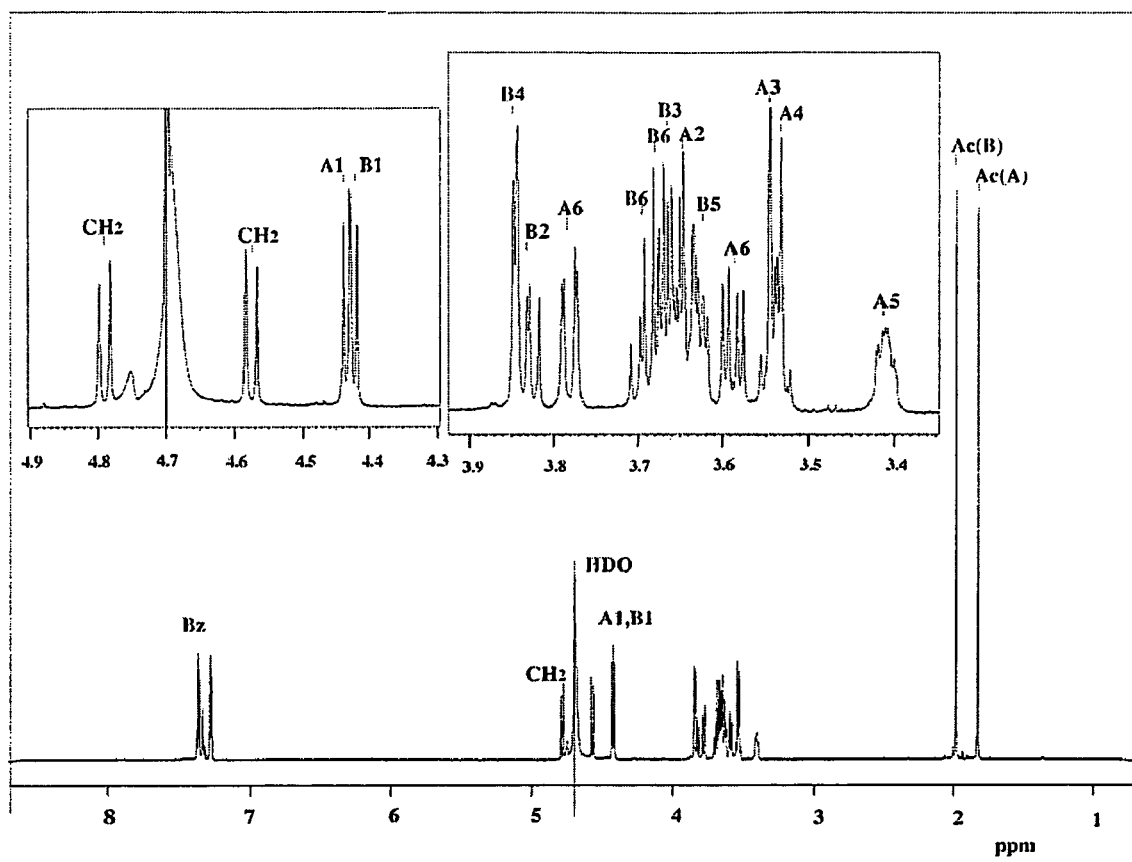
FIG. 5 shows one-dimensional $^1$H NMR spectrum of the structure of GalNAcb1-4GlcNAc-O-Bz produced by NGalNAc-T2.
Figure 6:
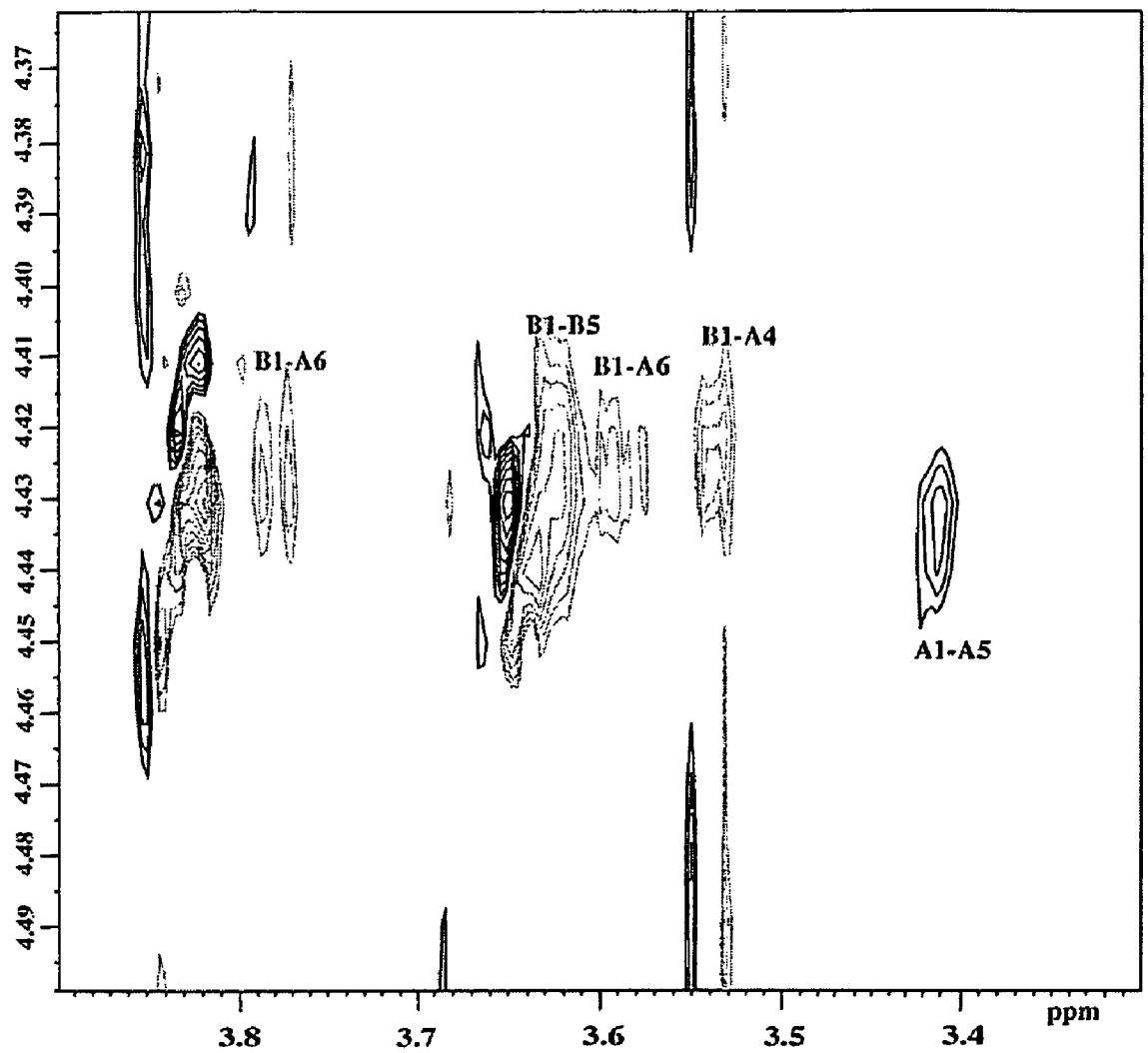
FIG. 6 shows two-dimensional $^1$H NMR spectrum of the structure of GalNAcb1-4GlcNAc-O-Bz produced by NGalNAc-T2.

$^1$H NMR spectroscopy was performed to determine the newly formed glycosidic linkage of NGalNAc-T2 product. One-dimensional $^1$H NMR spectrum of the NGalNAc-T2 product is shown in FIG. 5. In the NMR spectra, signal integrals (not shown, five phenyl protons of Bz, two methylene protons of Bz, two anomeric protons, twelve sugar protons except anomeric protons, six methyl protons of two N-acetyl groups) were in good correspondence with the structure of GalNAc-GlcNAc-O-Bz. As shown in FIG. 5 and in Table 8, two anomeric protons revealed resonances at very close magnetic field with coupling constant ($J_{1,2}$) larger than 8 Hz. This indicates that two pyranoses in the samples are in β-gluco-configuration. All $^1$H signals could be assigned after high resolutional detections of COSY, TOCSY and NOESY experiments. The anomeric resonance in the lower field showed NOE with two methylene protons of benzyl group in the sample (not shown), on the other hand, the anomeric resonance in higher field did not show NOE with methylene protons (not shown). The facts mean that the anomeric resonance in the lower field is responsible for the anomeric proton of the substrate pyranose (β-GlcNAc, defined as A), and that the anomeric proton in the higher field corresponds to anomeric proton of the transferred pyranose (β-GalNAc, defined as B). The chemical shifts and coupling constants of sugar part of the sample were shown in Table 8. The chemical shift and signal splitting of B-4 resonance was characteristic in β-Gal configuration [see Reference 15], and the order in chemical shift of A1-A6 protons was characteristically similar to observed spectrum of β-GlcNAc in LNnT (Galβ1-4GlcNAcβ1-3Galβ1-4Glc). As shown in FIG. 6, weak NOE cross peak between B1 and A4 and very weak NOE cross peaks between B1 and two A6 were observed in addition to strong inner residual NOEs between B1 and B5 and between A1 and A5. These suggest the existence of β1-4 linkage between two pyranoses. Results in NMR experiments thus indicated clearly that the product by NGalNAc-T2 is GalNAcβ1-4GlcNAc-O-Bz.

TABLE 8

Chemical shifts (ppm) and coupling constants (Hz) of sugar CH protons in the NGalNAc-T2 product

| | NGalNAc-T2 product | |
|---|---|---|
| | GlcNAc | GalNAc |
| $^1$H Chemical shifts (ppm)$^a$ | | |
| δ1 | 4.434 | 4.425 |
| δ2 | 3.647 | 3.831 |
| δ3 | 3.546 | 3.665 |
| δ4 | 3.534 | 3.846 |
| δ5 | 3.411 | 3.628 |
| δ6 | 3.589 | 3.696 |
| δ6 | 3.782 | 3.680 |
| δCH$_3$ | 1.830 | 1.987 |
| Coupling constants (Hz) | | |
| $J_{1,2}$ | 8.5 | 8.4 |
| $J_{2,3}$ | | 10.8 |
| $J_{4,5}$ | | <3.7 |
| $J_{5,6a}$ | 5.6 | <3.7 |
| $J_{5,6b}$ | 2.0 | |
| $J_{6a,6b}$ | 12.1 | |

$^a$The chemical shifts were set as the higher field signal of the benzyl methylene protons is ppm tentatively.

Example 6

LacdiNAc Synthesizing Activity of NGalNAc-T2 Toward Asialo/agalacto-fetal Calf Fetuin As demonstrated in Table 6 and 7, both NGalNAc-T1 and -T2 transferred GalNAc toward both O- and N-glycans substrates. The LacdiNAc (GalNAcβ1-4GlcNAc) structures have been found in N-glycans of some glycoproteins in human. Therefore, to determine the activity of NGalNAc-T2 to transfer GalNAc to a glycoprotein, fetal calf fetuin (FCF), which has both N- and O-glycans, was utilized as an acceptor substrate.

Fetal calf fetuin (FCF), neuraminidase, β1-4 galactosidase and glycopeptidase F were purchased from Sigma, Nacalai Tesque (Kyoto, Japan), Calbiochem and Takara, respectively. Asialo/agalacto-FCF was prepared from 200 μg of FCF by incubating with 4 μU of neuraminidase and 12 μU of β1,4-galactosidase at 37° C. for 16 hr. The transfer of GalNAc by GalNAc-T2 to glycoprotein was performed in 20 μl of a standard reaction mixture containing 50 μg of asialo/agalacto-FCF produced by glycosidase treatment. After the incubation at 37° C. for 16 hr, each 5 μl of the reaction mixture was digested with glycopeptidase F (GPF) according to manufacture's instruction. For detection of transferred GalNAc, horseradish peroxidase (HRP) conjugated lectin, Wisteria floribunda agglutinin (WFA) (EY Laboratories, San Mateo, Calif.), was used. A 1 μl of reaction mixtures subjected to 12.5% SDS-PAGE were transferred to nitrocellulose membrane (Schleicher & Schuell, Keene, N.H.) and stained with 0.1% HRP conjugated WFA lectin. The signals were detected using enhanced chemiluminescence (ECL) and Hyperfilm ECL (Amersham Biosciences).

Figure 3:
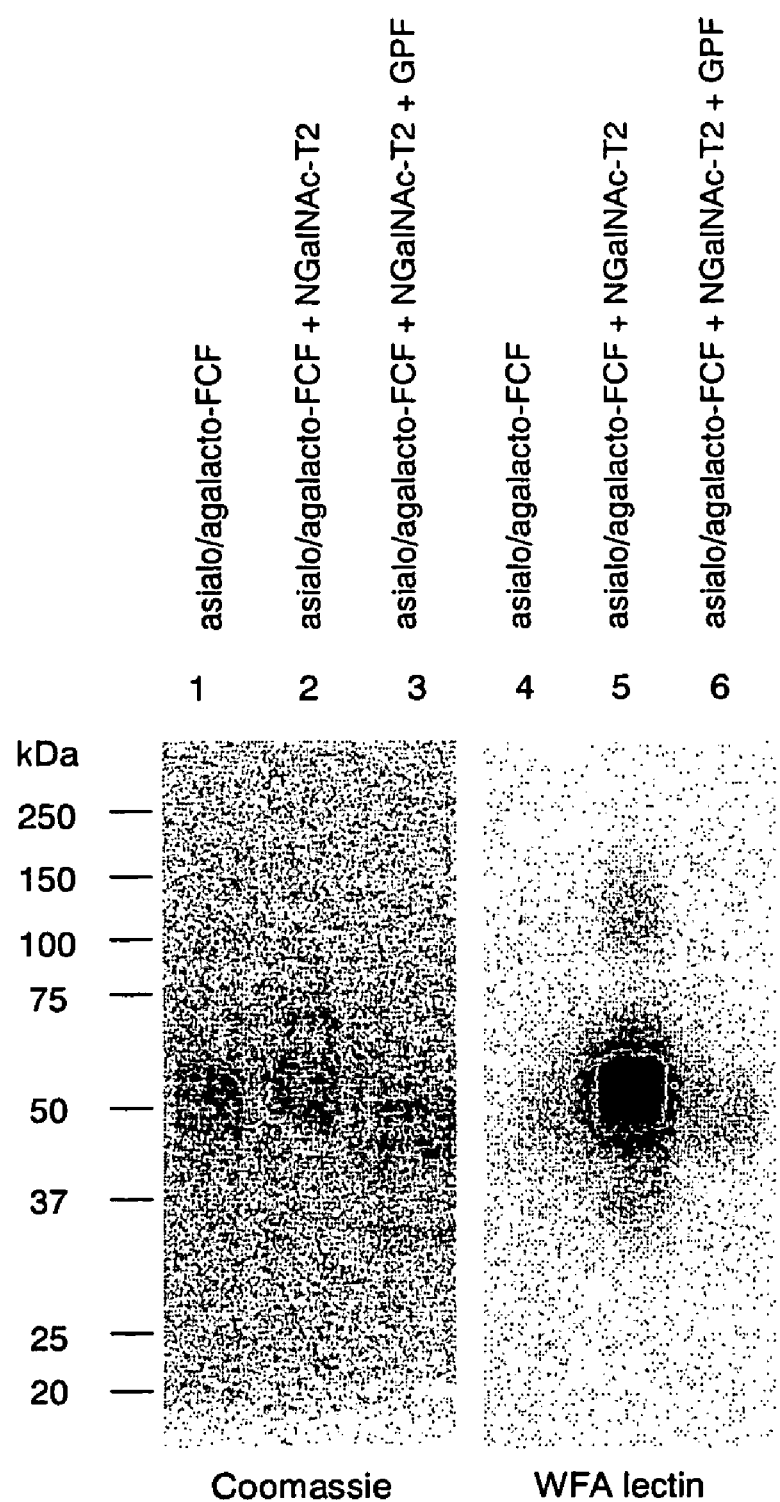
FIG. 3 shows LacdiNAc synthesizing activity of NGalNAc-T2 toward asialo/agalacto-fetal calf fetuin. The asialo/agalacto-FCF appears as approximately 55 and 60 kDa band (lane 1). The NGalNAc-T2 effectively transfers GalNAc to asialo/agalacto-FCF (lane 5). The band mostly disappeared by GPF treatment (lane 6).
Figure 4:
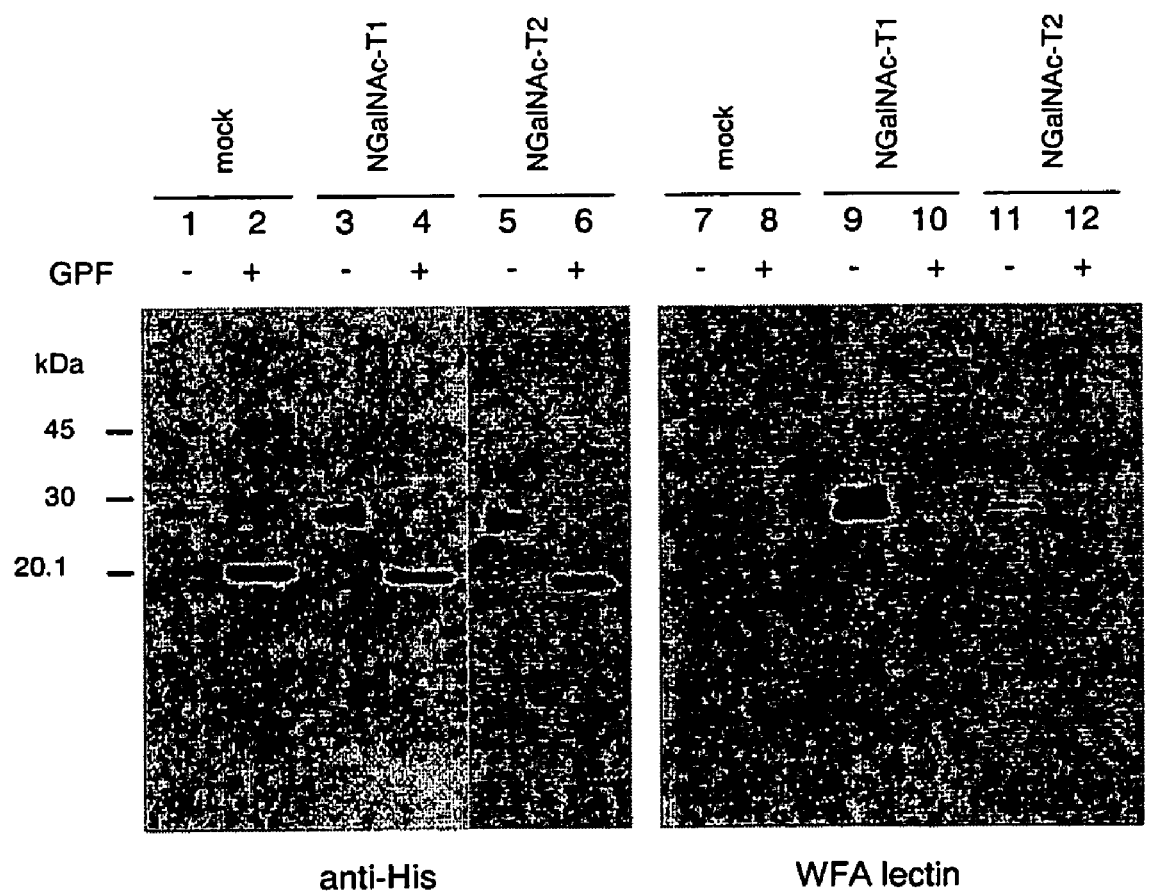
FIG. 4 shows an analysis of N-glycan structures of glycodelin from NGalNAc-T1 and NGalNAc-T2 gene transfected CHO cells. The non-reducing terminal GalNAc is detected only when NGalNAc-T1 or NGalNAc-T2 gene is co-transfected with glycodelin gene.

As shown in FIG. 3, asialo/agalacto-FCF appeared as approximately 55 and 60 kDa band (lane 1). NGalNAc-T2 effectively transferred GalNAc to asialo/agalacto-FCF (lane 5). Furthermore, the band mostly disappeared by a GPF treatment, and its molecular size was detected at approximately 45 and 50 kDa position by Coomassie staining (FIG. 3, lane 3 and 6). In the case of NGalNAc-T1, the activity toward asialo/agalacto-FCF was same as NGalNAc-T2 (data not shown).

Example 7

Analysis of N-glycan Structures on Glycodelin from NGalNAc-T1 and -T2 Gene Transfected CHO Cells As shown above, both NGalNAc-T1 and -T2 could synthesize LacdiNAc structures on mono- and oligosaccharide acceptors. Actually, it is known that the LacdiNAc structures exist in N-glycans on some glycoproteins. Therefore we examined the ability of NGalNAc-T1 to construct LacdiNAc on glycodelin, which is one of major glycoproteins carrying LacdiNAc structures, in vivo. CHO cells were employed for this purpose, because glycodelin produced in CHO cells is devoid of any of the LacdiNAc-based chains.

The glycodelin expression vector was transfected into CHO cells expressing NGalNAc-T1 or -T2 gene and the culture medium was collected from 48 hr-culture medium. Glycodelin was harvested with WFA affinity column from the culture medium. The harvested glycodelin was applied to SDS-PAGE and used for lectin blotting with WFA.

As shown in FIG. 7, the non-reducing terminal GalNAc was detected only when NGalNAc-T1 or -T2 gene was co-transfected with glycodelin gene. These bands were disappeared by N-glycanase™ treatment, therefore these GalNAc residues might exist in N-glycans.

Example 8

Preparation of Mouse Proteins of the Present Invention

1. Search Through a Genetic Database and Determination of the Nucleic Acid Sequence of a Novel Mouse N-acetylgalactosaminyltransferase A search of similar genes through a mouse genomic database (UCSC Human Genome Project, November 2001 mouse assembly archived Sep. 15, 2002, http://genome-archive.cse.ucsc.edu/) was performed by use of the genes for existing human NGalNAc-T1 and -T2. The sequences used were SEQ ID NOs: 1, 3, 26 and 28. The search was performed using a program such as Blast [Altschul et al., J. Mol. Biol., 215, 403-410 (1990)].

As a result, two homologous genes were found on mouse chromosome 7 and 6. The nucleotide and amino acid sequences of the first gene on chromosome 7, which is an ortholog of human NGalNAc-T1, were shown as SEQ ID NOs: 26 and 28. The second ones on chromosome 6 were described as SEQ ID NOs: 27 and 29.

2. Integration of GalNAc-T Genes into an Expression Vector

To prepare each expression system of mouse NGalNAc-T, a portion of each gene was first integrated into pFLAG-CMV1 (Sigma).

Integration of mNGalNAc-T1 into pFLAQ-CMAV1

The mouse NGalNAc-T2 (mNGalNAc-T2) gene encoding its putative catalytic domain (amino acid 45 to 1,034) was amplified with two primers, 5'-CCC AAG CTT CGC CTG GGC TAC GGG CGA GAT-3' (SEQ ID NO: 31) and 5'-GCT CTA GAC TCA GGA TCG CTG TGC GCG GGC A-3' (SEQ ID NO: 32), using the cDNA derived from mouse brain as a template. The mRNA was prepared from mouse brain with RNeasy mini kit (Qiagen), then the cDNA was synthesized with SuperScript first-strand synthesis system for RT-PCR (Invitrogen). For the PCR, LA Taq DNA polymerase (Takara) was used. The amplified 2.7 kb fragment was digested with endonuclease Hind III and Xba I, then the digested fragment was inserted into pFLAG-CMV-1 and pFLAG-mNGalNAc-T1 was constructed.

Integration of mNGalNAc-T2 into pFLAG-CMAV1

The mouse NGalNAc-T2 (mNGalNAc-T2) gene encoding its putative catalytic domain (amino acid 57 to 986) was amplified with two primers, 5'-CCC AAG CTT CGG CCC AGG CCG GCG GGA ACC-3' (SEQ ID NO: 33) and 5'-GGA ATT CTC ACG GCA TCT TCA TTT GGC GA-3' (SEQ ID NO: 34), using the cDNA derived from mouse stomach as a template. The mRNA was prepared from mouse stomach with RNeasy mini kit (Qiagen), then the cDNA was synthesized with SuperScript first-strand synthesis system for RT-PCR (Invitrogen). For the PCR, LA Taq DNA polymerase (Takara) was used. The amplified 2.7 kb fragment was digested with endonuclease Hind III and EcoR I, then the digested fragment was inserted into pFLAG-CMV-1 and pFLAG-mNGalNAc-T2 was constructed.

3. Transfection and Expression of Recombinant Enzymes

A 15 μg of pFLAG-mNGalNAc-T1 or pFLAG-mNGalNAc-T2 was induced into $2 \times 10^6$ of HEK293T cells which were cultured overnight in DMEM (Dulbecco's modified Eagle's medium) including 10% FCS (fetal calf serum), using Lipofectamine 2000 (Invitrogen Co.) as a protocol provided by the same company. A supernatant of 48-72 hors was collected. The supernatant was mixed with $NaN_3$ (0.05%), NaCl (150 mM, CaCl$_2$ (2 mM) and an anti-M1 resin (Sigma Co.) (50 µl), and the mixture was stirred overnight (3000 rpm, 5 min, 4° C.) to collect a pellet. The pellet was combined with 900 µl of 2 mM CaCl$_2$/TBS and re-centrifuged (2000 rpm, 5 min, 4° C.), after which the pellet was suspended in 200 µl of 1 mM CaCl$_2$/TBS to give a sample for assaying activity (mNGalNAc-T1 or mNGalNAc-T2 enzyme solution).

The enzyme was subjected to conventional SDS-PAGE and Western blotting, and the expression of the intended protein was confirmed. Anti-FLAG M2-peroxydase (A-8592, SIGAIA Co.) was used as an antibody.

REFERENCES

1. Sugita, M., S. Itonori, F. Inagaki and T. Hori, Characterization of two glucuronic acid-containing glycosphingolipids in larvae of the green-bottle fly, *Lucilia caesar*. J. Biol. Chem., 1989. 264, p. 15028-33
2. Helling, F., R. D. Dennis, B. Weske, G. Nores, J. Peter-Katalinic, U. Dabrowsli, H. Egge and H. Wiegandt, Glycosphingolipids in insects. The amphoteric moiety, N-acetylglucosamine-linked phosphoethanolamine, distinguishes a group of ceramide oligosaccharides from the pupae of *Calliphora vicina* (Insecta: Diptera). Eur. J. Biochem., 1991. 200, p. 409-21
3. Weisshaar, G., J. Hiyama, A. G. Renwick and M. Nimtz, NMR investigations of the N-linked oligosaccharides at individual glyocosylation sites of human lutropin. Eur. J. Biochem., 1991. 195, p. 257-68
4. White, T., E. P. Bennet, K. Takio, T. Sorenesen, N. Bonding and H. Clausen, Purification and cDNA cloning of a human UDP-N-acetyl-alpha-D-galactosamine:polypeptide N-acetylgalactosaminyltransferase. J. Biol. Chem., 1995. 270, p. 24156-65
5. Bennett, E. P., H. Hassan and H. Clausen, cDNA cloning and expression of a novel human UDP-N-acetyl-alpha-D-galactosamine. Polypeptide N-acetylgalactosaminyltransferase, GalNAc-t3. J. Biol. Chem., 1996. 271, p. 17006-12
6. Bennett, E. P., H. Hassan, U. Mandel, E. Mirgorodskaya, P. Roepstorff, J. Burchell, J. Taylor-Papadimitriou, M. A. Hollingsworth, G. Merkx, A. G. van Kessel, H. Eiberg, R. Steffensen and H. Clausen, Cloning of a human UDP-N-acetyl-alpha-D-galactosamine:polypeptide N-acetylgalactosaminyltransferase that complements other GalNAc-transferases in complete O-glycosylation of the MUC1 tandem repeat. J. Biol. Chem., 1998. 273, p. 30472-81
7. Bennett, E. P., H. Hassan, J. Mandel, M. A. Hollingsworth, N. Akisawa, Y. Ikematsu, G. Merkx, A. G. van Kessel, S. Olofsson and H. Clausen, Cloning and characterization of a close homologue of human UDP-N-acetyl-alpha-D-galactosamine:polypeptide N-acetylgalactosaminyltransferase-T3, designed GalNAc-T6. Evidence for genetic but not functional redundancy. J. Biol. Chem., 1999. 274, p. 25362-70
8. Bennett, E. P., H. Hassan, M. A. Hollingsworth and H. Clausen, A novel human UDP-N-acetyl-D-galactosamine: polypeptide N-acetylgalactosaminyltransferase, GalNAc-T7, with specificity for partial GalNAc-glycosylated acceptor substrates. FEBS Lett., 1999. 460, p. 226-30
9. White, K. E., B. Lorenz, T. Meitinger, T. M. Strom and M. J. Econs, Gene, 2000. 246, p. 347-56
10. Toba, S., M. Tenno, M. Konishi, T. Mikami, N. Itoh and A. Kurosaka, Brain-specific expression of a novel human UDP-GalNAc:polypeptide N-acetylgalactosaminyltransferase (GalNAc-T9). Biochim. Biophys. Acta., 2000. 7, p. 264-8
11. Nagata, Y., S. Yamashiro, J. Yodoi, K. O. Lloyd, H. Shiku and K. Furukawa, Expression cloning of beta 1,4 N-acetylgalactosaminyltransferase cDNAs that determine the expression of GM2 and GD2 gangliosides. J. Biol. Chem., 1992. 269, p. 12082-9
12. Yamamoto, F., J. Marken, T. Tsuji, T. White, H. Clausen and S. Hakomori, Cloning and characterization of DNA complementary to human UDP-GalNAc:Fuc alpha 1 - - - 2Gal alpha 1 - - - 3GalNAc transferase (histo-blood group A transferase) mRNA. J. Biol. Chem., 1990. 265, p. 1146-51
13. Xu, H., T. Storch, M. Yu, S. P. Elliott and D. B. Haslam, Characterization of the human Forssman synthetase gene. An evolving association between glycolipid synthesis and host-microbial interactions. J. Biol. Chem., 1999. 274, p. 29390-8
14. Guo, J. M., Y. Zhang, L. Cheng, H. Iwasaki, H. Wang, T. Kubota, K. Tachibana and H. Narimatsu, Molecular cloning and characterization of a novel member of the UDP-GalNAc:polypeptide N-acetylgalactosaminyltransferase family, pp-GalNAc-T12(1). FEBS Lett., 2002. 524, p. 211-8
15. Ishizuka, Y., T. Nemoto, M. Fujiwara, K. Fujita and H. Nakanish, Three-dimensional structure of fucosyllactoses in an aqueous solution. J. Carbohydr. Chem., 1999. 18, p. 523-33

INDUSTRIAL APPLICABILITY

According to the present invention, an enzyme which transfers N-acetylgalactosamine to N-acetylglucosamine via a β1-4 linkage was isolated and the structure of its gene was explained. This led to the production of said enzyme or the like by genetic engineering techniques, the production of oligosaccharides using said enzyme, and the diagnosis of diseases on the basis of said gene or the like.

---

The invention claimed is:

1. An isolated nucleic acid encoding a protein having an amino acid sequence which is selected from the group consisting of SEQ ID NO: 3 and a variant thereof, wherein said protein has the activity of transferring N-acetylgalactosamine to N-acetylglucosamine via a β1-4 linkage, wherein the variant has the amino acid sequence of SEQ ID NO:3 with 1 to 10 amino acids substituted or deleted, or 1 to 10 amino acids inserted or added.

2. The nucleic acid of claim 1 having the nucleotide sequence of SEQ ID NO: 4.

3. A recombinant vector containing the nucleic acid of claim 1 and being capable of expressing said nucleic acid in a host cell.

4. An isolated host cell transformed with the recombinant vector of claim 3.

* * * * *